United States Patent
Sun et al.

(10) Patent No.: US 9,463,254 B2
(45) Date of Patent: Oct. 11, 2016

(54) MOLECULAR DESIGN TOWARD DUAL-MODALITY PROBES FOR RADIOISOTOPE-BASED IMAGING (PET OR SPECT) AND MRI

(71) Applicant: Board of Regents, The University of Texas System, Austin, TX (US)

(72) Inventors: Xiankai Sun, Coppell, TX (US); Amit Kumar, Dallas, TX (US); Zoltan Kovacs, Lewisville, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 89 days.

(21) Appl. No.: 14/298,688

(22) Filed: Jun. 6, 2014

(65) Prior Publication Data

US 2014/0363376 A1    Dec. 11, 2014

Related U.S. Application Data

(60) Provisional application No. 61/832,491, filed on Jun. 7, 2013.

(51) Int. Cl.
| | |
|---|---|
| A61K 49/00 | (2006.01) |
| A61K 51/00 | (2006.01) |
| A61K 49/14 | (2006.01) |
| A61K 49/12 | (2006.01) |
| A61K 51/06 | (2006.01) |
| A61K 51/08 | (2006.01) |

(52) U.S. Cl.
CPC ........... *A61K 49/14* (2013.01); *A61K 49/0002* (2013.01); *A61K 49/124* (2013.01); *A61K 51/065* (2013.01); *A61K 51/088* (2013.01)

(58) Field of Classification Search
CPC ...... A61K 49/00; A61K 49/12; A61K 49/14; A61K 51/065
See application file for complete search history.

(56) References Cited

U.S. PATENT DOCUMENTS

| | | | |
|---|---|---|---|
| 5,053,503 | A | 10/1991 | Dean et al. |
| 5,466,439 | A | 11/1995 | Gibby et al. |
| 5,565,562 | A | 10/1996 | Parker et al. |
| 5,972,307 | A | 10/1999 | Carvalho et al. |
| 6,057,419 | A | 5/2000 | Schmitt-Willich et al. |
| 2003/0228262 | A1 | 12/2003 | Brechbiel et al. |

FOREIGN PATENT DOCUMENTS

| | | |
|---|---|---|
| CN | 102558291 | 7/2012 |
| WO | WO 2010/030120 | 3/2010 |

OTHER PUBLICATIONS

Yasushi Arano et al., Synthesis and Evaluation of Diastereoisomers of 1,4,7-Triazacyclononane-1,4,7-tris-(glutaric acid) )NOTGA) for Multimeric Radiopharmaceuticals of Gallium, Bioconjugate Chemistry, 2012, 23, 2229-2238.*

Caravan, "Strategies for increasing the sensitivity of gadolinium based MRI contrast agents," *Chemical Society Reviews*, 35:512-523, 2006.

Caravan, et al., "Gadolinium(III) Chelates as MRI Contrast Agents: Structure, Dynamics, and Applications," *Chemical Reviews*, 99:2293-2352, 1999.

Chen, et al., "Gold Nanocages: Engineering Their Structure for Biomedical Applications," *Advanced Materials*, 17:2255-2261, 2005.

Cheng and Tsourkas, "Paramagnetic porous polymersomes," *Langmuir*, 24:8169-8173, 2008.

Cheng, et al., "Facile Preparation of Multifunctional Upconversion Nanoprobes for Multimodal Imaging and Dual—Targeted Photothermal Therapy," *Angewandte Chemie International Edition*, 50:7385-7390, 2011.

Dong, et al., "Magnetic resonance angiography with gadomer-17. An animal study original investigation," *Investigative Radiology*, 33:699-708, 1998.

Gao, et al., "In vivo cancer targeting and imaging with semiconductor quantum dots," *Nat. Biotech.*, 22: 969-976, 2004.

Kobayashi and Brechbiel, "Dendrimer-based macromolecular MRI contrast agents: characteristics and application," *Molecular Imaging*, 2:1-10, 2003.

Lux, et al., "Ultrasmall Rigid Particles as Multimodal Probes for Medical Applications," *Angewandte Chemie International Edition*, 50:12299-12303, 2011.

Ma, et al., "Superparamagnetic iron oxide nanoparticles stabilized by alginate: pharmacokinetics, tissue distribution, and applications in detecting liver cancers," *International Journal of Pharmaceutics*, 354:217-226, 2008.

Morawski, et al., "Targeted nanoparticles for quantitative imaging of sparse molecular epitopes with MRI," *Magnetic Resonance in Medicine*, 51:480-486, 2004.

Nicolle, et al., "The impact of rigidity and water exchange on the relaxivity of a dendritic MRI contrast agent," *Chemistry—A European Journal*, 8:1040-1048, 2002.

Reichert, et al., "Molecular Mechanics Investigation of Gadolinium(III) Complexes," *Inorganic Chemistry*, 35:7013-7020, 1996.

Rohrer, et al., "Comparison of magnetic properties of MRI contrast media solutions at different magnetic field strengths," *Investigative Radiology*, 40:715-724, 2005.

(Continued)

*Primary Examiner* — Michael G Hartley
*Assistant Examiner* — Jagadishwar Samala
(74) *Attorney, Agent, or Firm* — Parker Highlander PLLC

(57) ABSTRACT

In some aspects, the present invention provides novel ligands, which may be used to make novel dual-modality imaging agents, for example, for PET and MRI imaging. In further aspects, by the present disclosure also provides methods of use and methods of preparation of the novel ligands, metal complexes, and imaging agents thereof.

2 Claims, 5 Drawing Sheets

(56) References Cited

OTHER PUBLICATIONS

Santra, et al., "Synthesis and Characterization of Fluorescent, Radio-Opaque, and Paramagnetic Silica Nanoparticles for Multimodal Bioimaging Applications," *Advanced Materials*, 17:2165-2169, 2005.
Stasiuk and Long, "The ubiquitous DOTA and its derivatives: the impact of 1,4,7,10-tetraazacyclododecane-1,4,7,10-tetraacetic acid on biomedical imaging," *Chem. Commun.*, 49:2732-2746, 2013.
Venditto, et al., "PAMAM dendrimer based macromolecules as improved contrast agents," *Molecular Pharmaceutics*, 2:302-311, 2005.
PCT International Search Report and Written Opinion issued in International Application No. PCT/US2014/041230, mailed Oct. 17, 2014.
Viola-Villegas and Doyle, "The coordination chemistry of 1,4,7,10-tetraazachyclododecane-N,N',N'',N'''-tetraacetic acid ($H_4DOTA$): structural overview and analyses on structure-stability relationships," *Coordination Chemistry Reviews*, 253:1906-1925, 2009.

\* cited by examiner

FIGS. 4A-B

MOLECULAR DESIGN TOWARD DUAL-MODALITY PROBES FOR RADIOISOTOPE-BASED IMAGING (PET OR SPECT) AND MRI

The present application claims benefit of priority to U.S. Provisional Application Ser. No. 61/832,491, filed Jun. 7, 2013, the entire contents of which are hereby incorporated by reference.

BACKGROUND OF THE INVENTION

1. Field of the Invention

The present disclosure relates generally to the fields of diagnostic testing and imaging agents. The disclosure provides, for example, novel ligands that are useful for the preparation of novel dual-modality imaging agents for radioisotope-based imaging (PET or SPECT) and MRI, said novel imaging agents, and methods of synthesis and methods of use thereof.

2. Description of Related Art

Molecular imaging is used for visualizing biological targets and to understand their complexities for diagnosis and treatment purposes. Through an accurate and real-time imaging of biological targets, a thorough understanding of the fundamental biological processes can be gained leading to the successful diagnose of various diseases (Weissleder, 2006). Every imaging modality on its own fails to deliver all the necessary information about the biological target. Therefore, attempts are being made to combining two or more imaging modalities to overcome shortcomings present in single-modality system and to enhance the quality of the images to achieve proper visualization of the organs and a better reliability of the collected data. Multimodal imaging techniques are increasingly becoming popular and a variety of different combinations, such as MRI/optical, PET/near-infrared optical fluorescence (NIRF) and PET/CT and PET/MRI have been reported (Jennings, et al., 2009; Ntziachristos, et al., 2000; Beyer, et al., 2000; Murray, et al., 1993; Link and El-Sayed, 1999; Alivisatos, 1996). The fusion of PET and MRI is especially desirable as they mutually complement each other. While radioisotope-based techniques (PET or SPECT) are sensitive and therefore allow the study of processes at the molecular and cellular level in vivo, their spatial resolution is poor (≥1 cm for a clinical scanner) (Catana, et al., 2006; Chemy, 2006; Chemy, 2001). On the other hand, non radioisotope-based techniques such as MRI provide excellent spatial resolution (<0.1 cm), but require much larger amounts of contrast agent (Caravan, et al., 1999; Raymond and Pierre, 2004; Seo, et al., 2006). The need to overcome their respective disadvantages drives the ongoing efforts to develop dual modality imaging instruments and agents so that the strengths of these techniques can be synergistically combined to provide accurate physiological and anatomical information.

To take advantage of bimodal PET (or SPECT)/MRI imaging, a dual modality agent with a "single pharmacological behavior" is desirable, which that can combine the high sensitivity of PET and the high resolution of MRI. For instance, a MRI/PET probe should enable the increased accuracy of probe co-location and cross-validation of MRI and PET agents in target regions of interest (two measures of one event). While MRI scan can provide the exact location of the probe, motion artifact correction, and PET partial volume correction, the PET part can afford better image quantification for higher detection sensitivity and more accurate molecular signature changes over the course of treatment. In addition, the perfect collocation of MRI and PET signals would enable the co-registration of MRI and PET images. Given the proton MRI contrast can be viewed as the ups and downs of the proton ocean, a co-localized PET signal distinct from the background ocean could make the MRI contrast more identifiable, which further improves the MRI sensitivity.

Gadolinium is a known and well characterized $T_1$ contrast agent with useful and important physical properties for use in MRI imaging agents. Unfortunately, this ion is highly toxic in a "free" state, and hence it is always used as a thermodynamically stable and kinetically inert complex. Linear polyamine diethylenetriaminepentaacetic acid (DTPA) or polyazamacrocycle 1,4,7,-10-tetraazacyclododecane-1,4,7,10-tetraacetic acid derivatives (DOTA) with coordinating acetate arms have been commercially employed as they form sufficiently stable Gd(III) complexes. Unfortunately, these low molecular weight contrast agents are nonspecific, undergo rapid renal excretion and extravasation, and they have relatively low relaxivity. To compensate for the low signal enhancement generated by DTPA and DOTA gadolinium complex, most targeted gadolinium compounds have relied on the development of nano platforms that can carry a high payload of gadolinium, by which the longitudinal relaxivities ($r_1$) per gadolinium can be further enhanced as the rotational correlation time increases with the molecular weight. A wide range of macromolecules and other nanoparticulate systems have been tested as platforms for gadolinium labeling, including dendrimers, (Boswell, et al., Kobayashi and Brechbiel, 2005; Langereis, et al., 2006a; Langereis, et al., 2006b; Langereis, et al., 2007; Ruovský, et al., 2006; Bolskar, 2008; Zhu, et al., 2008) polymers, (Duarte, et al., 2001) emulsions, (Morawski, et al., 2004) silica nanoparticles, (Lin, et al., 2004; Rieter, et al., 2007a; Rieter, et al., 2007b; Santra, et al., 2005) and vesicles (Cheng and Tsourkas, 2008; Hak, et al., 2009; Terreno, et al., 2008; Unger, et al., 1989). Some of these agents have relaxivities on the order of 105 to 106 $mM^{-1} s^{-1}$ per nanoparticle (Morawski, et al., 2004; Santa, et al., 2005; Cheng and Tsourkas, 2008). Of all the systems, dendrimers have a specified molecular structure and formula and have been used extensively. PAMAM is the favored choice in dendrimers but Gd-PAMAM complexes rarely give an ionic relaxivity greater than 11 $mM^{-1} S^{-1}$ (Venditto, et al., 2005; Kobayashi and Brechbiel, 2003) Researchers at Schering AG (Berlin, Germany) developed another class of dendritic contrast agents: Gadomer-17, a polylysine-based contrast agent (MW 17,453) with 24 gadolinium-1,4,7,10-tetrakis(carboxymethyl) cyclododecane (Gd-DOTA) complexes (Dong, et al., 1998; Nicolle, et al., 2002). Gadomer-17 has an ionic relaxivity of 17.3 $mM^{-1} s^{-1}$ (20 MHz, 39° C.).

Numerous nanoparticle based MRI/PET agent have been reported and have shown considerable promise. These nanoparticles show a high relaxivity (Morawski, et al., 2004; Santa, et al., 2005; Cheng and Tsourkas, 2008) relative to other MRI/PET agents. However, using nanoparticle for MRI/PET probe development presents its own challenges. Often, nanoparticle constructs used for MRI/PET have questionable in vivo stability or integrity. Clinically used contrast agents used are desired to have rapid diffusion (short distribution half-life $t_{\alpha 1/2}$) relatively long blood circulation time (long elimination half-life $t_{\beta 1/2}$), and little nonspecific accumulation in the body (renal clearable) after systemic administration. These specific pharmacokinetic features may ensure the success of clinical imaging processes but also may minimize the potential health hazards caused by the introduction of contrast agents. Most nanoparticle are unsuitable for clinical use as reticuloendothelial system (RES) organs often rapidly sequester these nanostructures, resulting in slow RES clearance processes and potential health hazards (Cheng, et al., 2011; Chen, et al., 2005; Gao, et al., 2004). These limitations in pharmacokinetics of nanoparticles significantly hamper their clinical applications. Thus, it is desirable to develop probes that possess improved distribution properties as well as improved pharmacokinetic properties.

SUMMARY OF THE INVENTION

In some aspects, the present invention provides ligands that may be used to form imaging agents, including, for example, novel gadolinium and/or gallium complexes. In some aspects the present invention provides a compound of the formula:

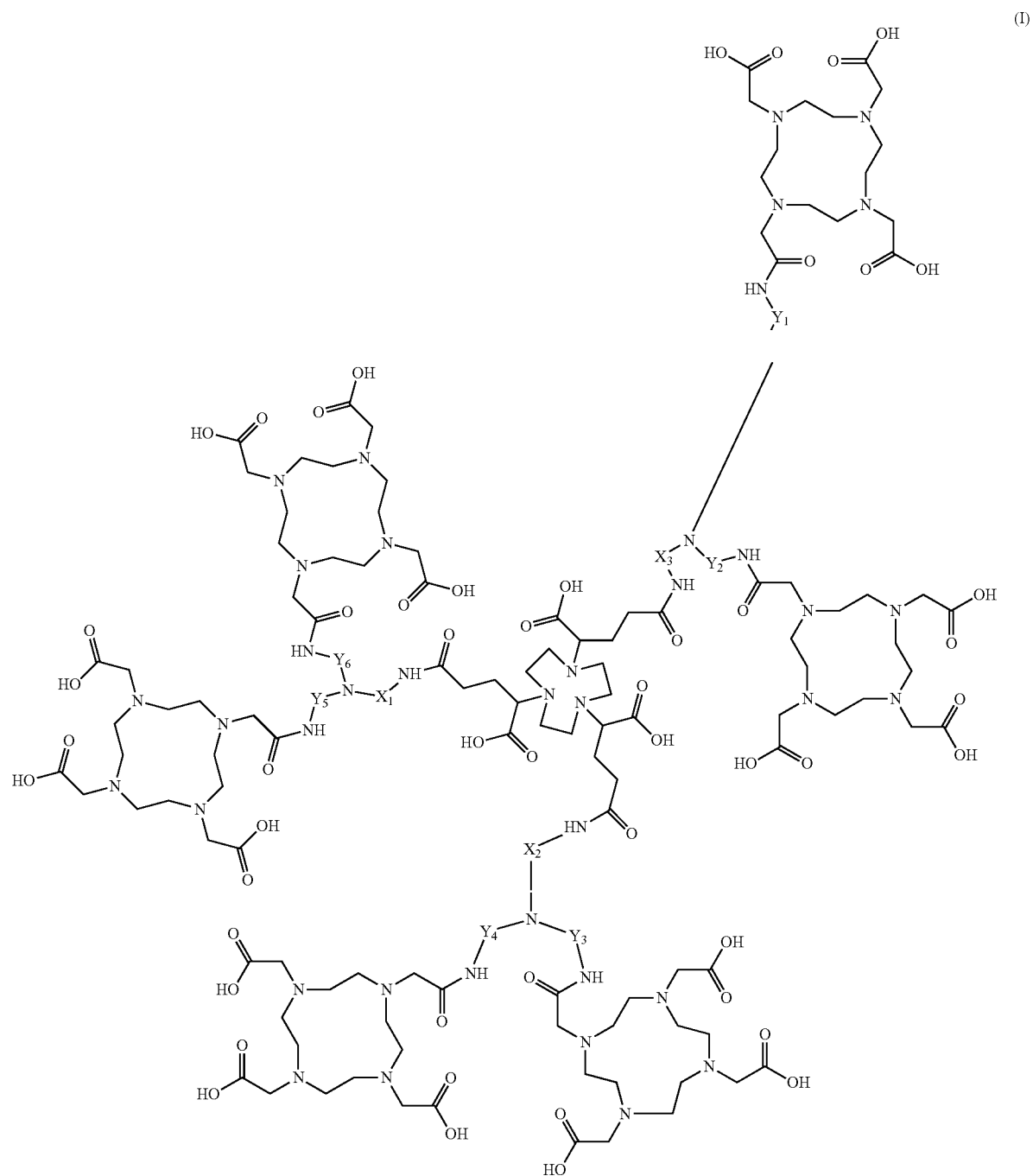

(I)

wherein: $X_1$, $X_2$, and $X_3$ are each independently alkanediyl$_{(C \leq 12)}$, alkenediyl$_{(C \leq 12)}$, alkynediyl$_{(C \leq 12)}$, arenediyl$_{(C \leq 12)}$, heteroarenediyl$_{(C \leq 12)}$, alkoxydiyl$_{(C \leq 12)}$, alkylaminodiyl$_{(C \leq 12)}$, or a substituted version of any of these groups; or an amino acid residue, an amino acid residue linked to a targeting moiety, a PEG linker comprising between 2 and 200 repeating units; and $Y_1$, $Y_2$, $Y_3$, $Y_4$, $Y_5$, and $Y_6$ are each independently alkanediyl$_{(C \leq 12)}$, alkenediyl$_{(C \leq 12)}$, alkynediyl$_{(C \leq 12)}$, arenediyl$_{(C \leq 12)}$, heteroarenediyl$_{(C \leq 12)}$, alkoxydiyl$_{(C \leq 12)}$, alkylaminodiyl$_{(C \leq 12)}$, or a substituted version of any of these groups; or an amino acid residue, an amino acid residue linked to a targeting moiety, a PEG linker comprising between 2 and 200 repeating units; or a metal complex or salt thereof. In some embodiments, independently 1-5; or a metal complex or salt thereof. In some embodiments, $X_1$, $X_2$, and $X_3$ are each an amino acid residue. In some embodiments, $X_1$, $X_2$, and $X_3$ are each a lysine. In some embodiments, $X_1$, $X_2$, and $X_3$ are each an amino acid residue linked to a targeting moiety. In some embodiments, $X_1$, $X_2$, and $X_3$ are each a lysine linked to a targeting moiety. In some embodiments, the targeting moiety is a cyclic RDGyK peptide. In some embodiments, the cyclic RDGyK peptide comprises a linker with a mercapto group. In some embodiments, the cyclic RDGyK peptide further comprises a PEG linker comprising between 2 and 200 repeating units. In some embodiments, the PEG linker comprises between 2 and 50 repeating units. In some embodiments, the PEG linker comprises between 2 and 20

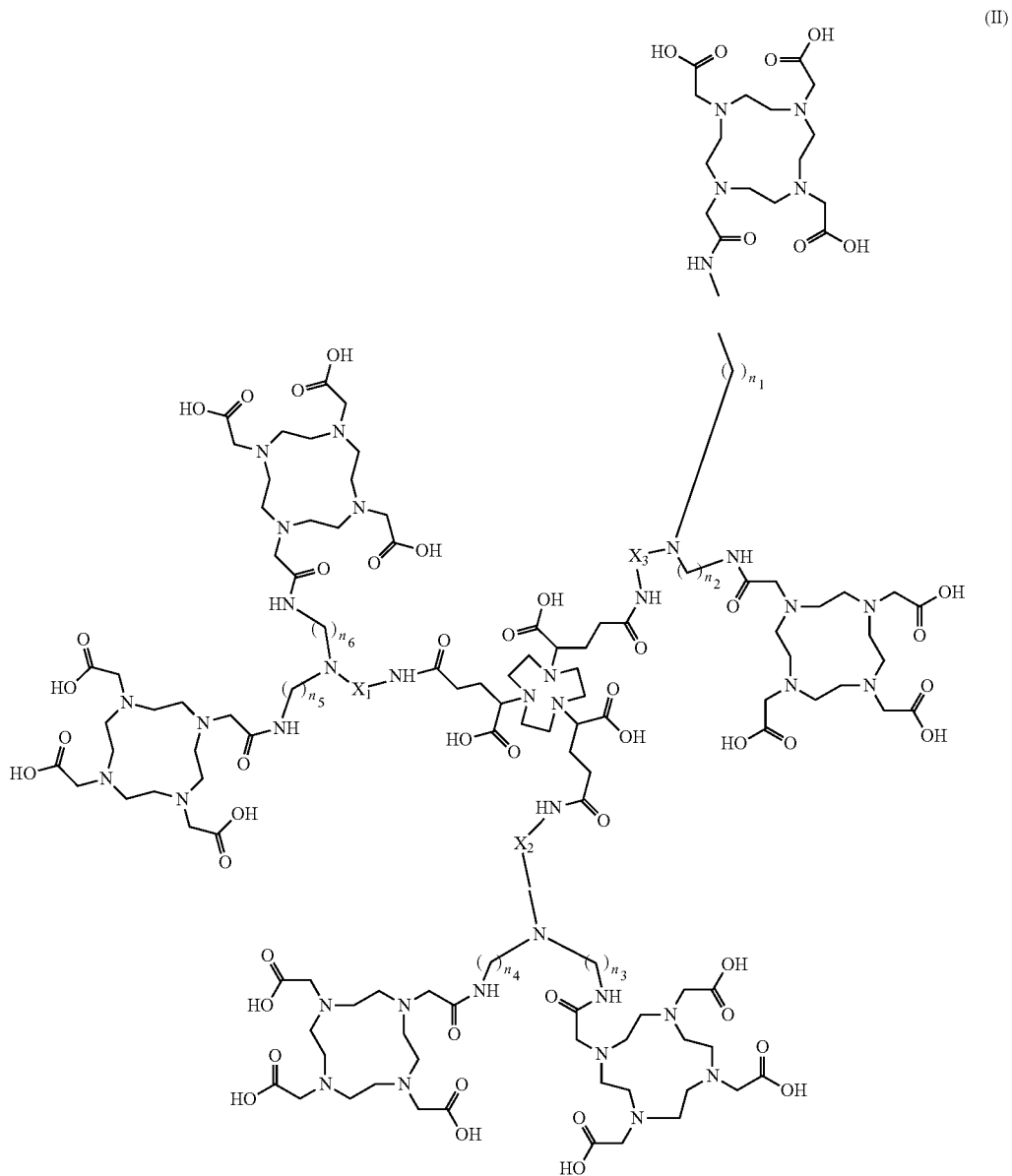

wherein: $X_1$, $X_2$, and $X_3$ are each independently selected from an amino acid residue or an amino acid residue linked to a targeting moiety; and $n_1$, $n_2$, $n_3$, $n_4$, $n_5$, and $n_6$ are each repeating units. In some embodiments, the amino acid residue linked to a targeting moiety is further defined by the structure:

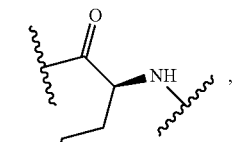
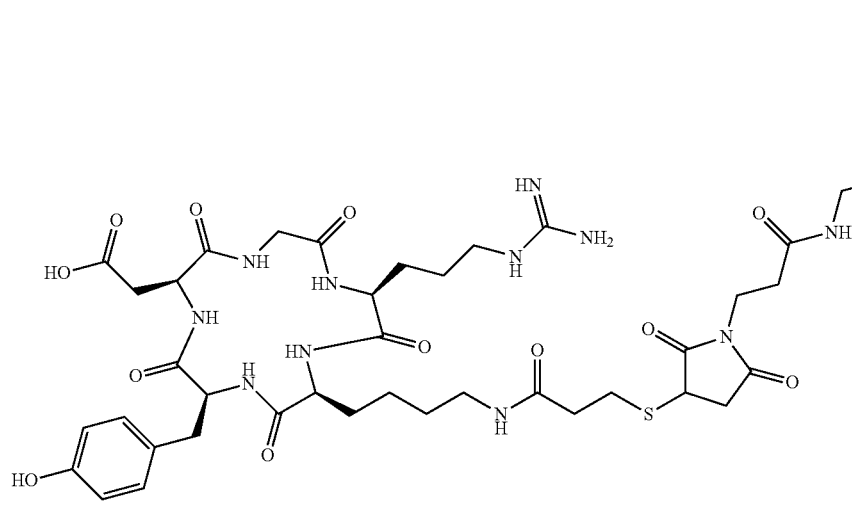
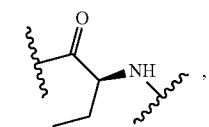
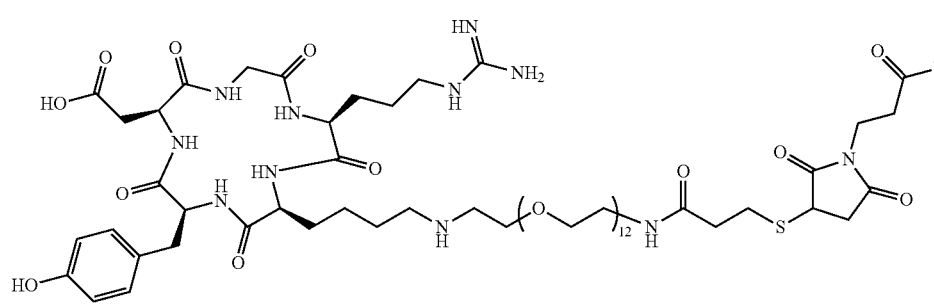
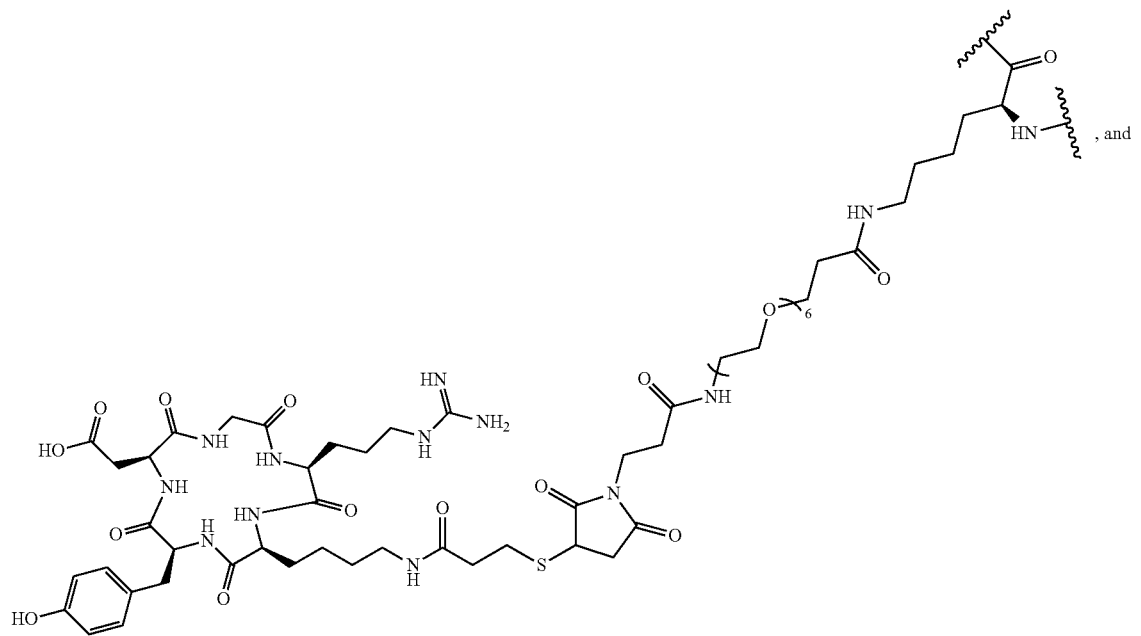

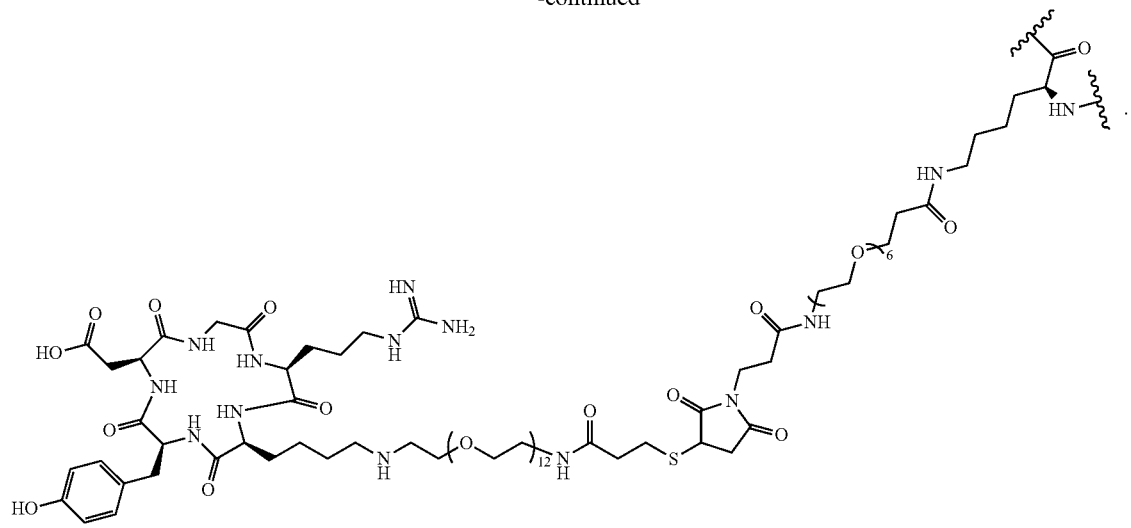
In some embodiments, $n_1$, $n_2$, $n_3$, $n_4$, $n_5$, and $n_6$ are each 3.
In some embodiments, the compound is further defined by the formula:
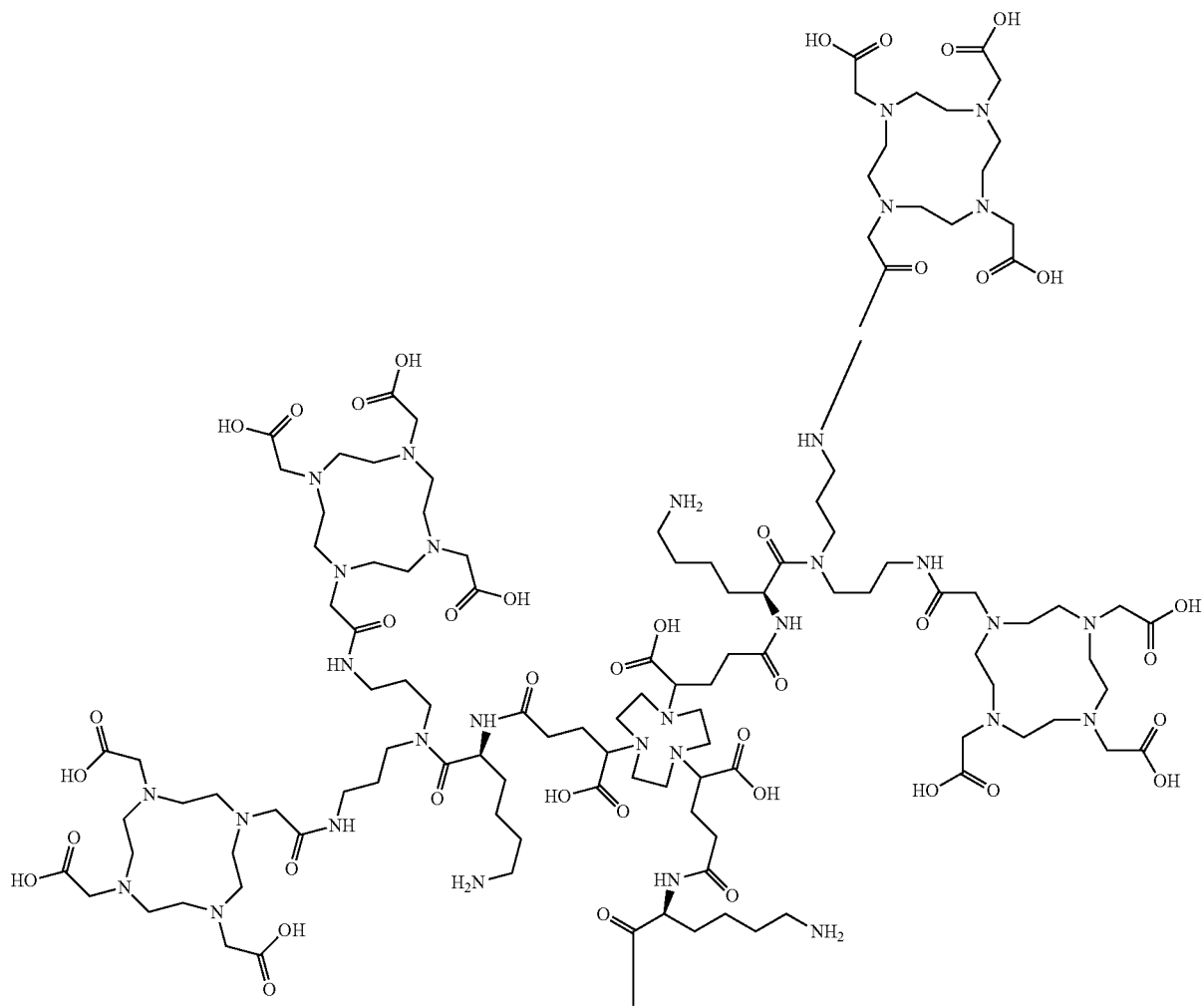

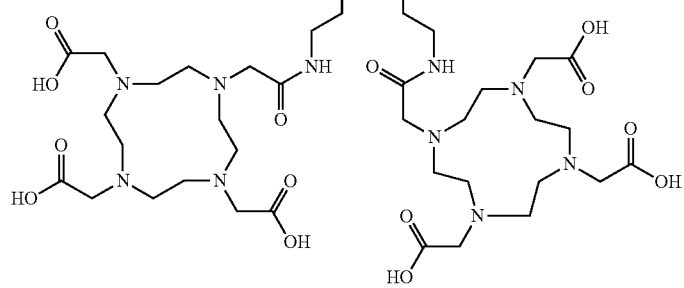
or a metal complex or salt thereof. In some embodiments, the compound is further defined by the formula:
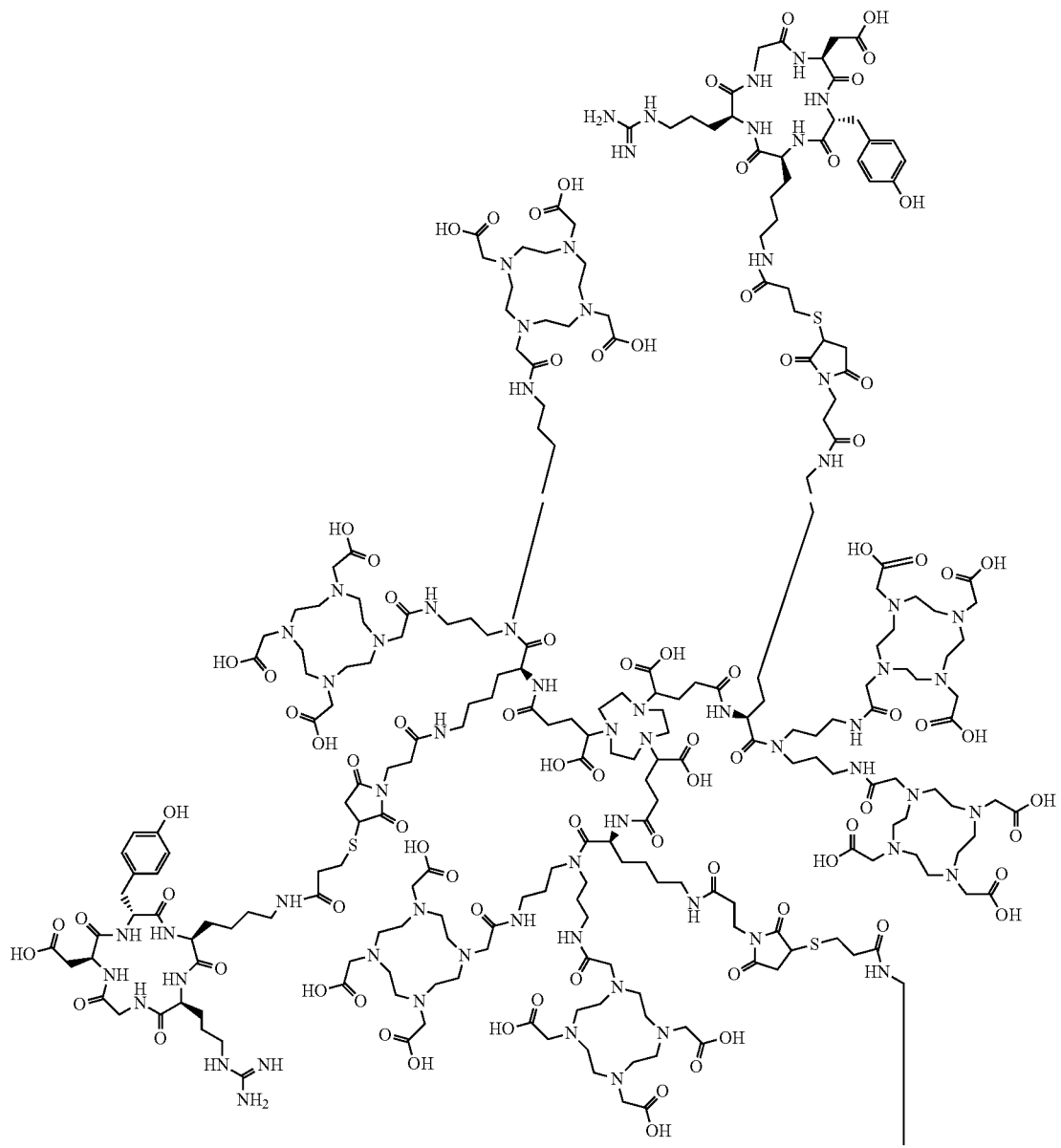

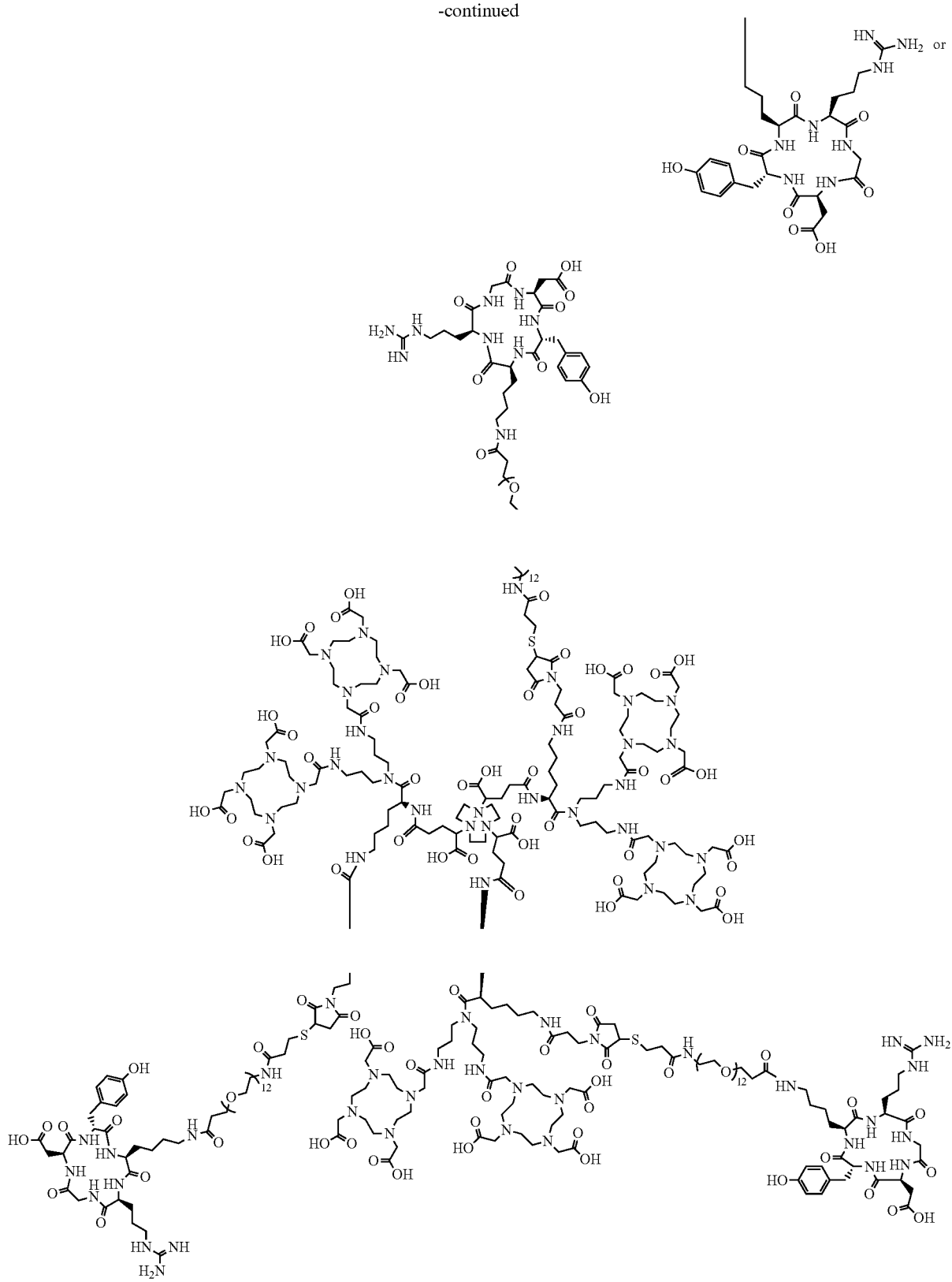
or a metal complex or salt thereof. In other embodiments, the compound is a metal complex, wherein the metal ion is gallium, gadolinium or a mixture of both. In other embodiments, the compound is further defined as:

(III)
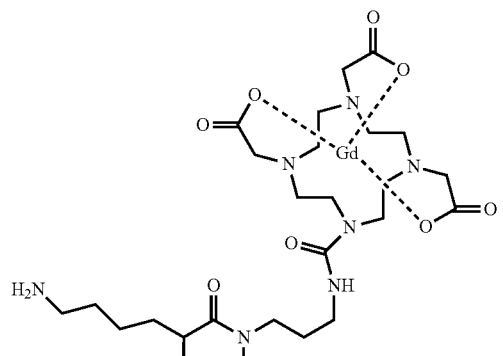
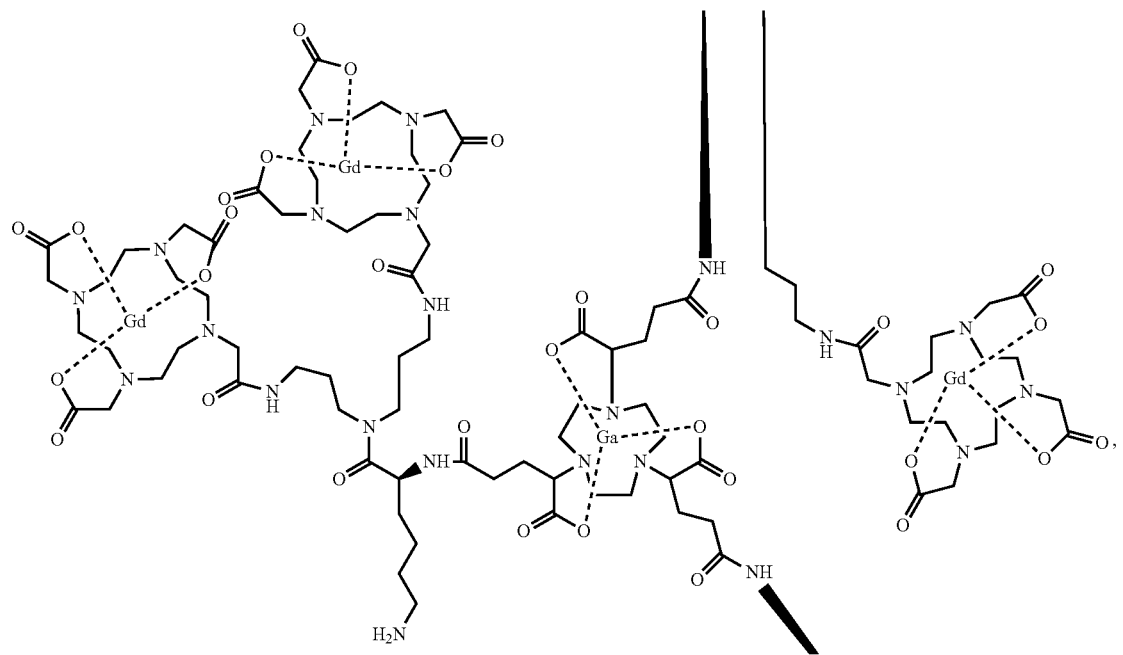
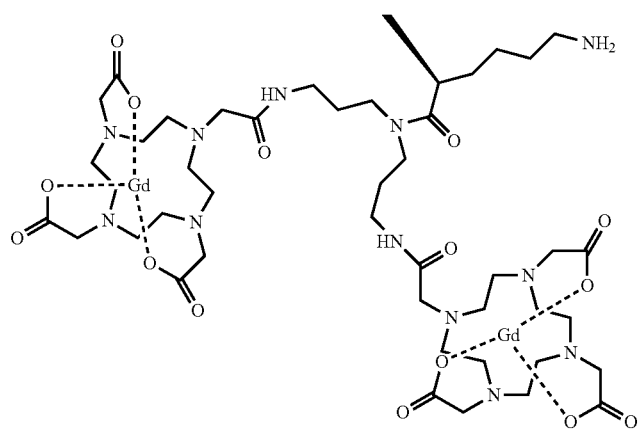

or a salt thereof. In some embodiments, the compound is further defined as:
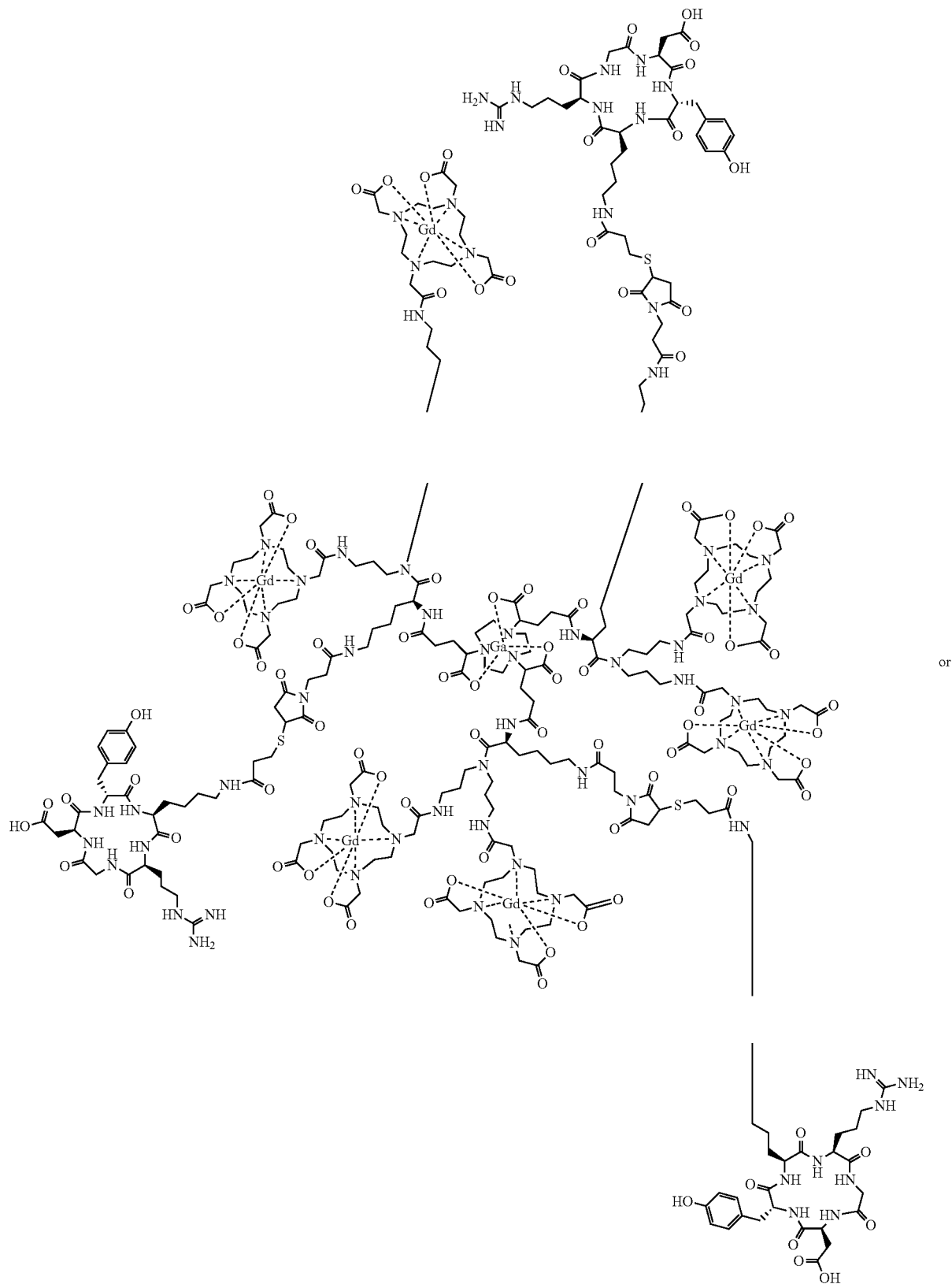
or -continued
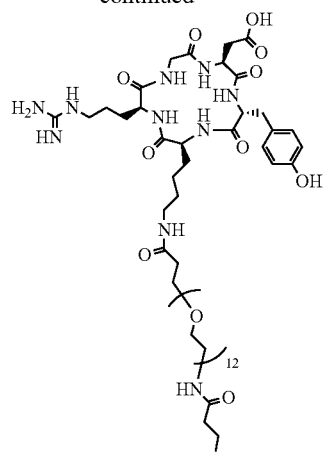
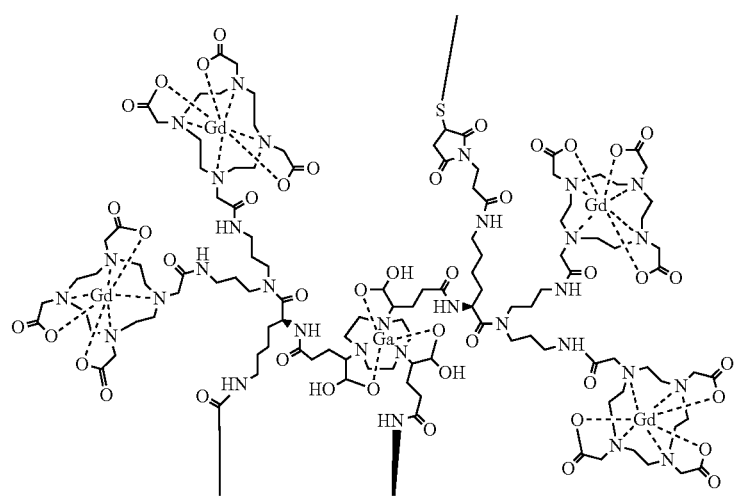
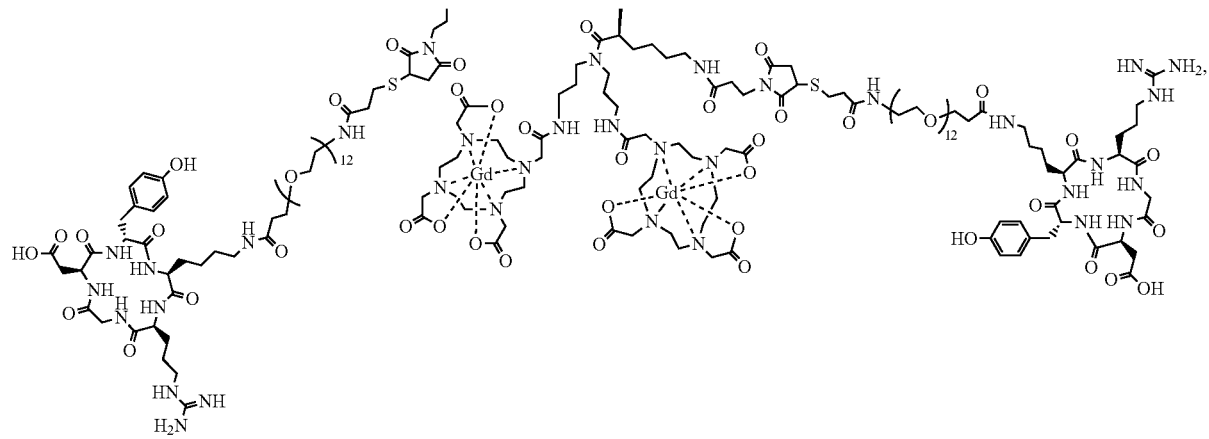

or a salt thereof. In other embodiments, the compound is further defined as:
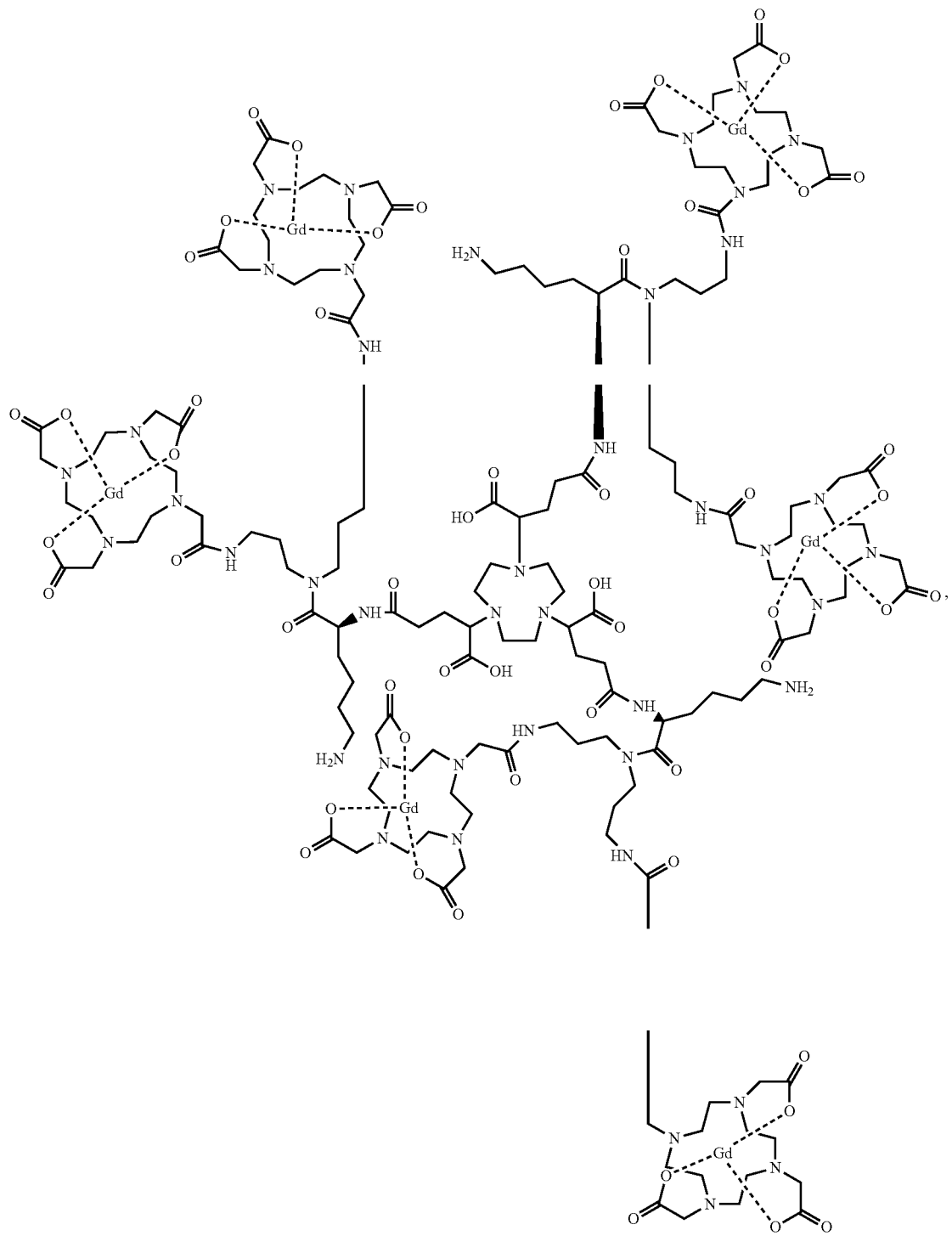
(IV)
or a salt thereof. In some embodiments, the compound is further defined as:

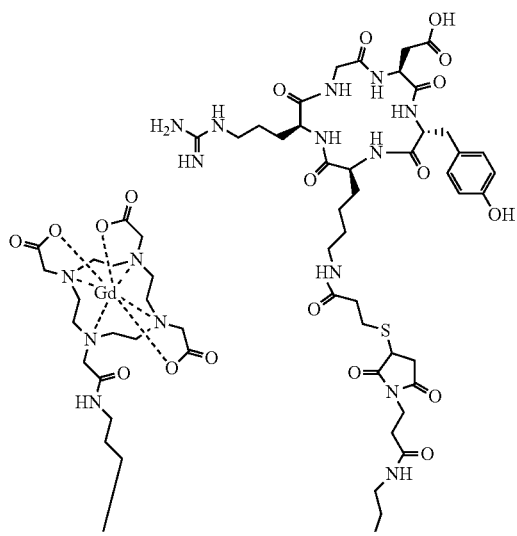
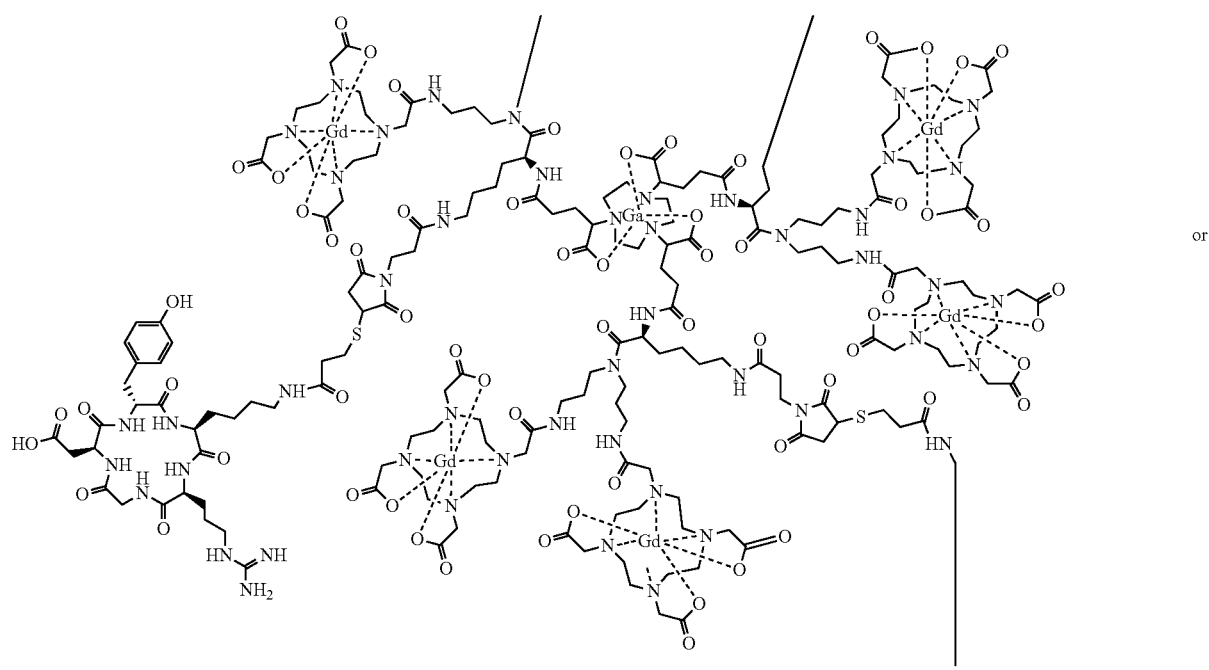
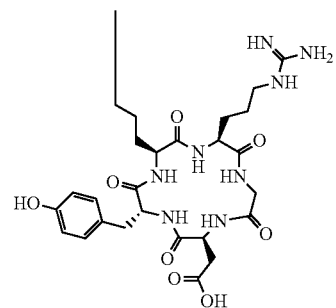

-continued
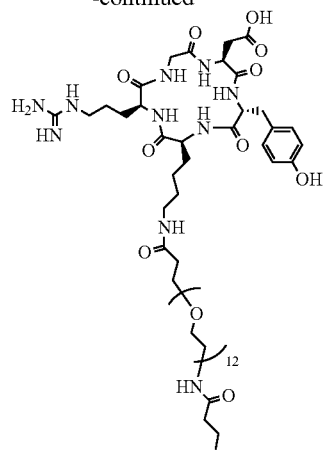
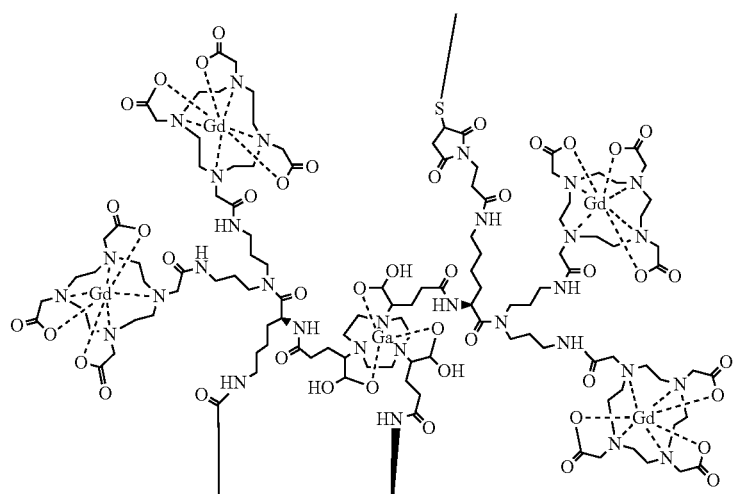
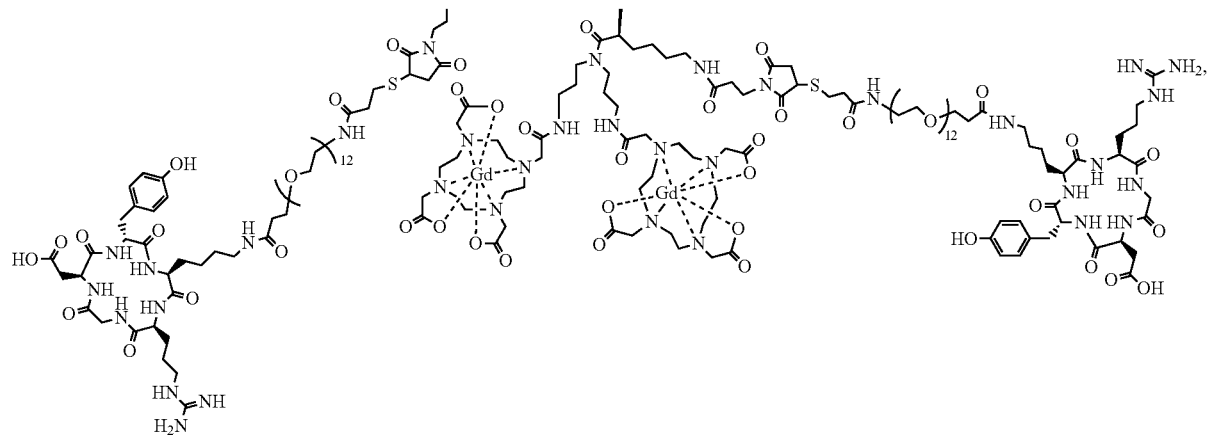
or a salt thereof.
In other aspect, the present invention provides compounds of the formula:

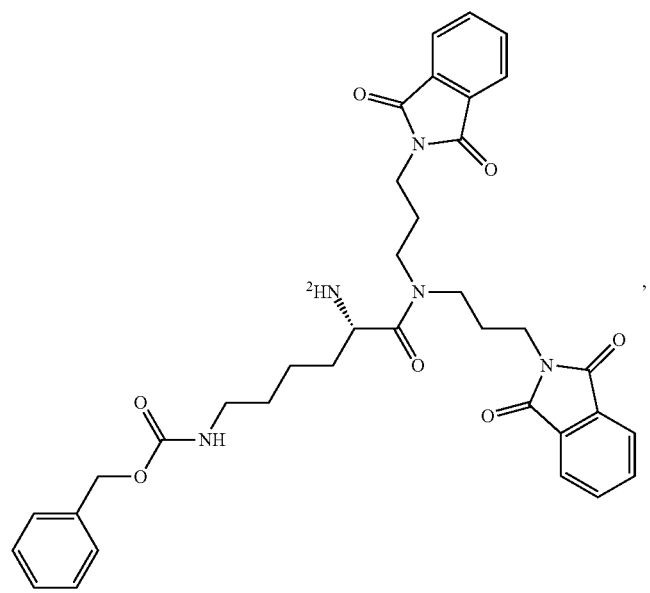
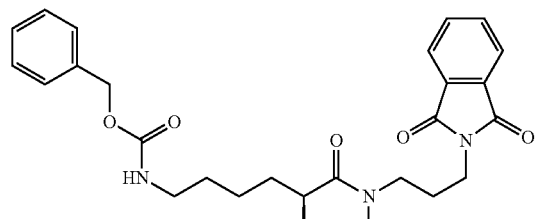
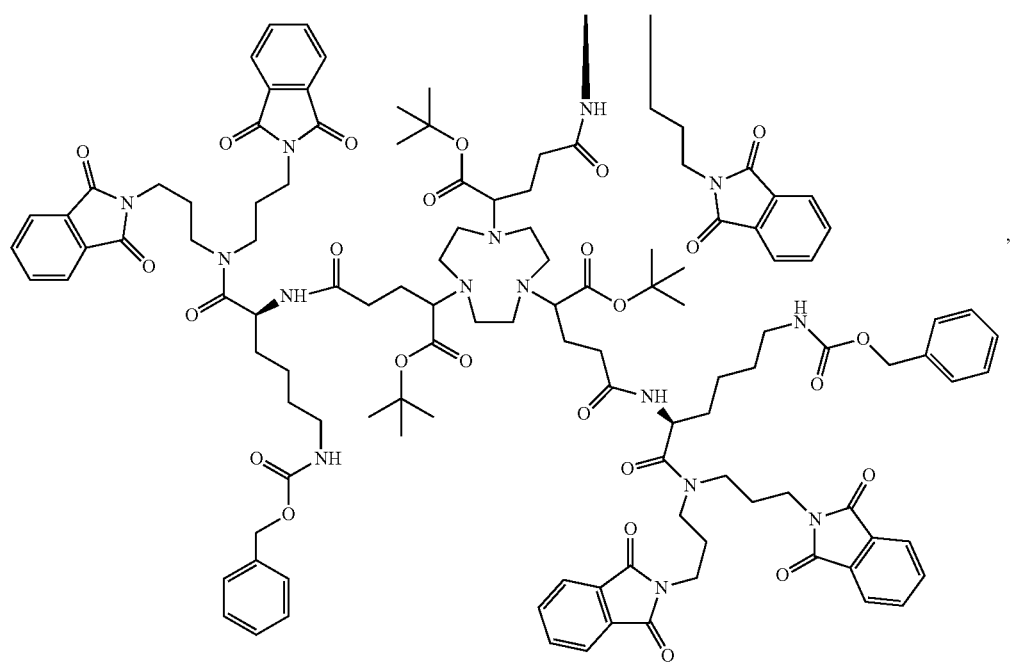

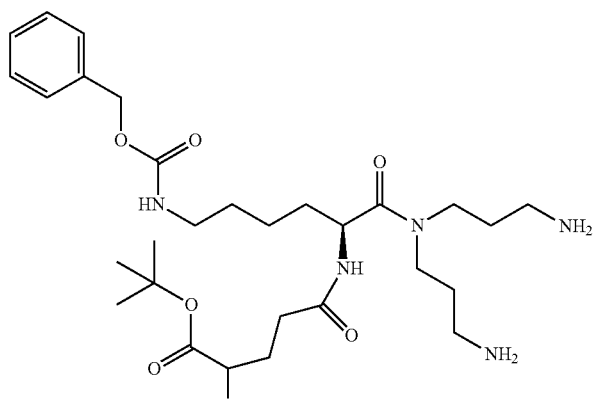
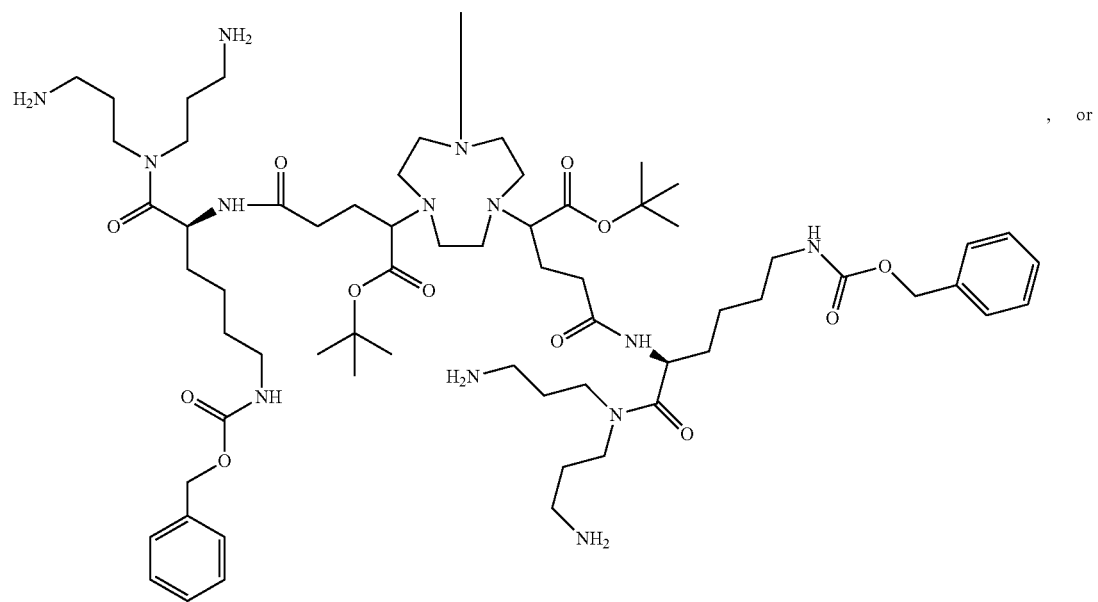, or
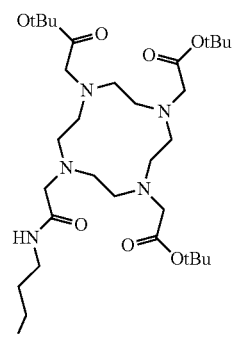

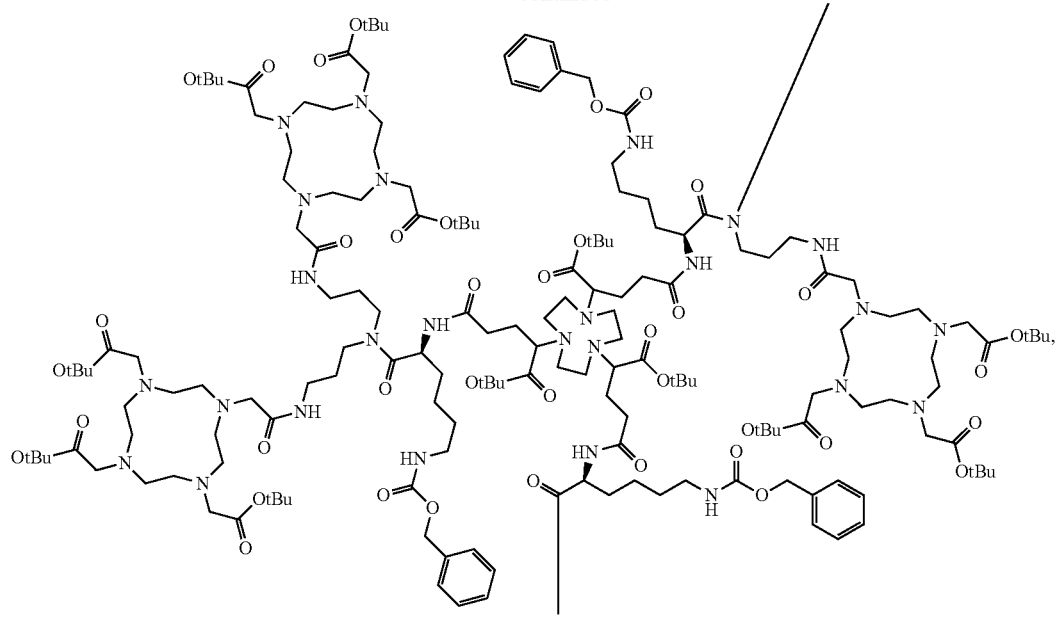
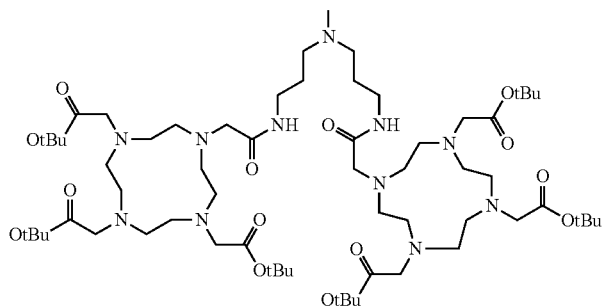
or a salt thereof. In some aspects, the present disclosure provides a compound of the formula:
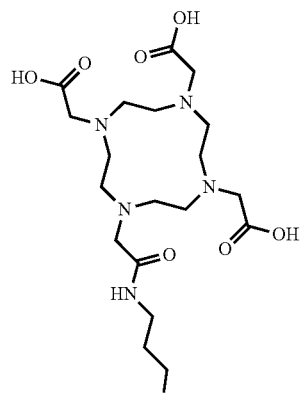

33    34
-continued
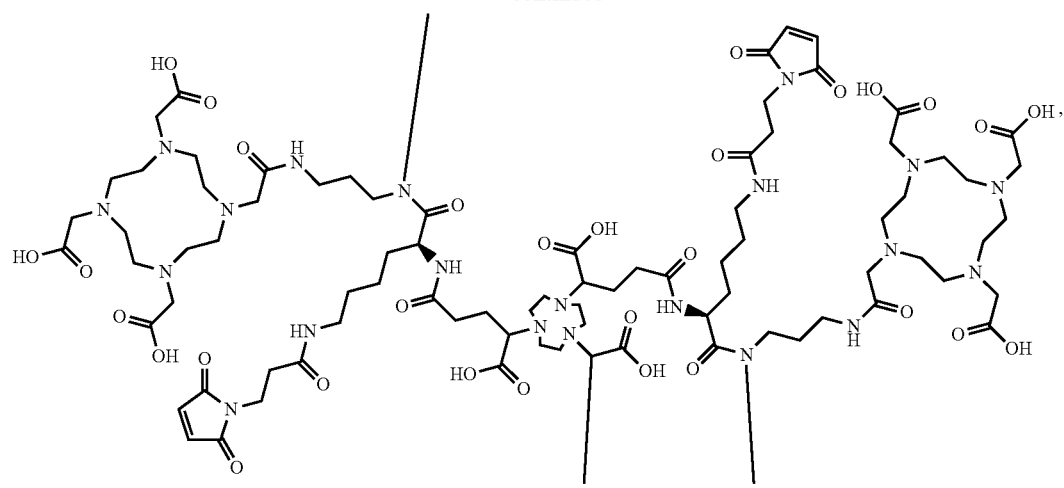
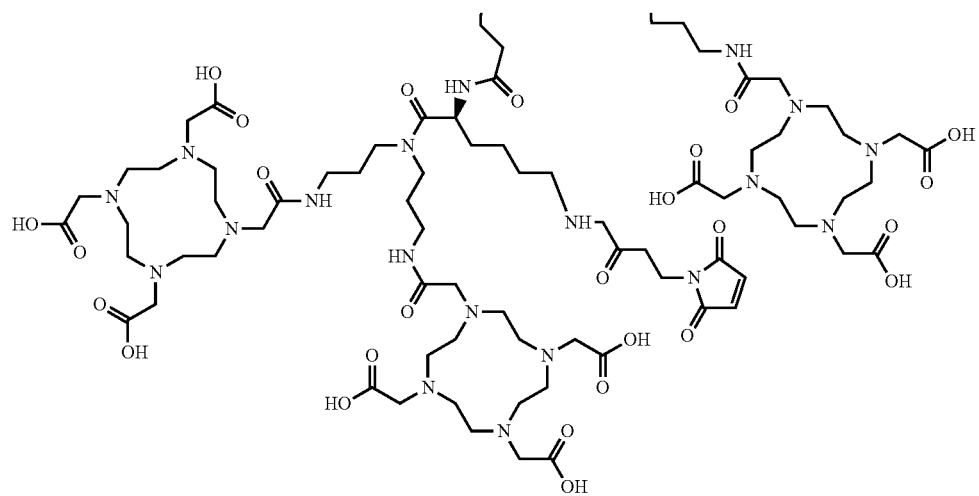
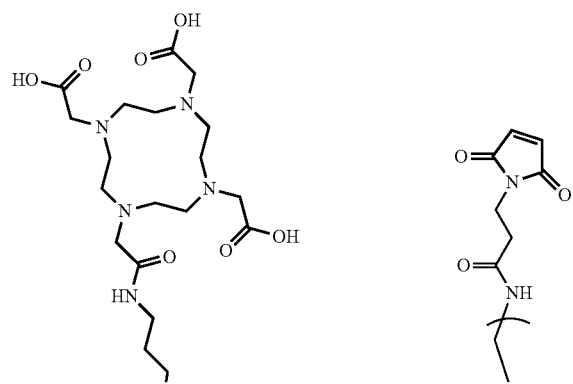

-continued

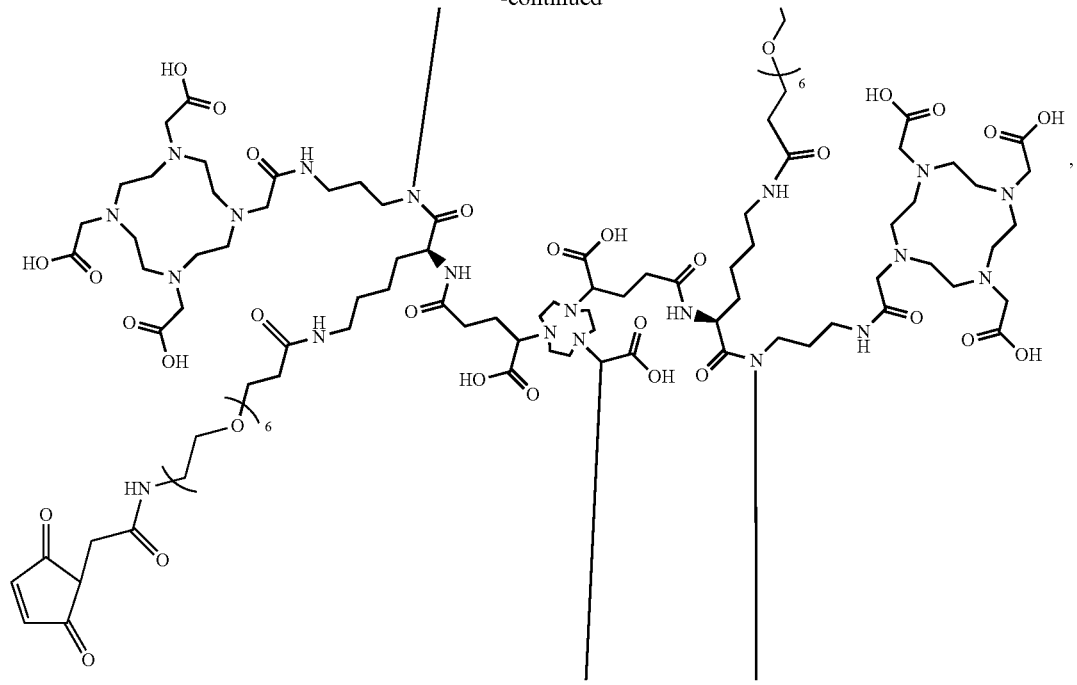

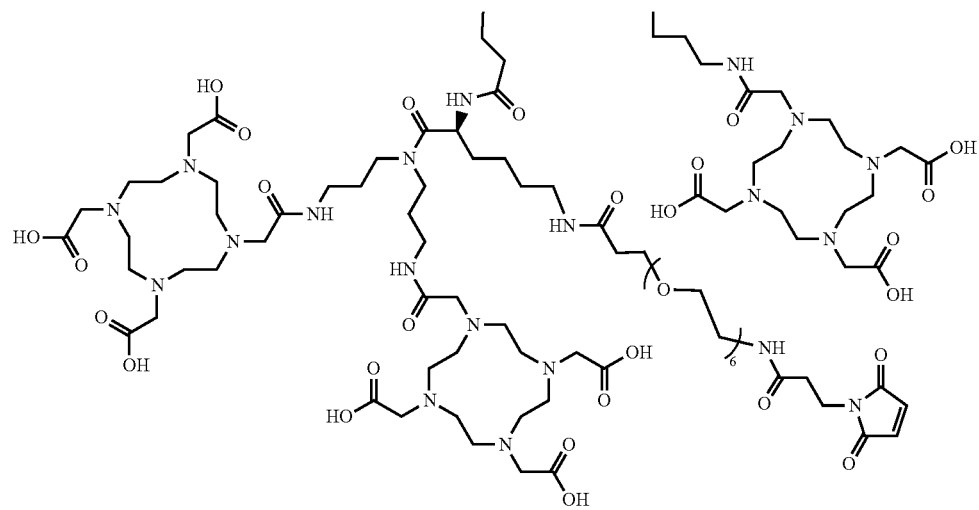

or a salt thereof. In some embodiments, the salt is a chloride salt. In some embodiments, the salt is a pharmaceutically acceptable salt.

In another aspect, the present invention provides, a composition comprising a compound of the present invention and a pharmaceutically acceptable carrier. In some embodiments, the composition is formulated as a unit dose form in an amount sufficient to image a patient when administered thereto.

In yet another aspects, the present invention provides a compound of the formula:

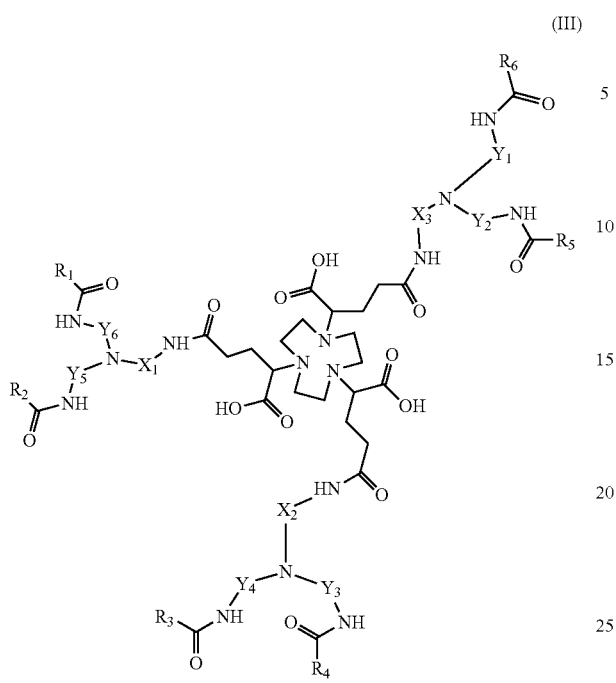

(III)

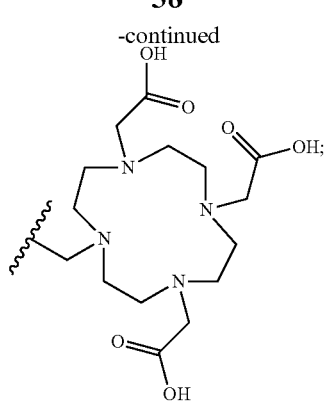

wherein: $R_1$, $R_2$, $R_3$, $R_4$, $R_5$, and $R_6$ are each independently selected from

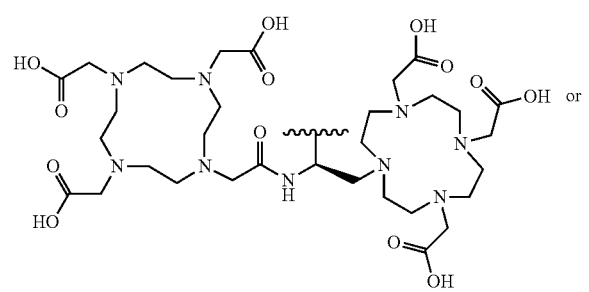

$X_1$, $X_2$, and $X_3$ are each independently alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, alkoxydiyl$_{(C\leq 12)}$, alkylaminodiyl$_{(C\leq 12)}$, or a substituted version of any of these groups; or an amino acid residue, an amino acid residue linked to a targeting moiety, a PEG linker comprising between 2 and 200 repeating units; $Y_1$, $Y_2$, $Y_3$, $Y_4$, $Y_5$, and $Y_6$ are each independently alkanediyl$_{(C\leq 12)}$, alkenediyl$_{(C\leq 12)}$, alkynediyl$_{(C\leq 12)}$, arenediyl$_{(C\leq 12)}$, heteroarenediyl$_{(C\leq 12)}$, alkoxydiyl$_{(C\leq 12)}$, alkylaminodiyl$_{(C\leq 12)}$, or a substituted version of any of these groups; or an amino acid residue, an amino acid residue linked to a targeting moiety, a PEG linker comprising between 2 and 200 repeating units; and provided that all of $R_1$, $R_2$, $R_3$, $R_4$, $R_5$, and $R_6$ are not

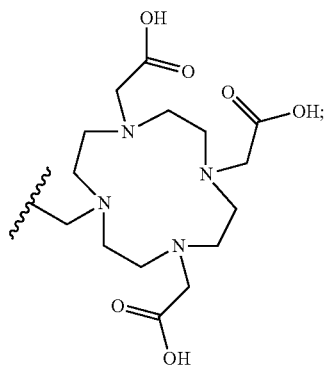

or a metal complex or salt thereof. In some embodiments, the compound is further defined as:

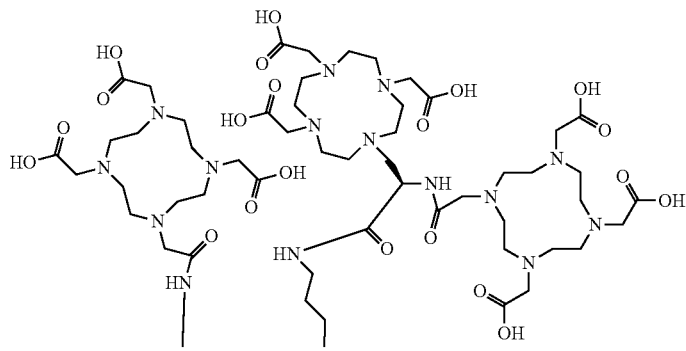

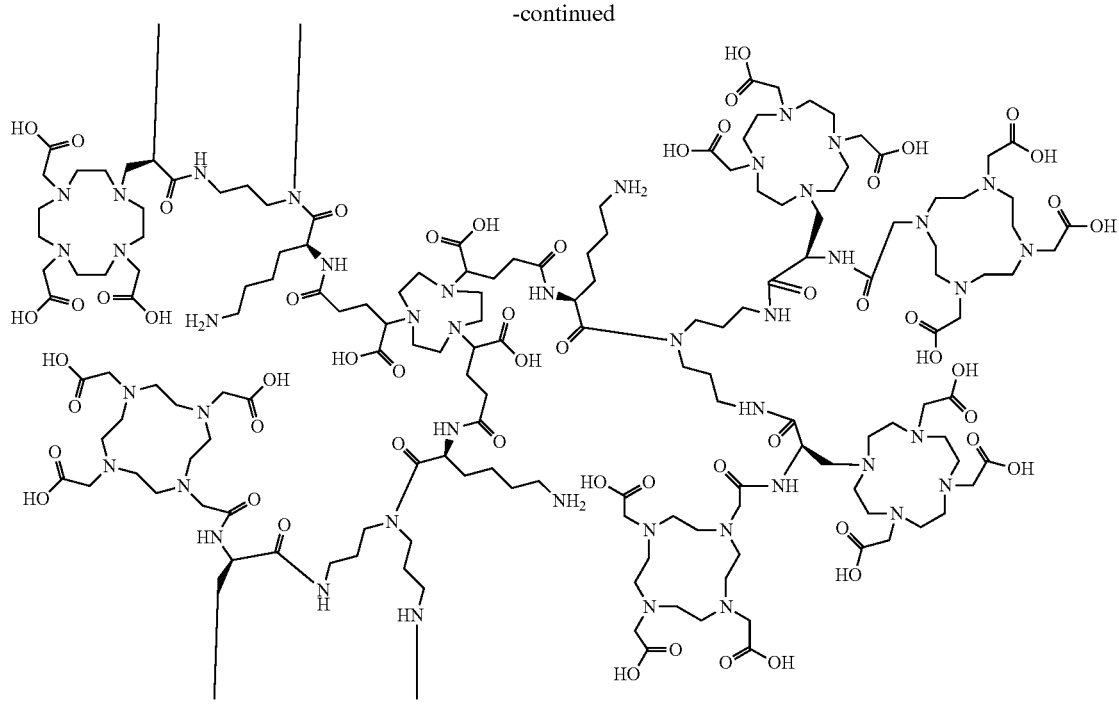

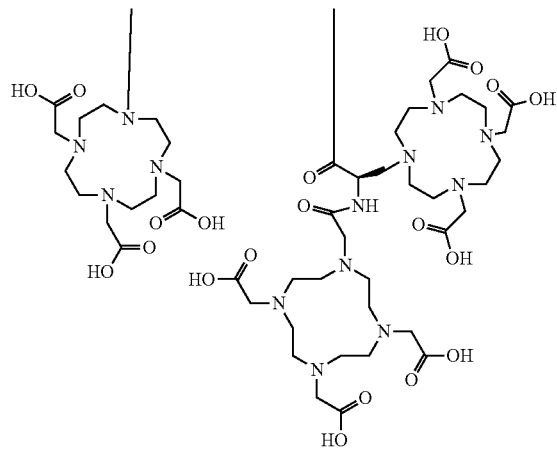

or a metal complex or salt thereof.

In another aspect, the present invention provides a method of imaging a patient comprising the steps of a) administering to a patient a compound or composition of the present invention; b) collecting imaging scans of the patient; and c) analyzing the results of the imaging scans. In some embodiments, the imaging of the patient comprises collecting MRI, SPECT, or PET images of the patient. In some embodiments, the method further comprises a second step of collecting imaging scans of the patient. In other embodiments, the imaging of the patient comprises collecting MRI and either PET or SPECT images of the patient. In some embodiments, the MRI and either PET or SPECT images are obtained sequentially. In other embodiments, the MRI and either PET or SPECT images are obtained simultaneously. In some embodiments, the patient is a mammal. In other embodiments, the patient is a human.

In one aspect, the present invention provides a method of preparing a dual modality imaging complex comprising reacting a compound of the formula:

(V)
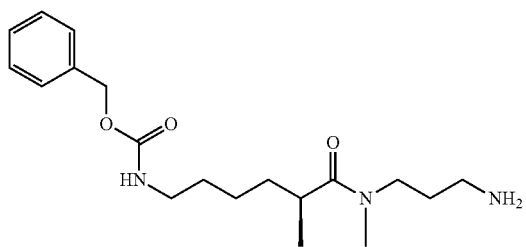
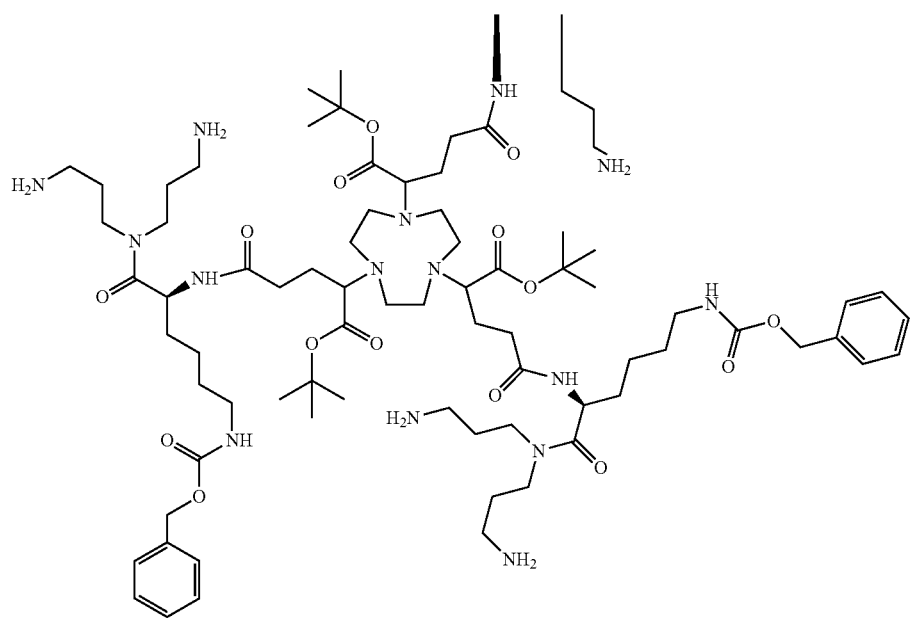
with a compound of the formula:
(VI)
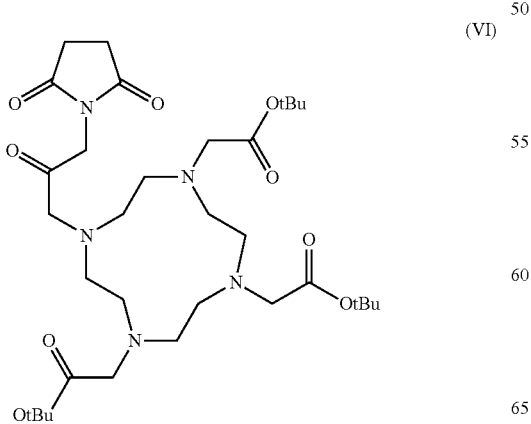

to produce a compound of the formula:
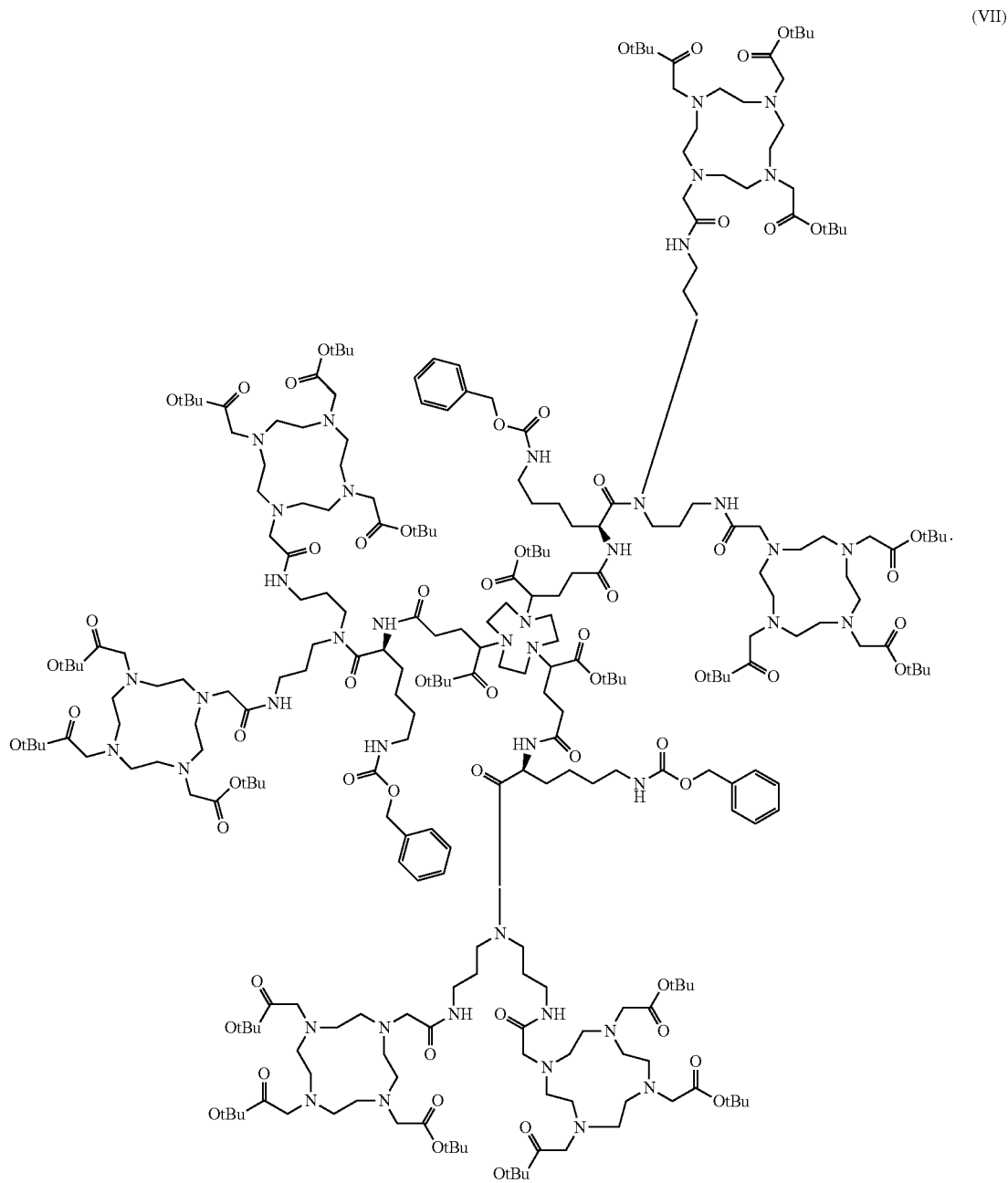
(VII)
In some embodiments, the method further comprising reacting a compound of the formula:
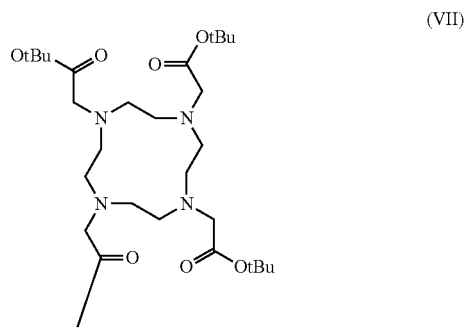
(VII)

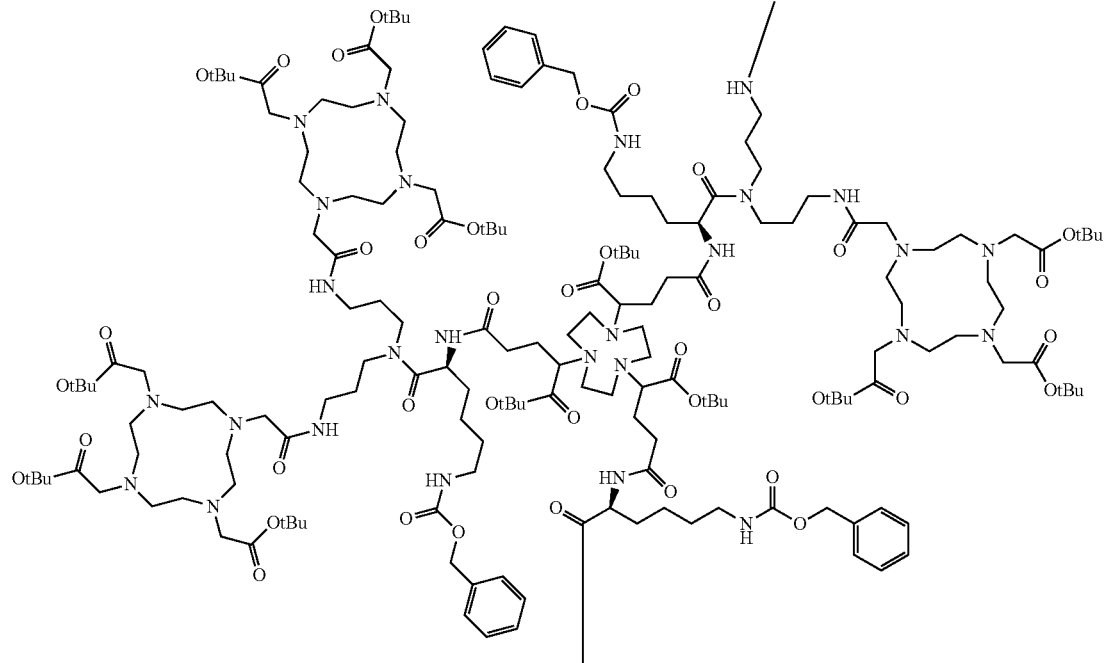
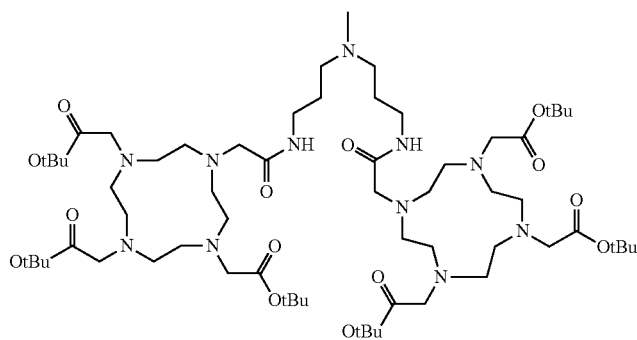
with one or more acids to produce a compound of the formula:
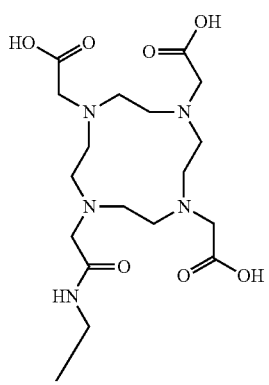
(II)

-continued
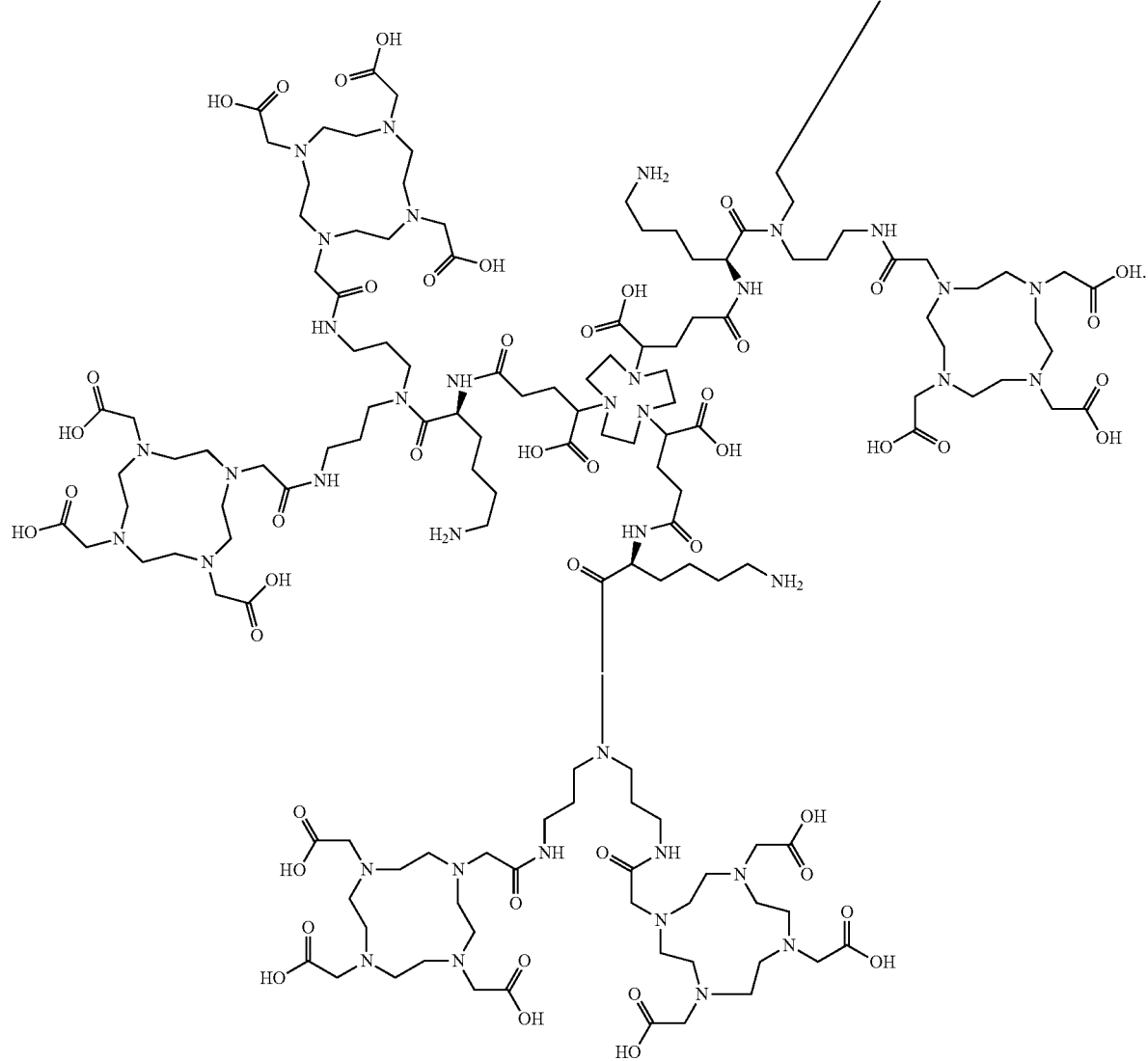
In some embodiments, the acid is 30% HBr in AcOH.
In yet another aspect, the present invention provides a method of preparing a compound comprising reacting a compound of the formula:
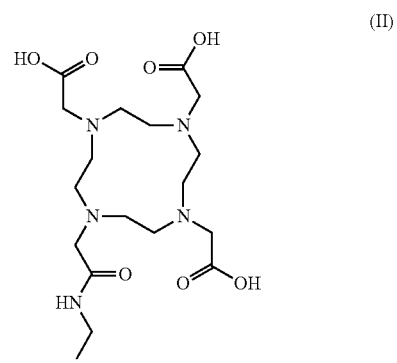
(II)

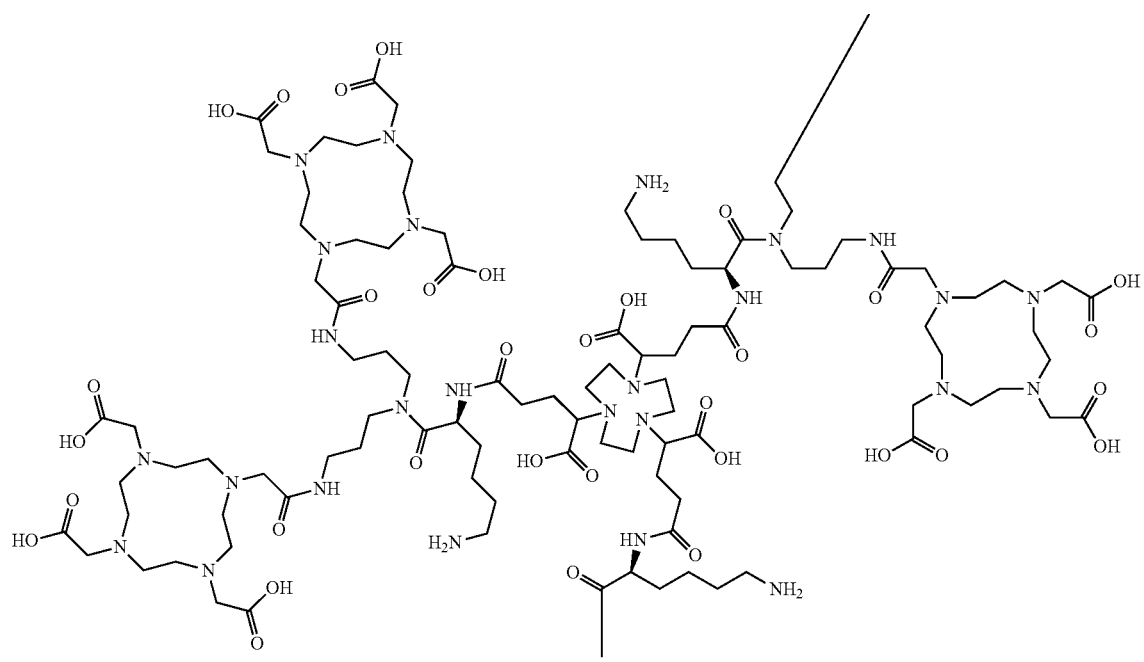
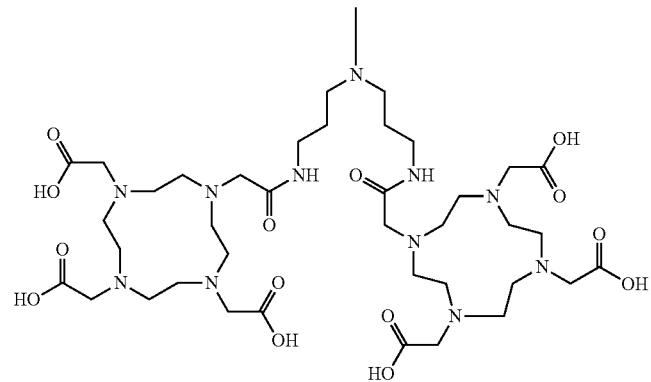
with an aqueous solution of a gadolinium(III) salt to form a compound of the following formula:

(IV)

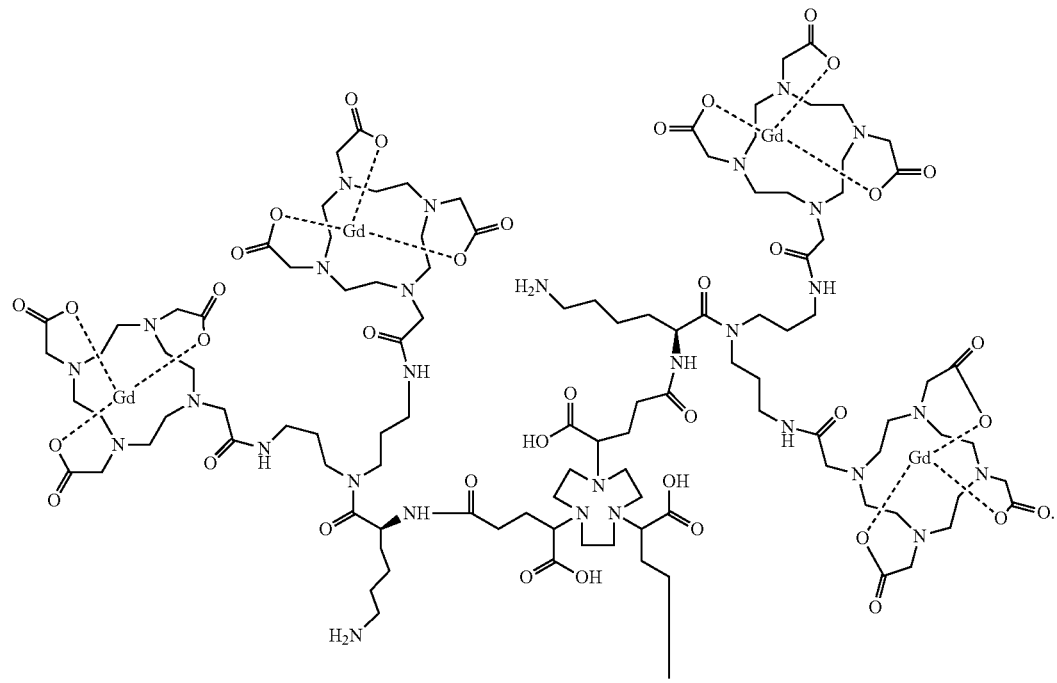

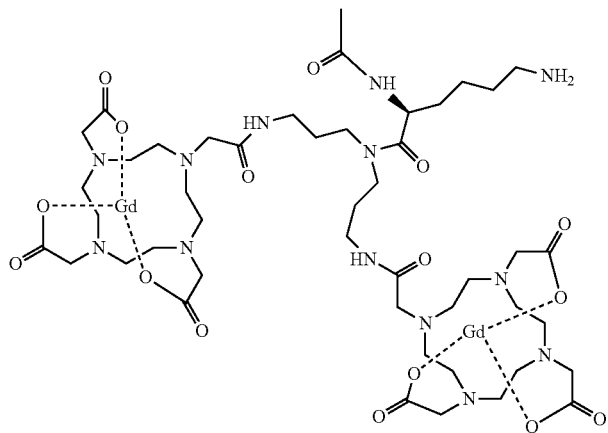

In some embodiments, the pH of the solution is brought to pH 7 before the addition of the metal salt. In some embodiments, the gadolinium(III) salt is gadolinium(III) chloride. In some embodiments, the pH of the solution is adjusted to pH 8 to precipitate any excess gadolinium(III) salt. In some embodiments, the pH of the solution is adjusted to pH 7 after the gadolinium(III) salt is precipitated out. In some embodiments, the method further comprises reacting a compound of the formula:

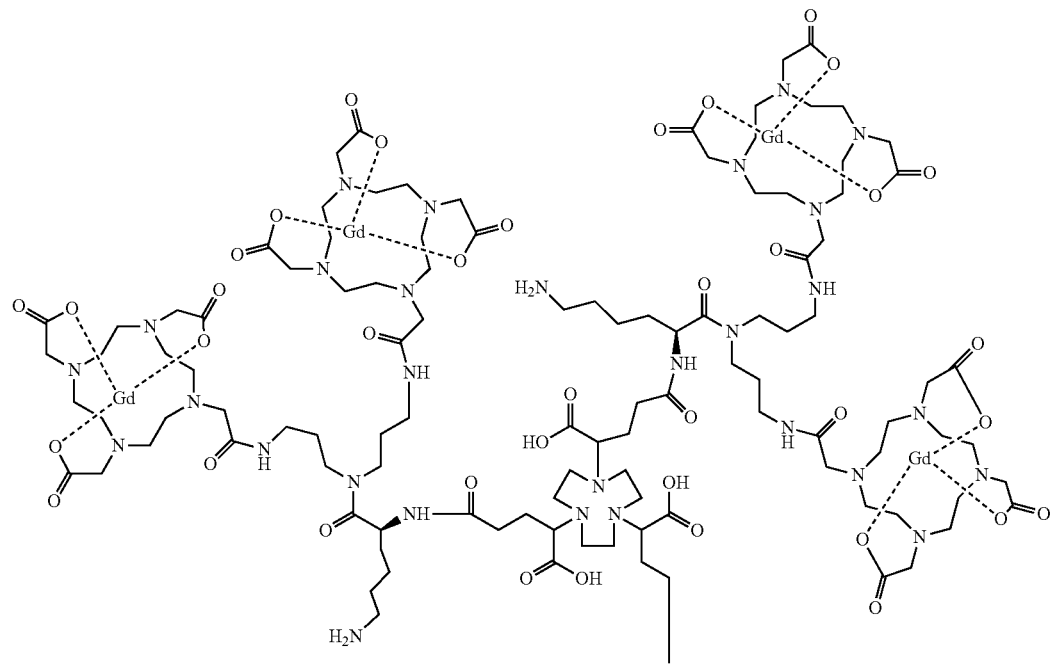
(IV)
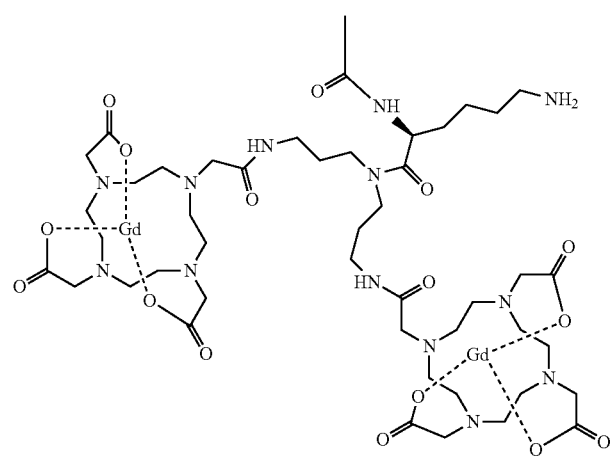

with a gallium(III) salt to form a compound of the formula:

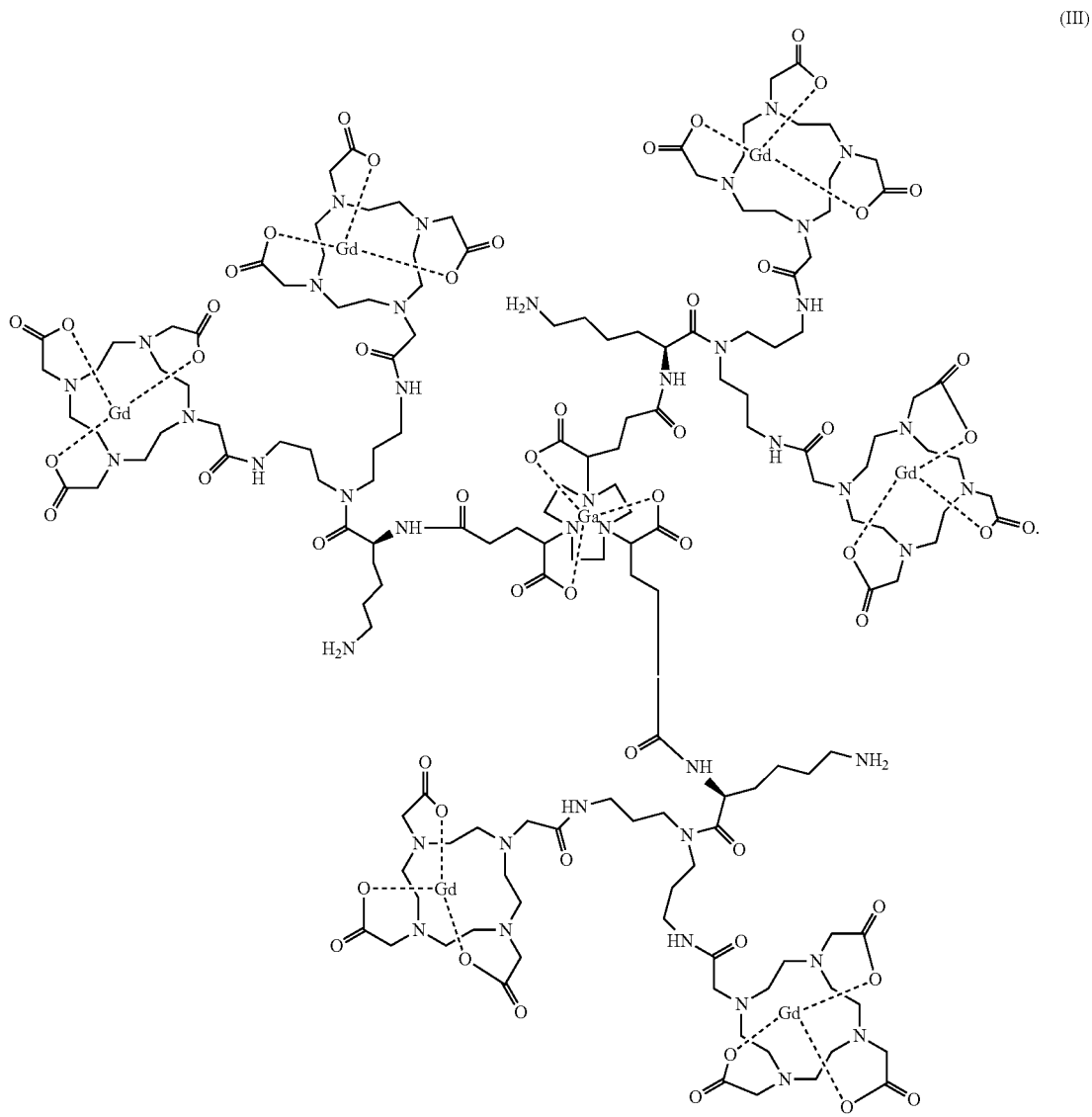

(III)

In some embodiments, the gallium(III) salt is gallium(III) chloride.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
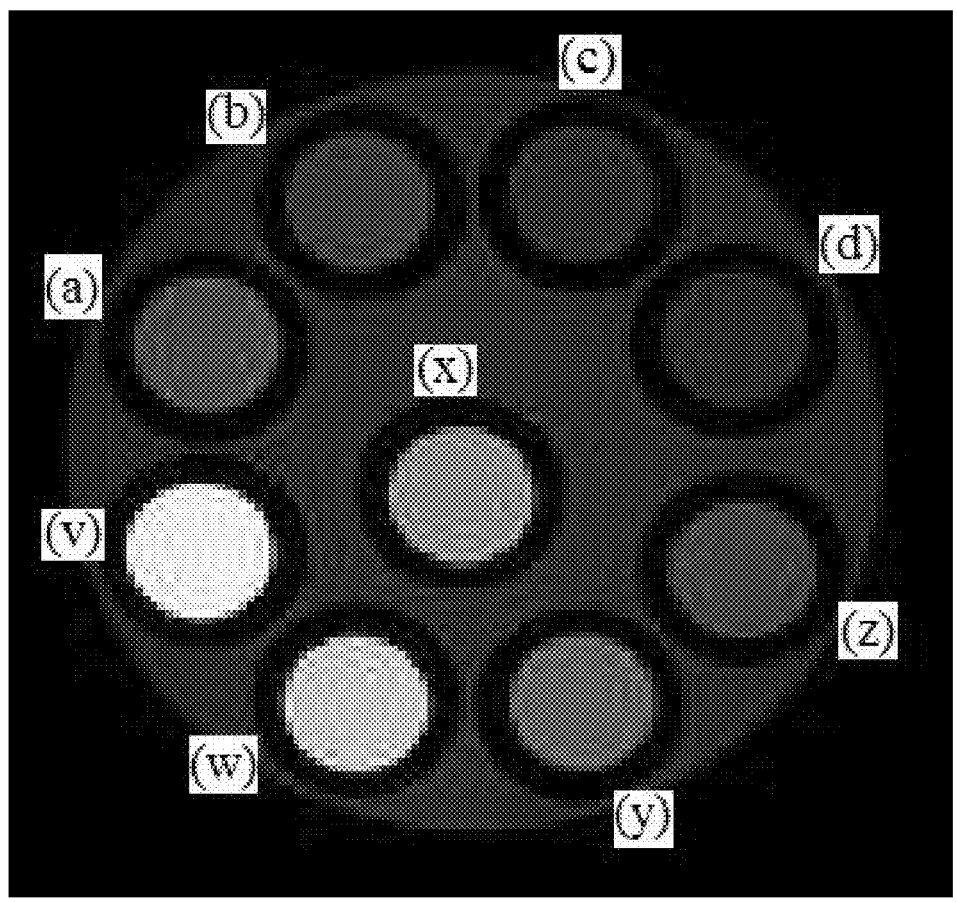
FIG. 1. $T_1$-weighted MR images of samples recorded at 7.0 T in 1.0 mL syringes containing Magnevist (a) 0.1 mM (b), 0.05 mM (c), 0.01 mM (d) 0.005 mM and $Gd^{3+}$-L complex (v) 0.1 mM, (w) 0.05 mM (x) 0.025 mM (y) 0.01 mM and (z) 0.005 mM FIG. 2. Bar graph representing biodistributions of $Ga^{3+}$-68($Gd^{3+}$-L) complex at 5 min., 1 h, 4 h, 24 h and 48 h post IV injection, respectively.

In some aspects, the present invention provides novel ligands that may be used to form novel imaging agents, including, for example, novel gadolinium and/or gallium complexes. In some embodiments, there is provided herein a novel DOTA based dual imaging agent having an ionic relaxivity of 17.25 mM$^{-1}$ s$^{-1}$ and capable of carrying Ga$^{3+}$-67/68 in its core for PET/SPECT imaging. In some embodiments, this agent may be used as a dual modality PET/MRI probe. In some embodiments, the NOTA core can be utilized to chelate Ga$^{3+}$-68, for example, for making the agent a PET probe. In some embodiments, the dendrimer like feature of the design enables the attachment of multiple DOTA units for enhancement of MRI sensitivity. In some embodiments, the probe carries three maleimide groups, each of which may be conjugated to sulfhydryl containing targeting ligand, thereby providing multivalency to the construct. As is the case with most dendritic molecules, the disclosed probe may have a definite molecular formula and may benefit from Gd-DOTA and Ga-NOTA in vivo stability. In some embodiments, the dendritic nature of the probe enables the selective loading of the two metals without compromising the other properties. In some embodiments, the design may allow for flexible disease targeting and different disease can be targeted by simply changing of target molecule. In some embodiments, the probe can easily be utilized for Single Photon Emission Computed Tomography (SPECT) or gamma scintigraphy by replacing Ga-68 with Ga-67 ($t_{1/2}$=3.26 d; γ: 184 keV).

A. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—. Any undefined valency on an atom of a structure shown in this application implicitly represents a hydrogen atom bonded to the atom.

In the context of chemical formulas, the symbol "—" means a single bond, "=" means a double bond; and "≡" means triple bond. The symbol "⎯⎯" represents an optional bond, which if present is either single or double. The symbol "═══" represents a single bond or a double bond. Thus, for example, the structure

includes the structures

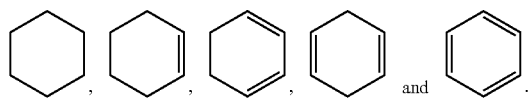

As will be understood by a person of skill in the art, no one such ring atom forms part of more than one double bond. The symbol "〰", when drawn perpendicularly across a bond indicates a point of attachment of the group. It is noted that the point of attachment is typically only identified in this manner for larger groups in order to assist the reader in rapidly and unambiguously identifying a point of attachment. The symbol "◄" means a single bond where the group attached to the thick end of the wedge is "out of the page." The symbol "⫼⫼⫼" means a single bond where the group attached to the thick end of the wedge is "into the page". Furthermore, while the covalent bond symbol "—", when used to attach a group to a stereogenic carbon, does not indicate any preferred stereochemistry, it does cover all stereochemical representations including "◄" and "⫼⫼⫼". The symbol "〰" means a single bond where the conformation (e.g., either R or S) or the geometry is undefined (e.g., either E or Z).

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., "alkyl$_{(C≤8)}$" For example, "alkyl$_{(C≤10)}$" designates those alkyl groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neopentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$- (methylene), —CH$_2$CH$_2$—, —CH$_2$C(CH$_3$)$_2$CH$_2$—, —CH$_2$CH$_2$CH$_2$—, and

are non-limiting examples of alkanediyl groups. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) CH$_3$, —N(CH$_3$)$_2$, —C(O)NH$_2$, —OC(O)CH$_3$, or —S(O)$_2$ NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O) NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CHCH═CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH═CH—, —CH═C(CH$_3$)CH$_2$—, —CH═CHCH$_2$—, and

are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH═CHF, —CH═CHCl and —CH═CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. The term "alkynediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon triple bond, no carbon-carbon double bonds, and no atoms other than carbon and hydrogen. The groups, —C≡C—, —C≡CCH$_2$—, and —C≡CCH$_2$—, are non-limiting examples of alkenediyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

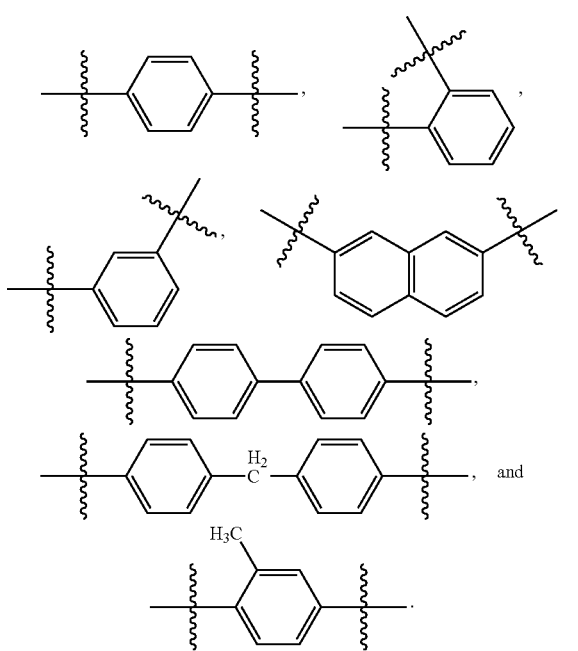

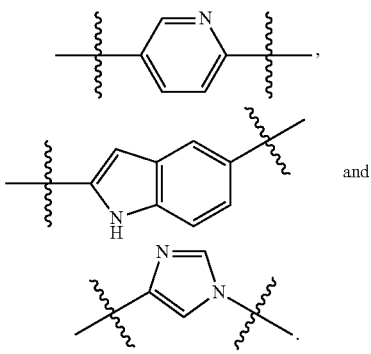

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

An "amino acid" is a functional group which contains a —CO$_2$H and a —NH$_2$ group on the same carbon skeleton. In its preferred embodiment, the term "amino acid" refers to one of the naturally occurring or commercially available amino acids as well as their enantiomers and diastereomers. In its most preferred embodiment, the term "amino acids" refers the 20 canonical amino acids and their enantiomers and diastereomers. As used herein, the term "amino acid residue" refers to a divalent amino acid which is linked through both the amine group and carboxylate group as shown, e.g.,

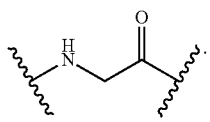

When used with the phrase, "linked to a targeting moiety", an amino acid is combined together through a covalent or some non-bonding interaction with a targeting moiety such as a drug, a peptide, a protein, a protein substrate, another ligand, or an antibody.

The term "metal complex" is compound comprising at least one ligand and at least one metal ion, wherein the ligand and the metal ion are attached to one another by one or more metal-ligand bonds.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

B. Compounds and Synthetic Methods Thereof

In some aspects, the present invention provides novel ligands of the formula:

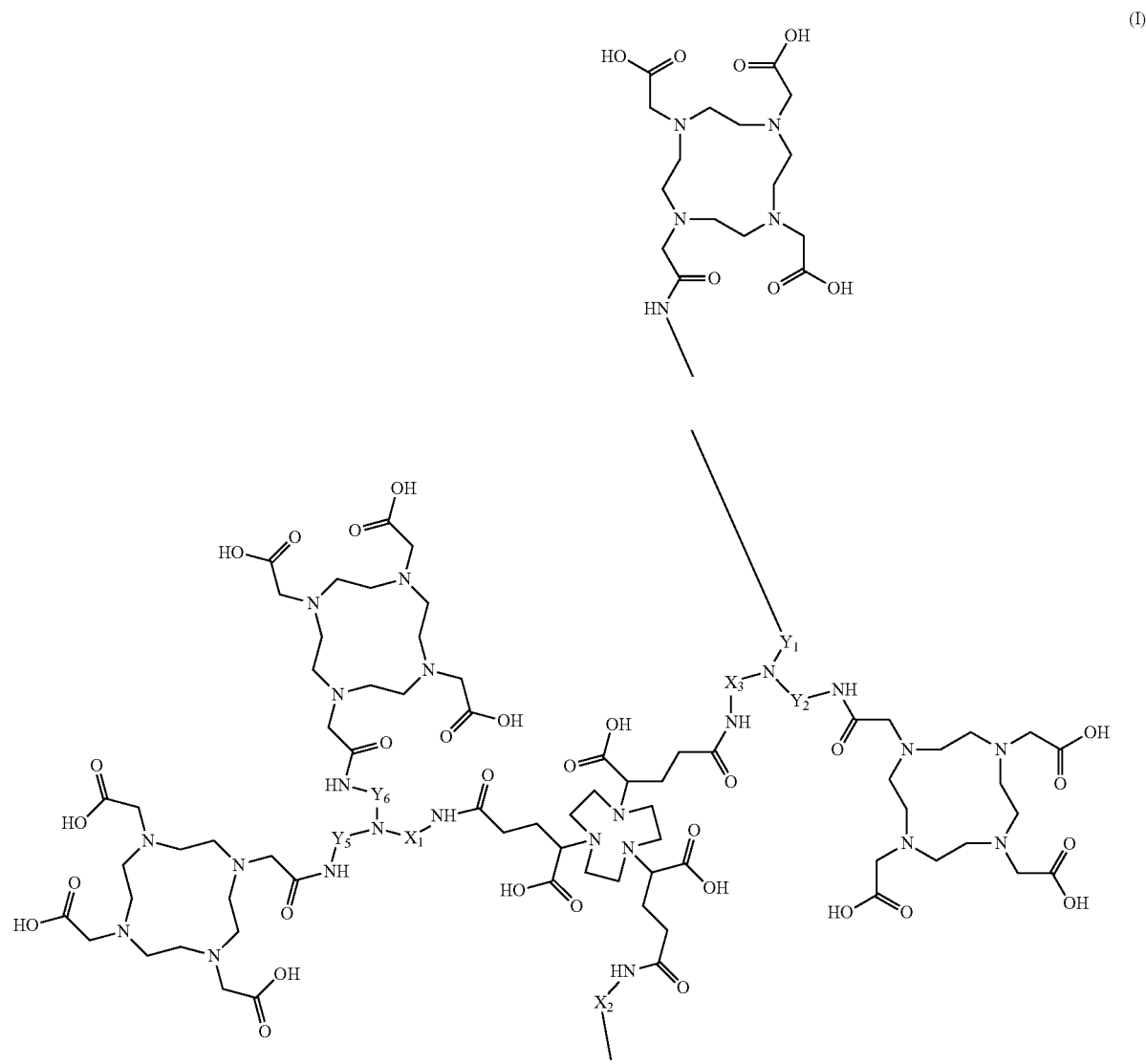

(I)

-continued

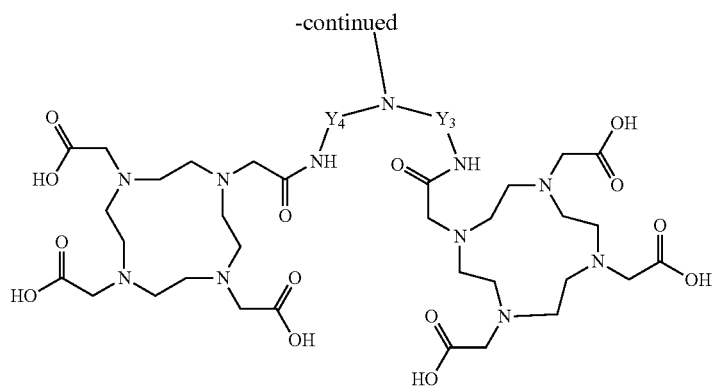

$X_1$, $X_2$, and $X_3$ are each independently alkanediyl$_{(C \leq 12)}$, alkenediyl$_{(C \leq 12)}$, alkynediyl$_{(C \leq 12)}$, arenediyl$_{(C \leq 12)}$, heteroarenediyl$_{(C \leq 12)}$, alkoxydiyl$_{(C \leq 12)}$, alkylaminodiyl$_{(C \leq 12)}$, or a substituted version of any of these groups; or an amino acid residue, an amino acid residue linked to a targeting moiety, a PEG linker comprising between 2 and 200 repeating units; and $Y_1$, $Y_2$, $Y_3$, $Y_4$, $Y_5$, and $Y_6$ are each independently alkanediyl$_{(C \leq 12)}$, alkenediyl$_{(C \leq 12)}$, alkynediyl$_{(C \leq 12)}$, arenediyl$_{(C \leq 12)}$, heteroarenediyl$_{(C \leq 12)}$, alkoxydiyl$_{(C \leq 12)}$, alkylaminodiyl$_{(C \leq 12)}$, or a substituted version of any of these groups; or an amino acid residue, an amino acid residue linked to a targeting moiety, a PEG linker comprising between 2 and 200 repeating units; or a metal complex or salt thereof. In some embodiments, (II)

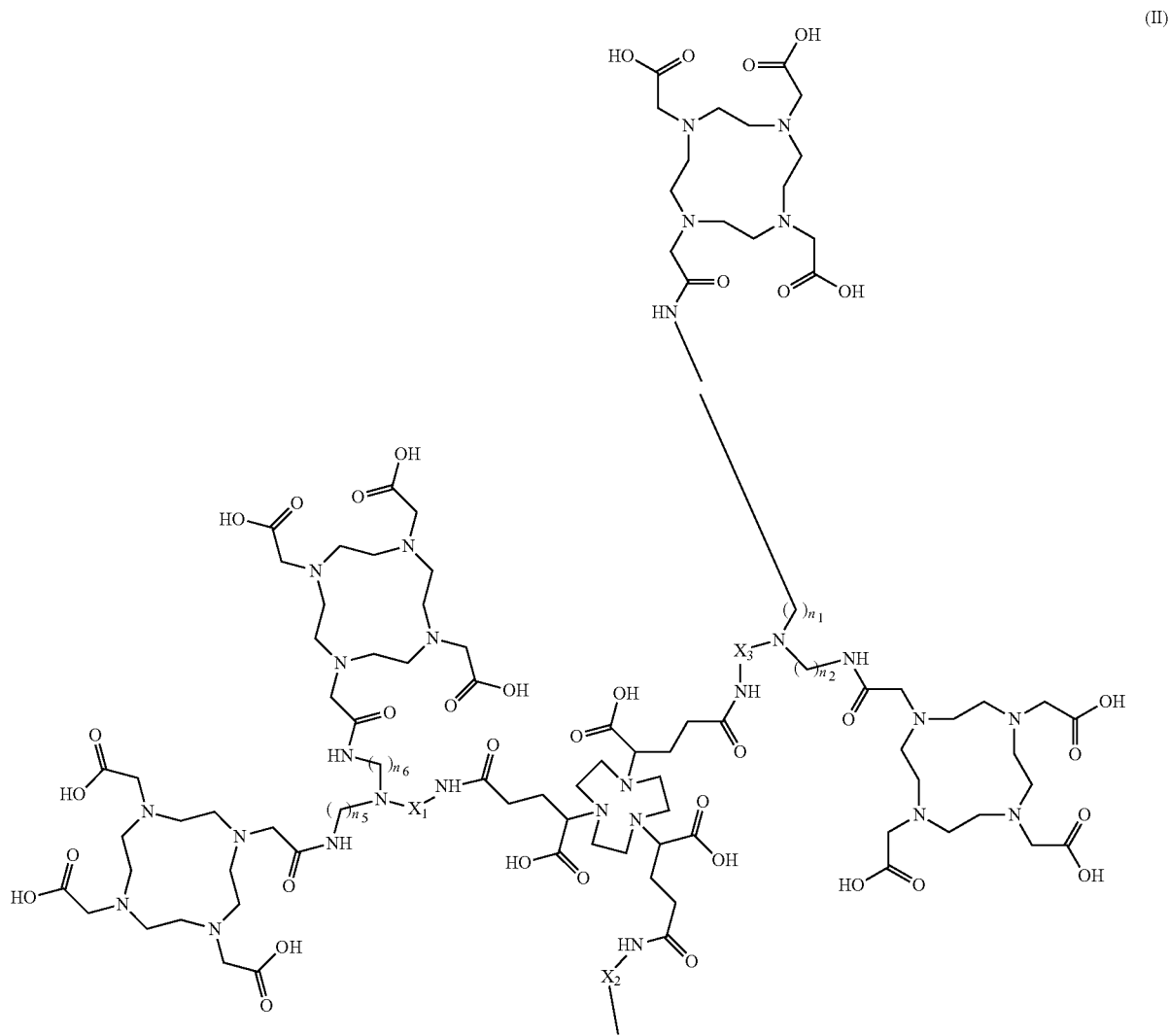

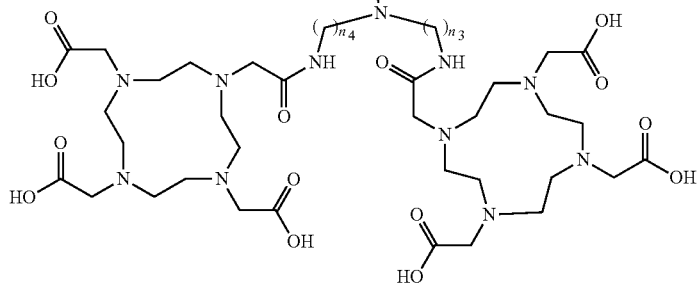

wherein: $X_1$, $X_2$, and $X_3$ are each independently selected from an amino acid residue or an amino acid residue linked to a targeting moiety; and $n_1$, $n_2$, $n_3$, $n_4$, $n_5$, and $n_6$ are each independently 1-5; or metal complexes or salts of the formula I. In some embodiments, $X_1$, $X_2$, and $X_3$ are each an amino acid residue. In some specific embodiments, $X_1$, $X_2$, and $X_3$ are each lysine. In some embodiments, $X_1$, $X_2$, and $X_3$ are each an amino acid residue linked to a targeting moiety. In some embodiments, $X_1$, $X_2$, and $X_3$ are each a lysine linked to a targeting moiety. In some embodiments, the targeting moiety is a cyclic RDGyK peptide. In some embodiments, the cyclic RDGyK peptide comprises a linker with a mercapto group. In some embodiments, the cyclic RDGyK peptide further comprises a PEG linker comprising between 2 and 200 repeating units. In some embodiments, the PEG linker comprises between 2 and 50 repeating units. In some embodiments, the PEG linker comprises between 2 and 20 repeating units. In some embodiments, the amino acid residue linked to a targeting moiety is further defined by the structure:

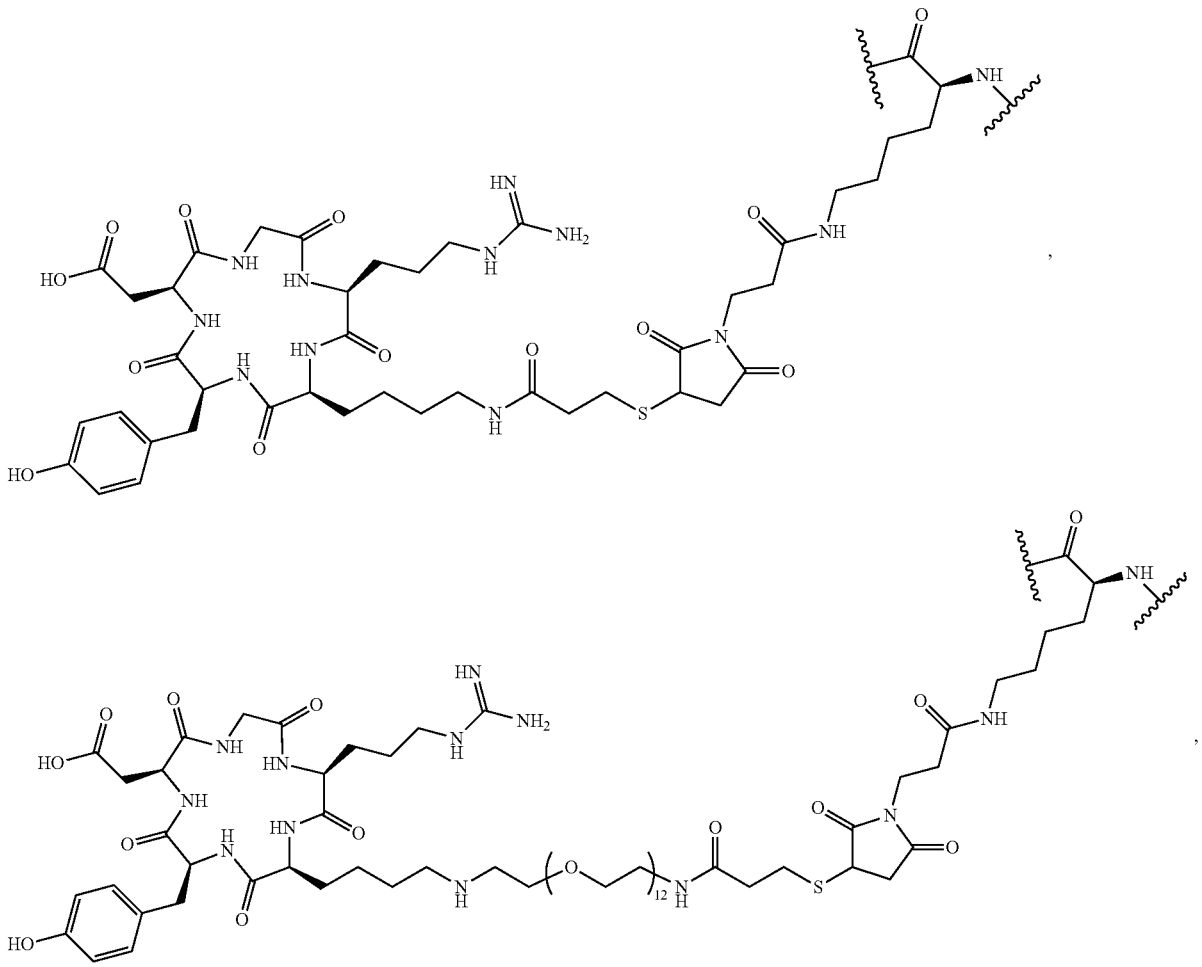

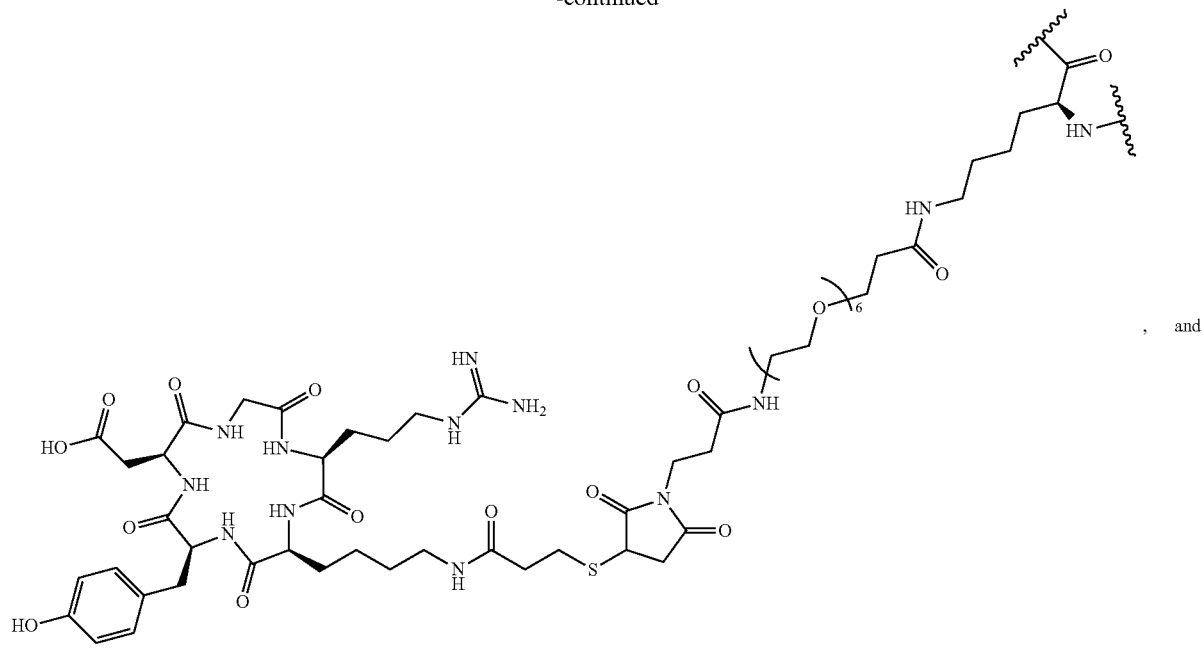

, and

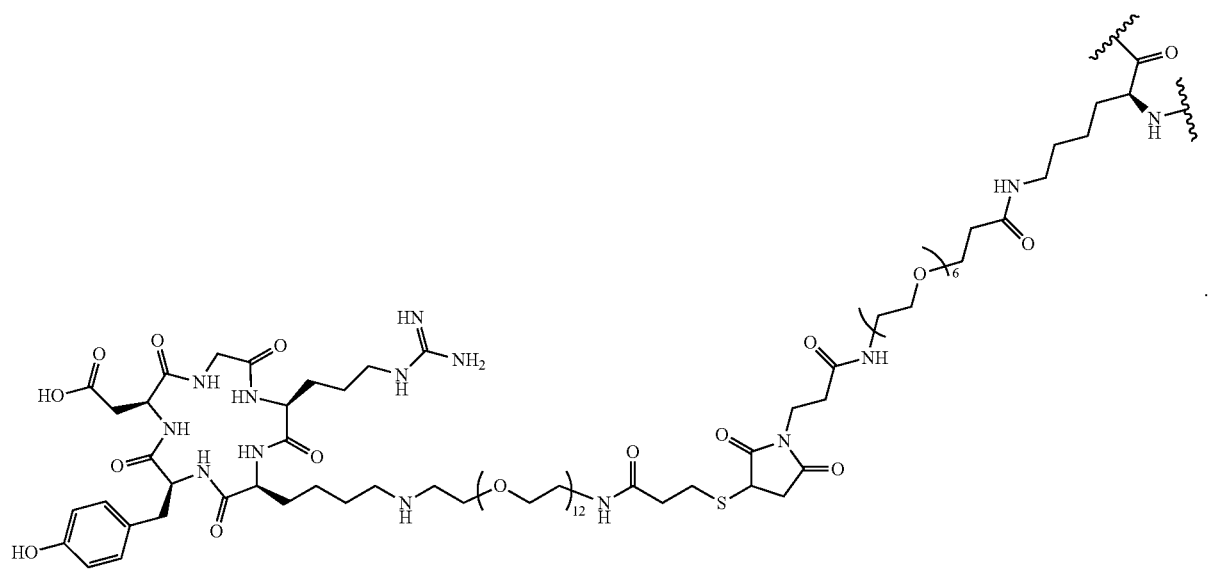

In some specific embodiments, $X_1$, $X_2$, and $X_3$ are each independently alkanediyl$_{(C \leq 12)}$, alkoxydiyl$_{(C \leq 12)}$, alkylaminodiyl$_{(C \leq 12)}$, or a substituted version of any of these groups; or an amino acid residue, an amino acid residue linked to a targeting moiety, a PEG linker comprising between 2 and 200 repeating units. In some specific embodiments, $Y_1$, $Y_2$, $Y_3$, $Y_4$, $Y_5$, and $Y_6$ are each independently alkanediyl$_{(C \leq 12)}$, alkoxydiyl$_{(C \leq 12)}$, alkylaminodiyl$_{(C \leq 12)}$, or a substituted version of any of these groups; or an amino acid residue, an amino acid residue linked to a targeting moiety, a PEG linker comprising between 2 and 200 repeating units. In some embodiments, $n_1$, $n_2$, $n_3$, $n_4$, $n_5$, and $n_6$ are each 3. In some embodiments, the ligand is further defined by the formula:

73 74
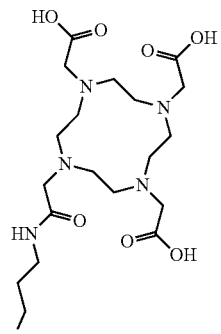
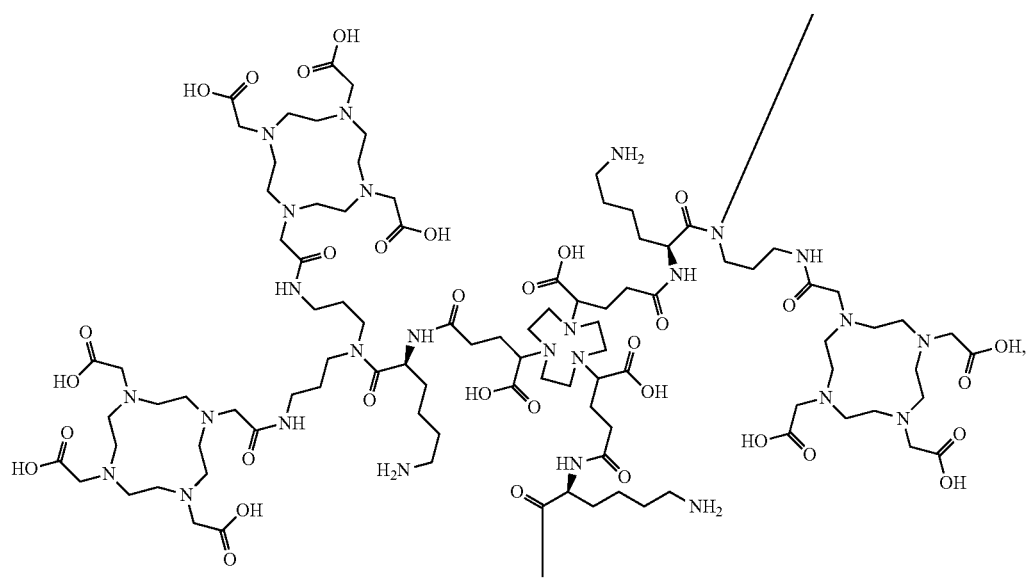
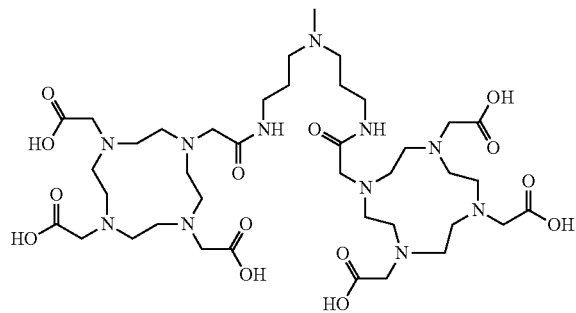
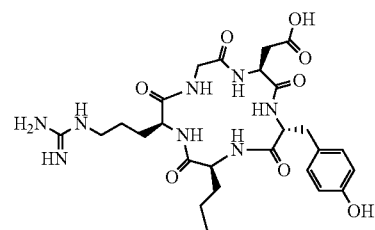

75 76
-continued
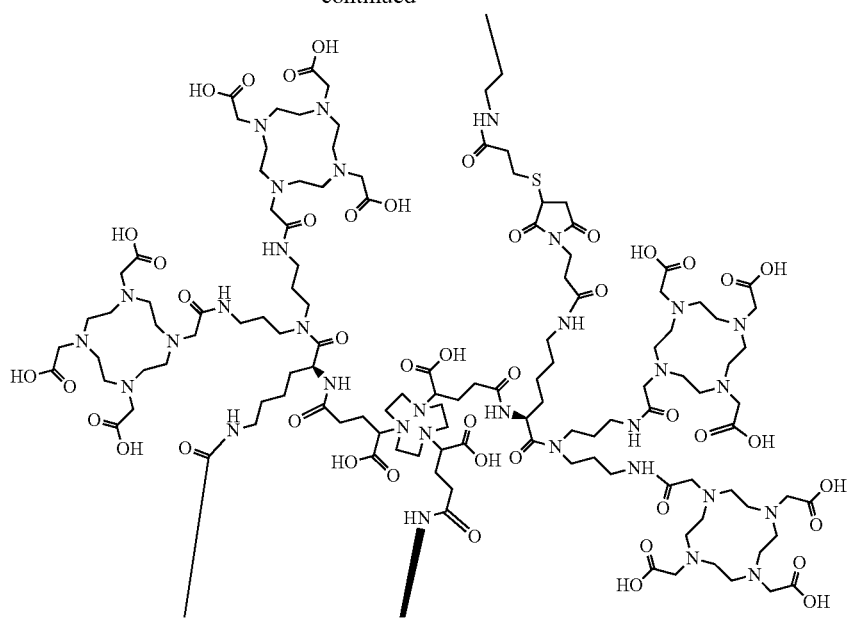
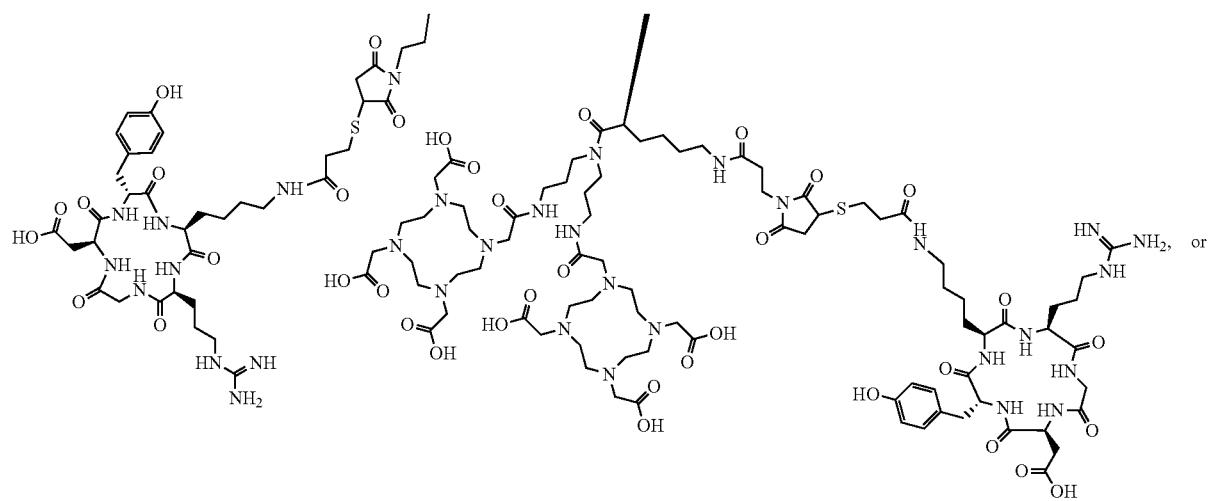
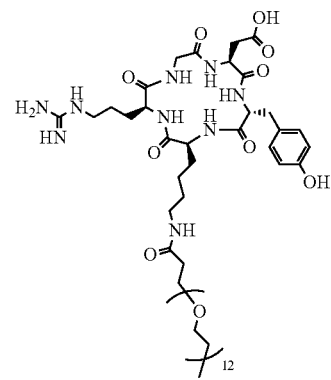

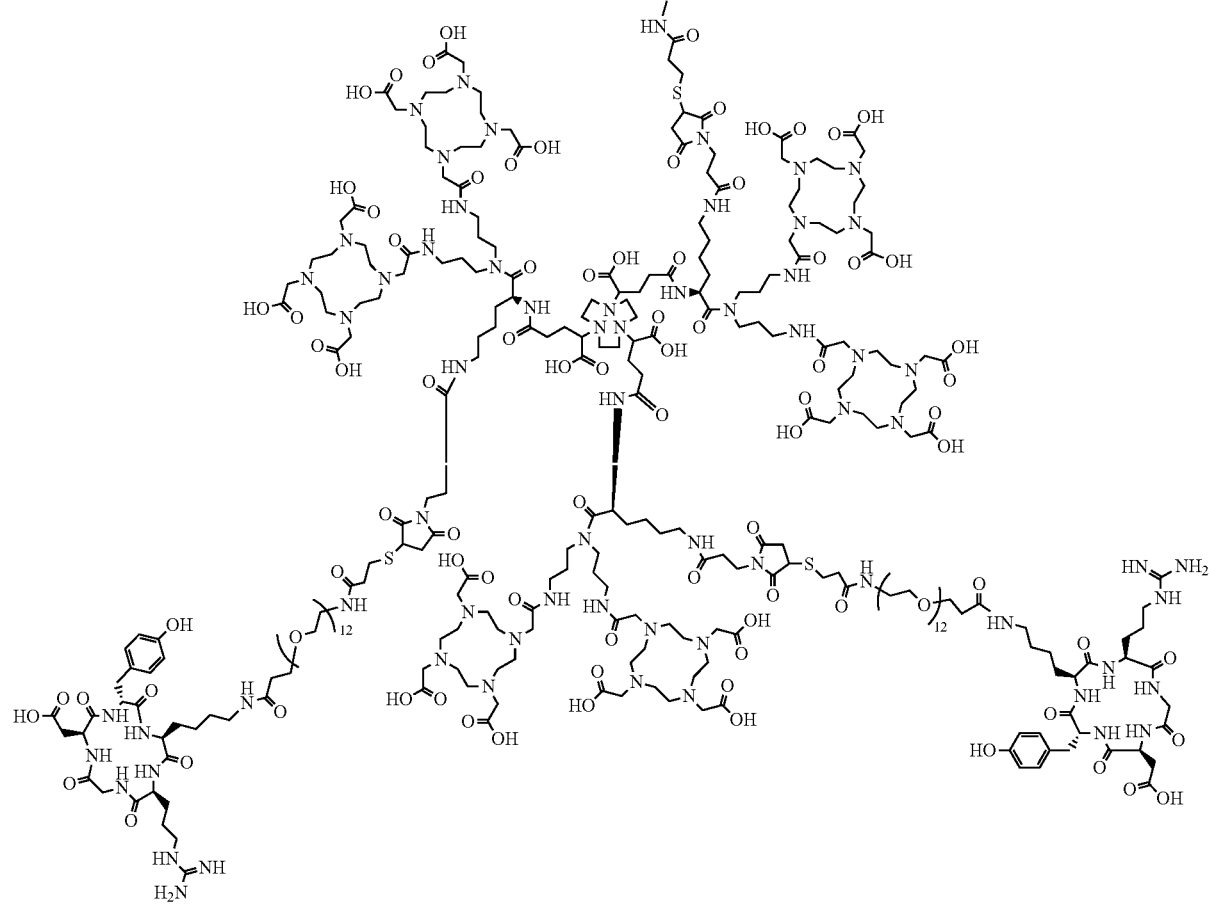
or a metal complex or salt thereof. In some embodiments, the intermediate ligands to the compounds described above are defined by the formulas:
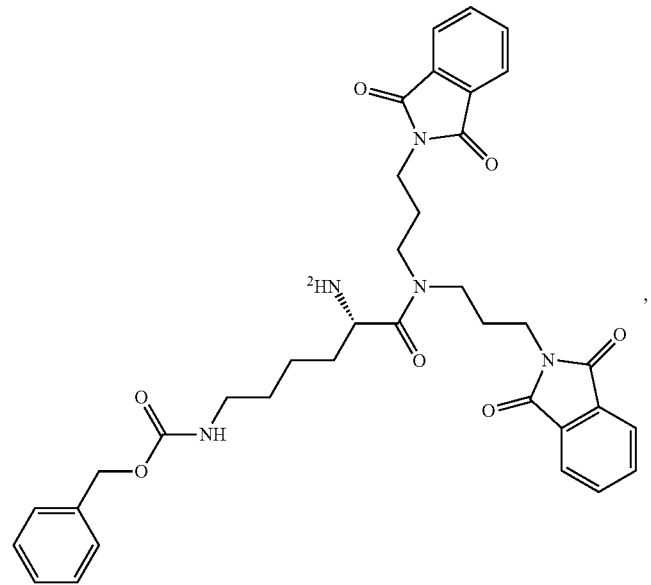

-continued
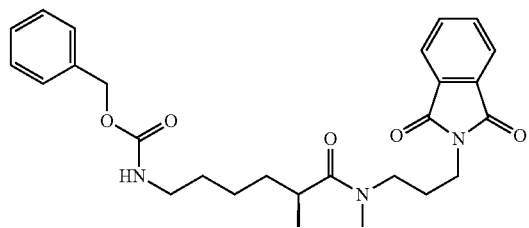
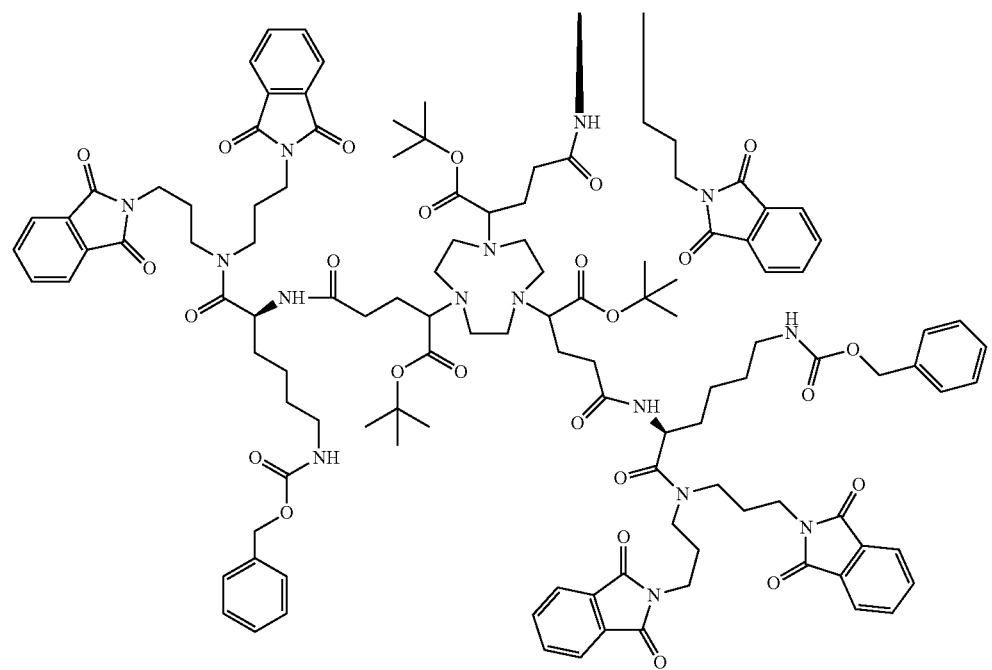
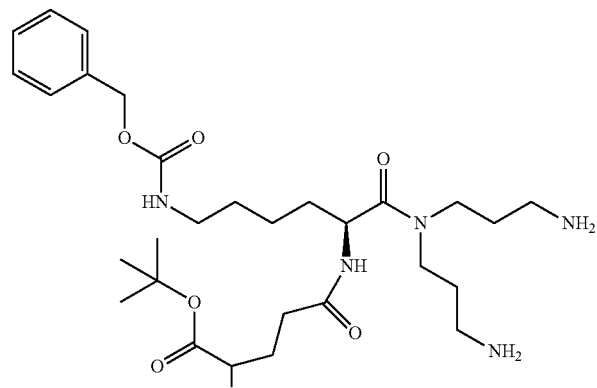

81
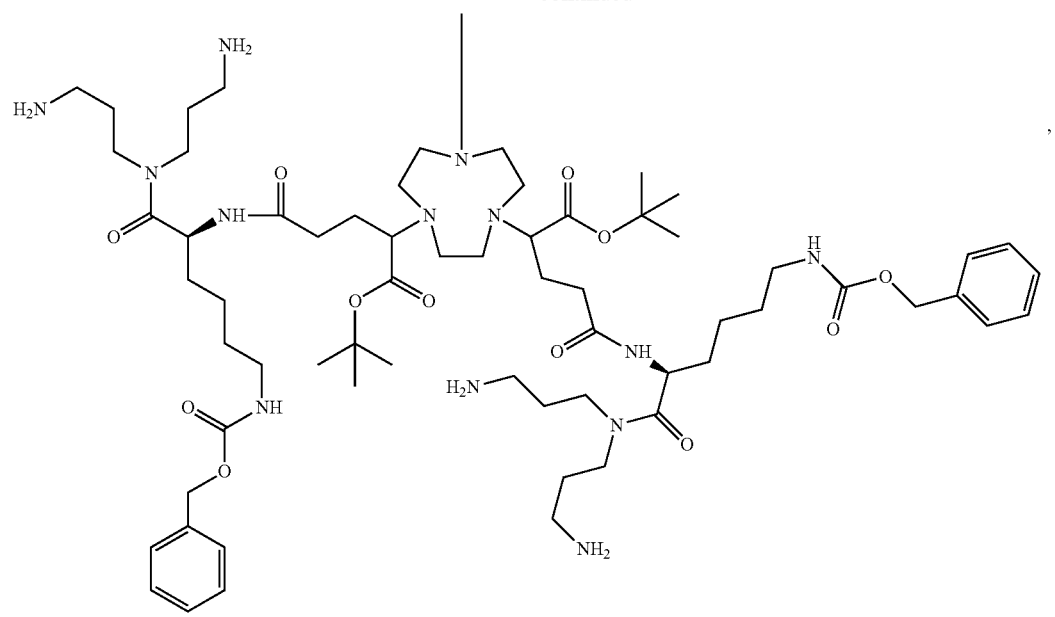
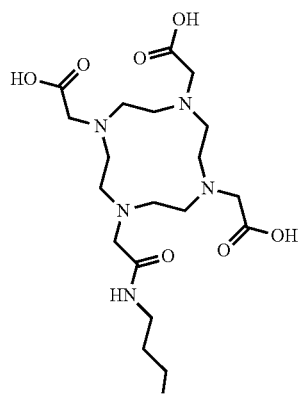
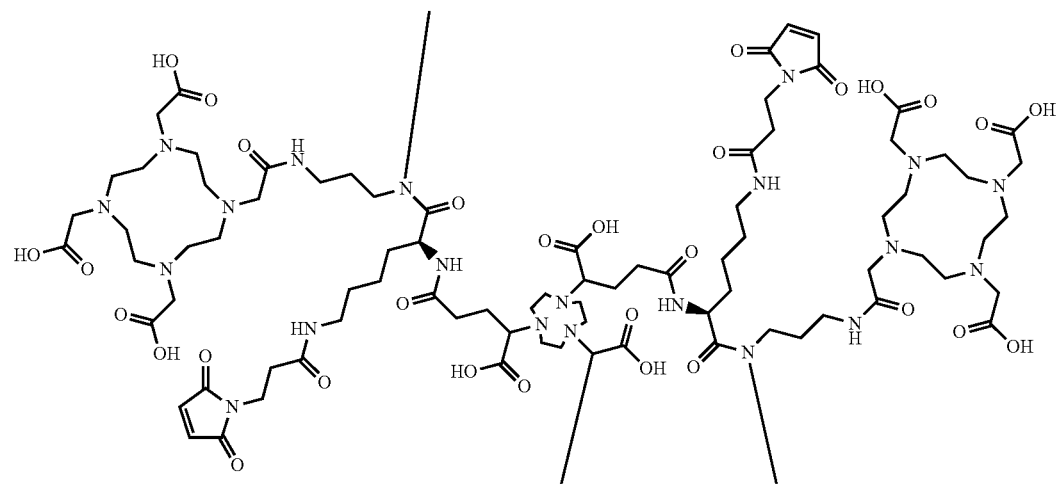

83 84
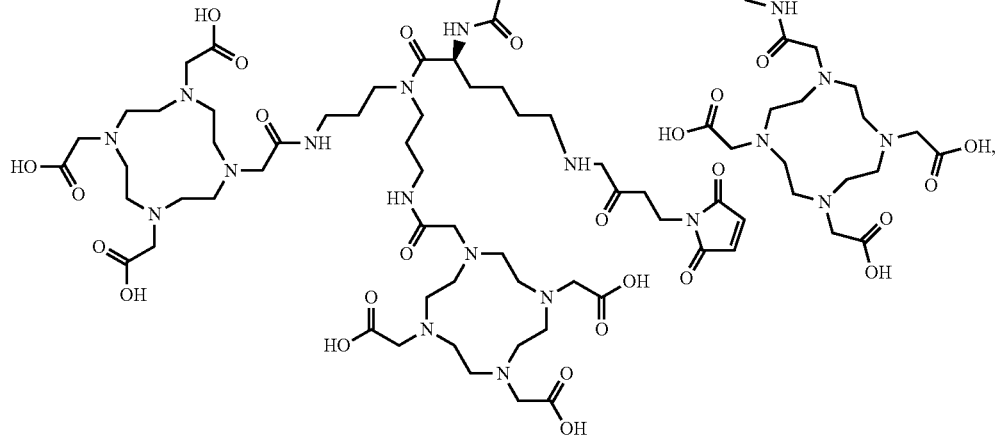
-continued
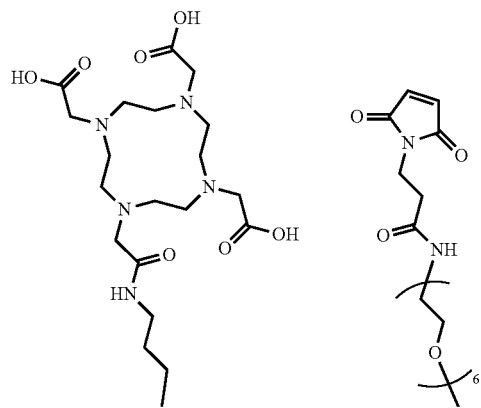
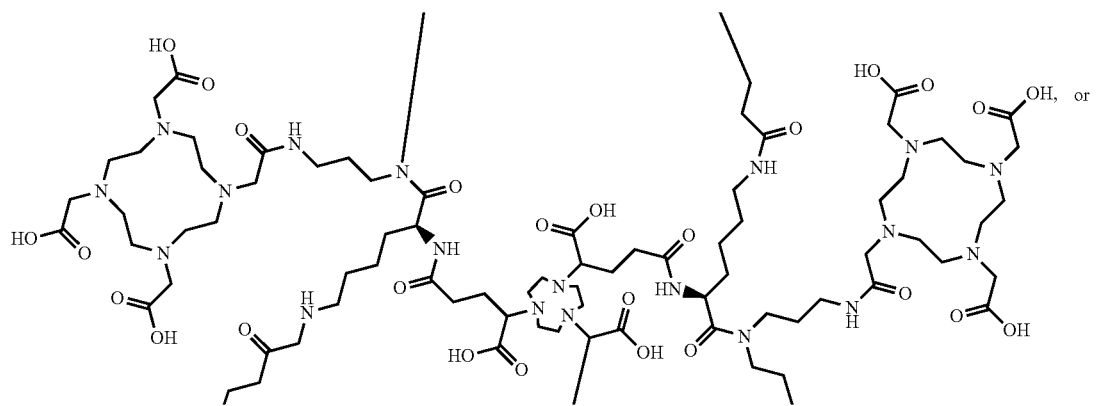

85
86
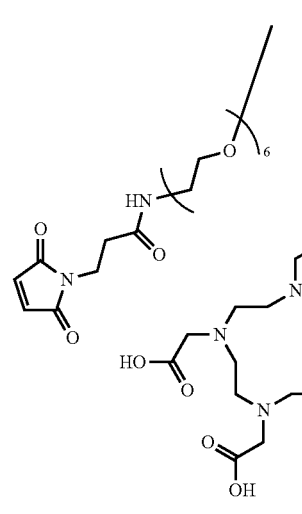
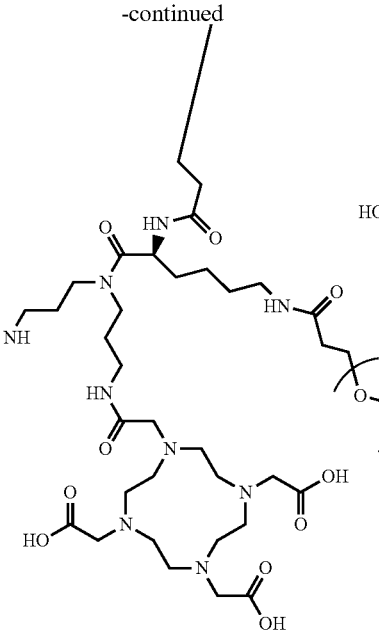
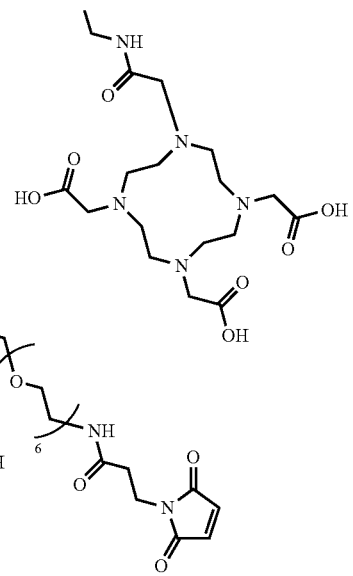
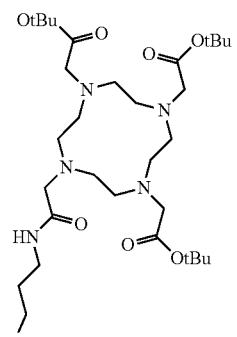
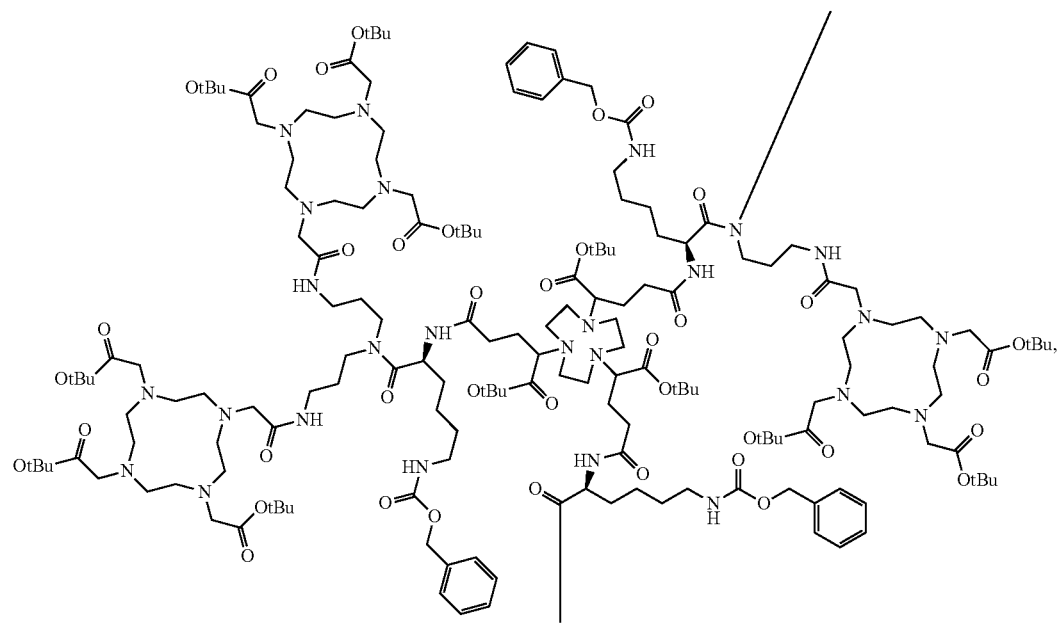

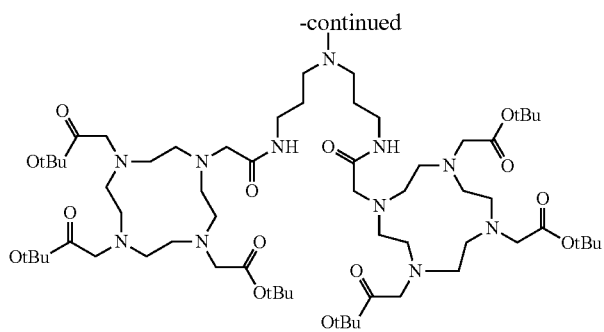
-continued
or metal complexes or salts of any of these formulas.
In some embodiments, the ligand forms a complex with one or more metal atoms, for example, to form a complex having the formula:
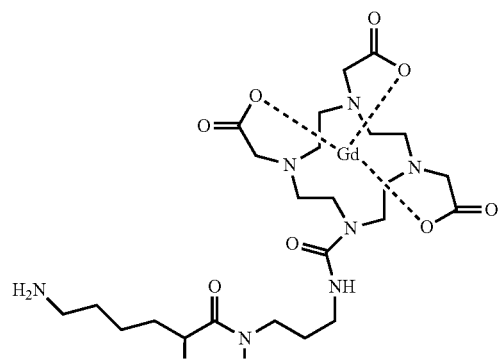
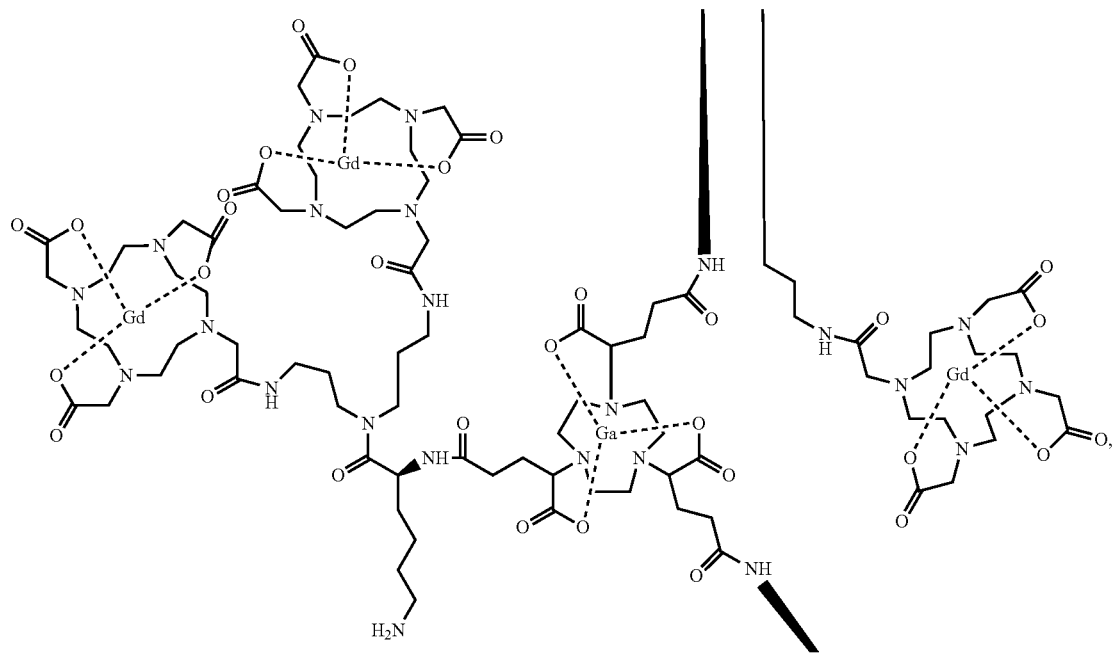

-continued
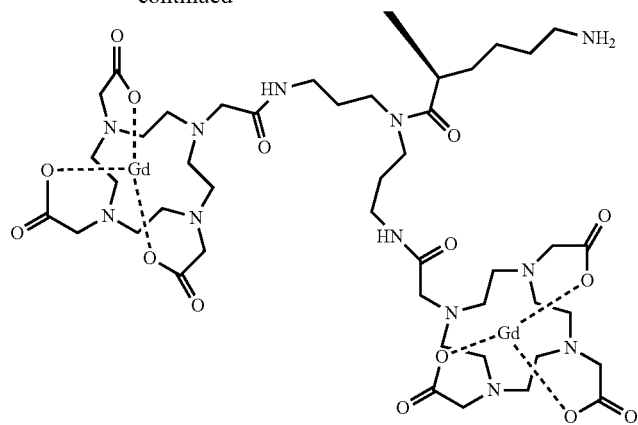
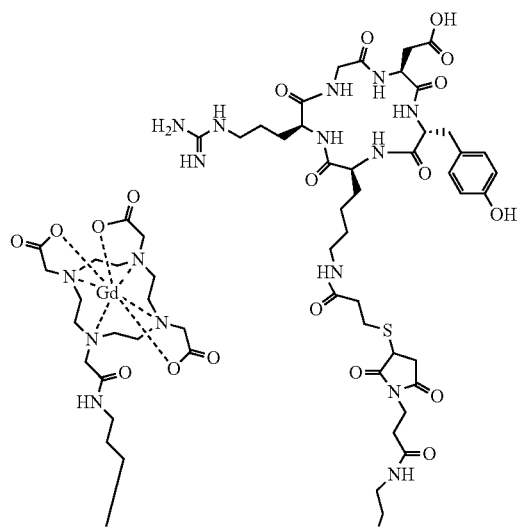
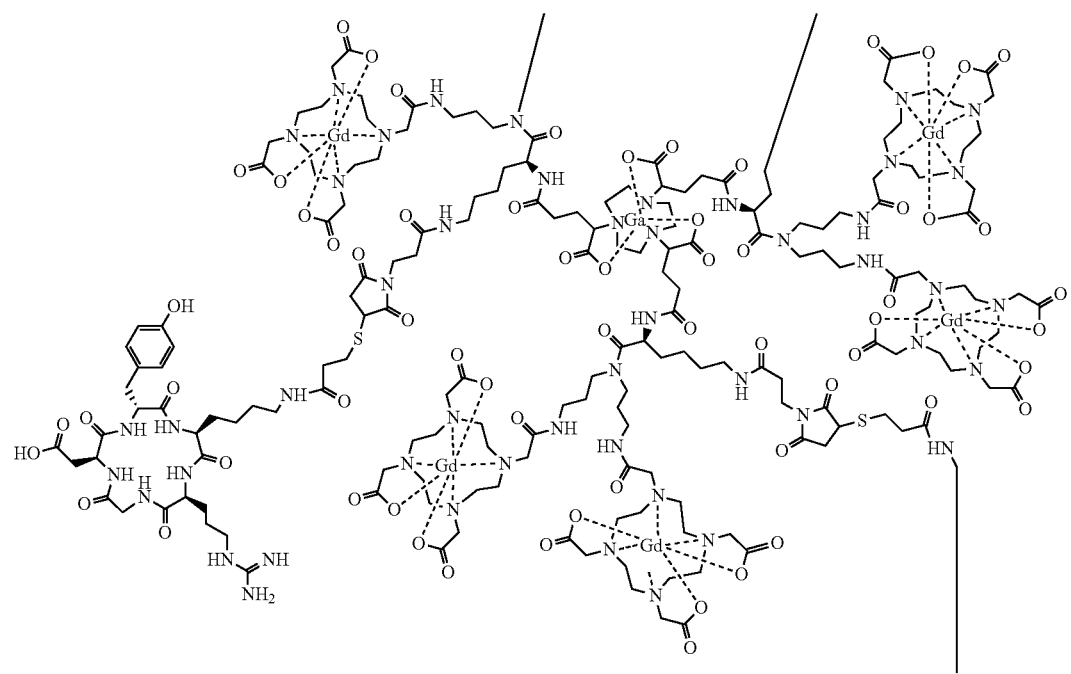

-continued
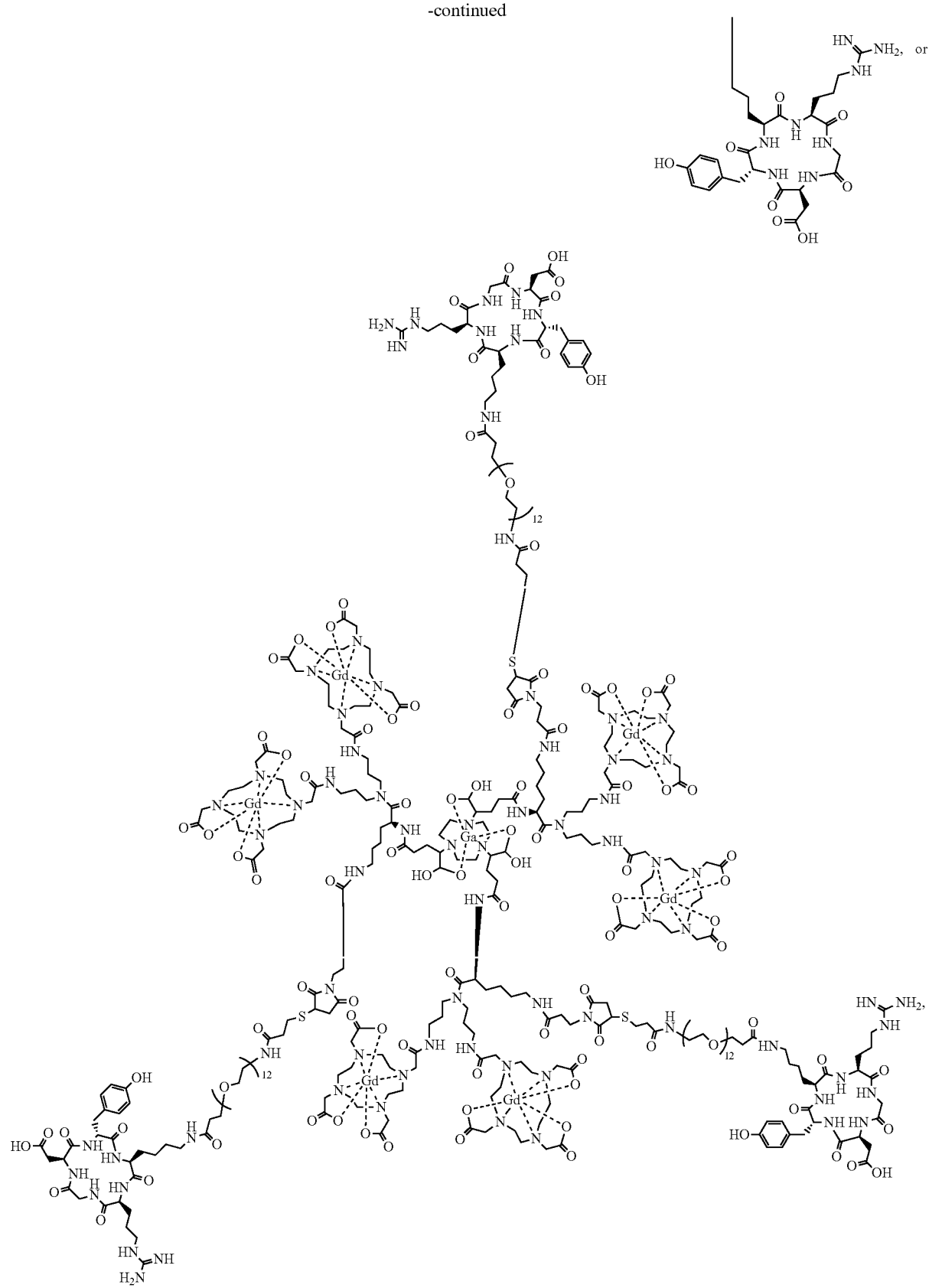
or a salt thereof.

In some embodiments, the complex has a formula:
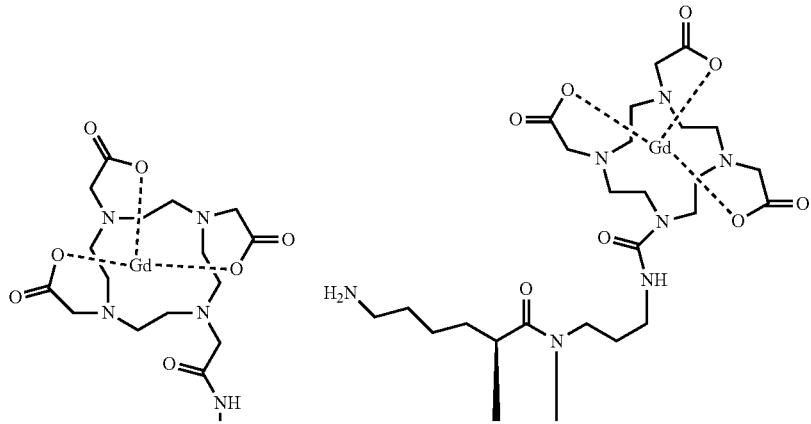
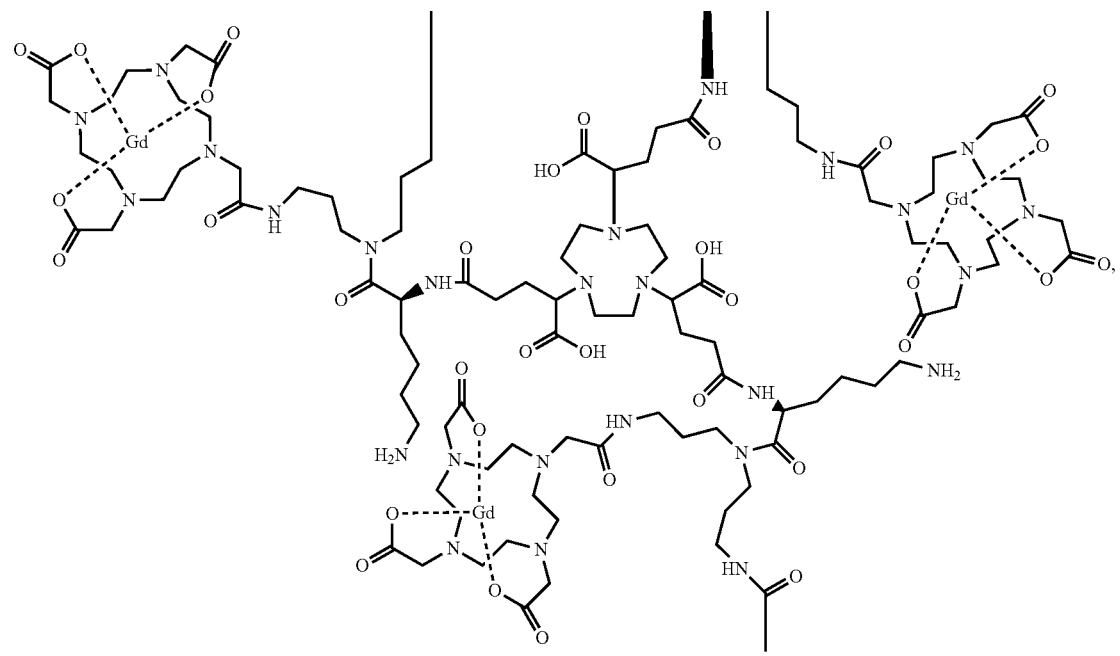
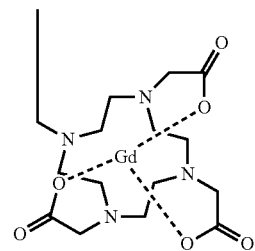

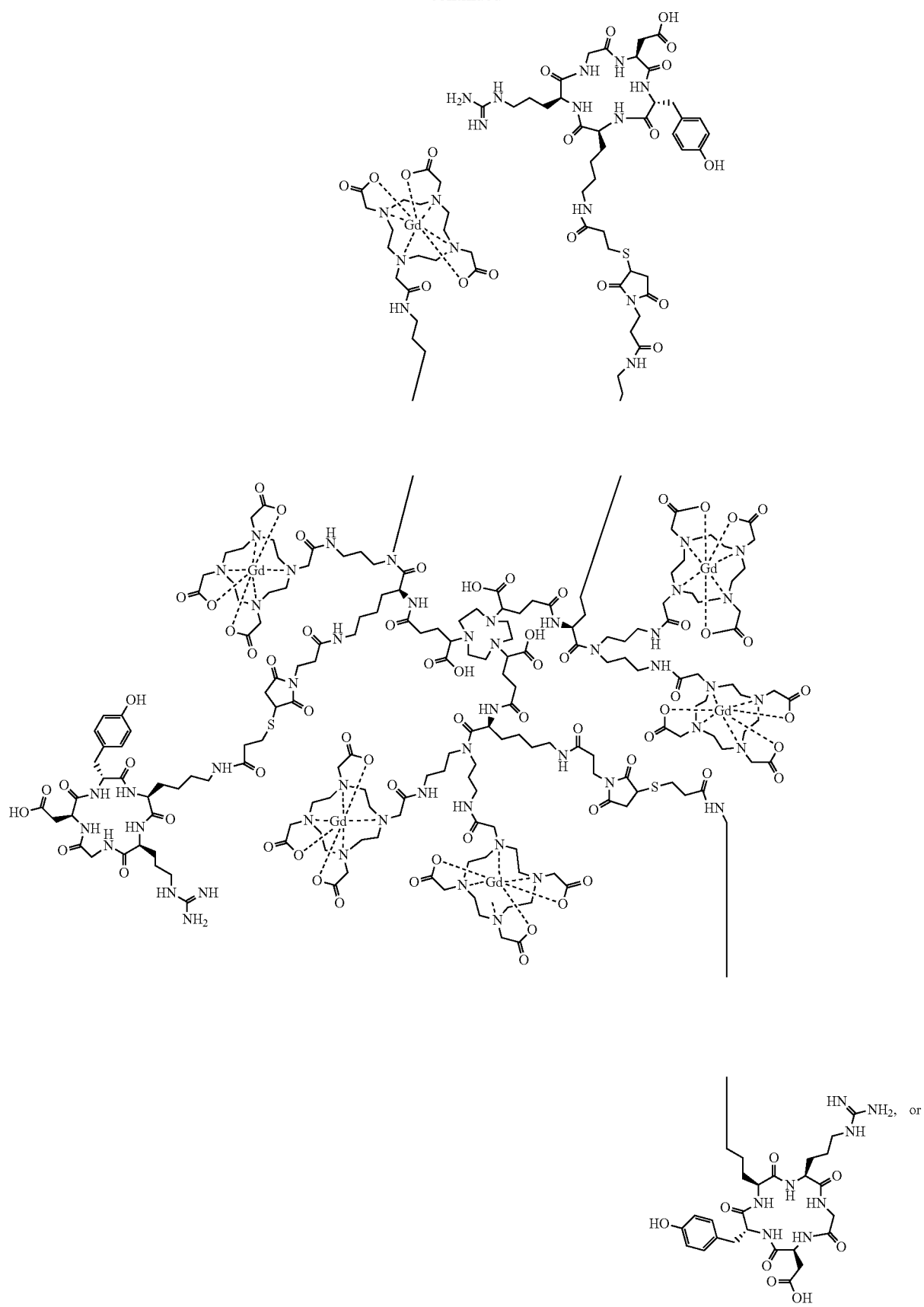

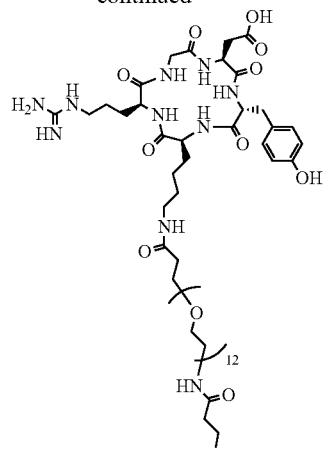
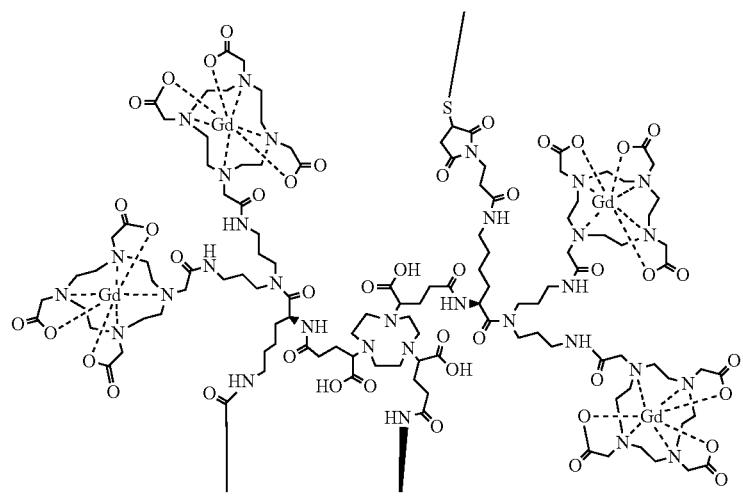
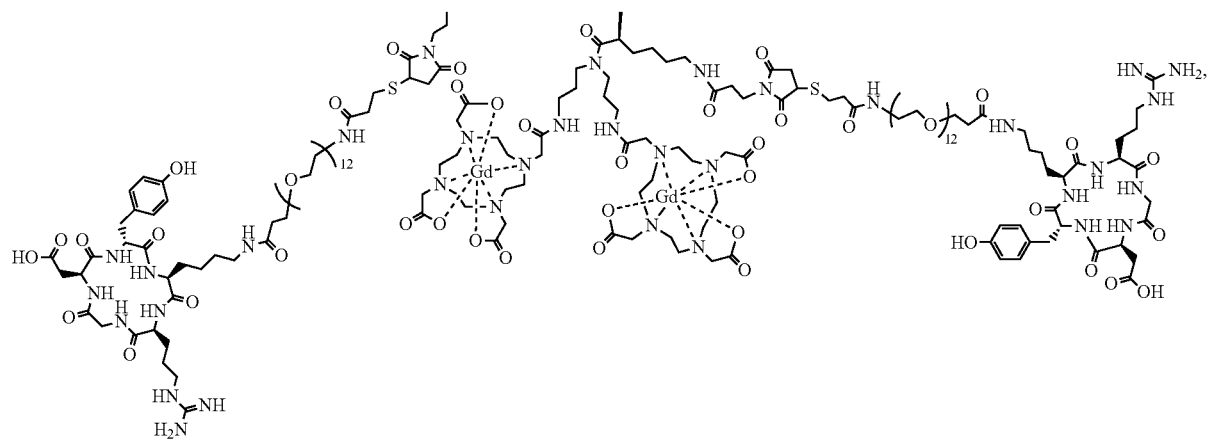
or a salt thereof. In some aspects, the present disclosure provides a compound of the formula:

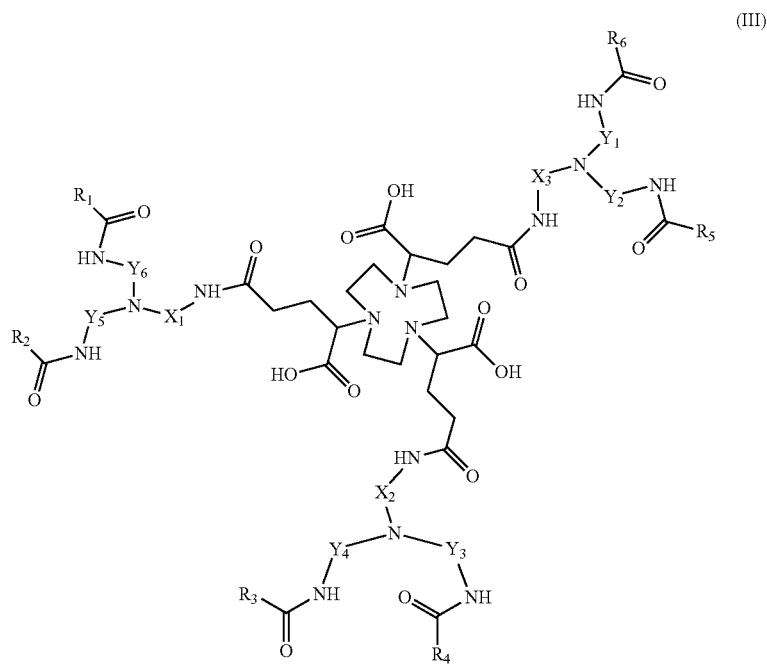

(III)

wherein: $R_1$, $R_2$, $R_3$, $R_4$, $R_5$, and $R_6$ are each independently selected from:

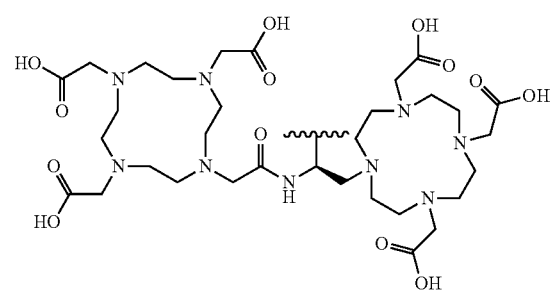

or

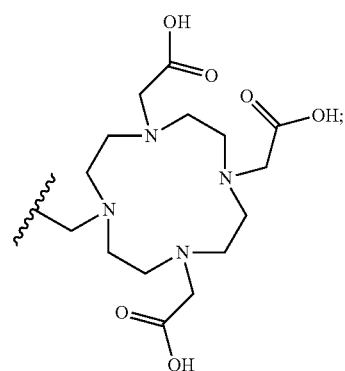

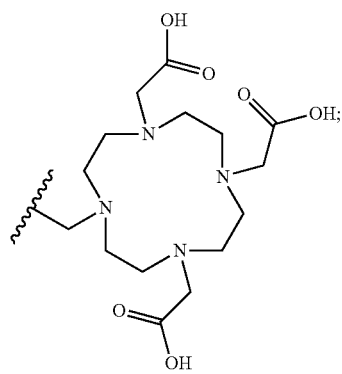 [SMILES: *CN1CCN(CC(=O)O)CCN(CC(=O)O)CCN(CC(=O)O)CC1]

$X_1$, $X_2$, and $X_3$ are each independently alkanediyl$_{(C \le 12)}$, substituted alkanediyl$_{(C \le 12)}$, an amino acid residue, an amino acid residue linked to a targeting moiety, a PEG linker comprising between 2 and 200 repeating units; $Y_1$, $Y_2$, $Y_3$, $Y_4$, $Y_5$, and $Y_6$ are each independently alkanediyl$_{(C \le 12)}$, substituted alkanediyl$_{(C \le 12)}$, an amino acid residue, an amino acid residue linked to a targeting moiety, a PEG linker comprising between 2 and 200 repeating units; and provided that all of $R_1$, $R_2$, $R_3$, $R_4$, $R_5$, and $R_6$ are not or a metal complex or salt thereof. In some embodiments, the compound is further defined as:

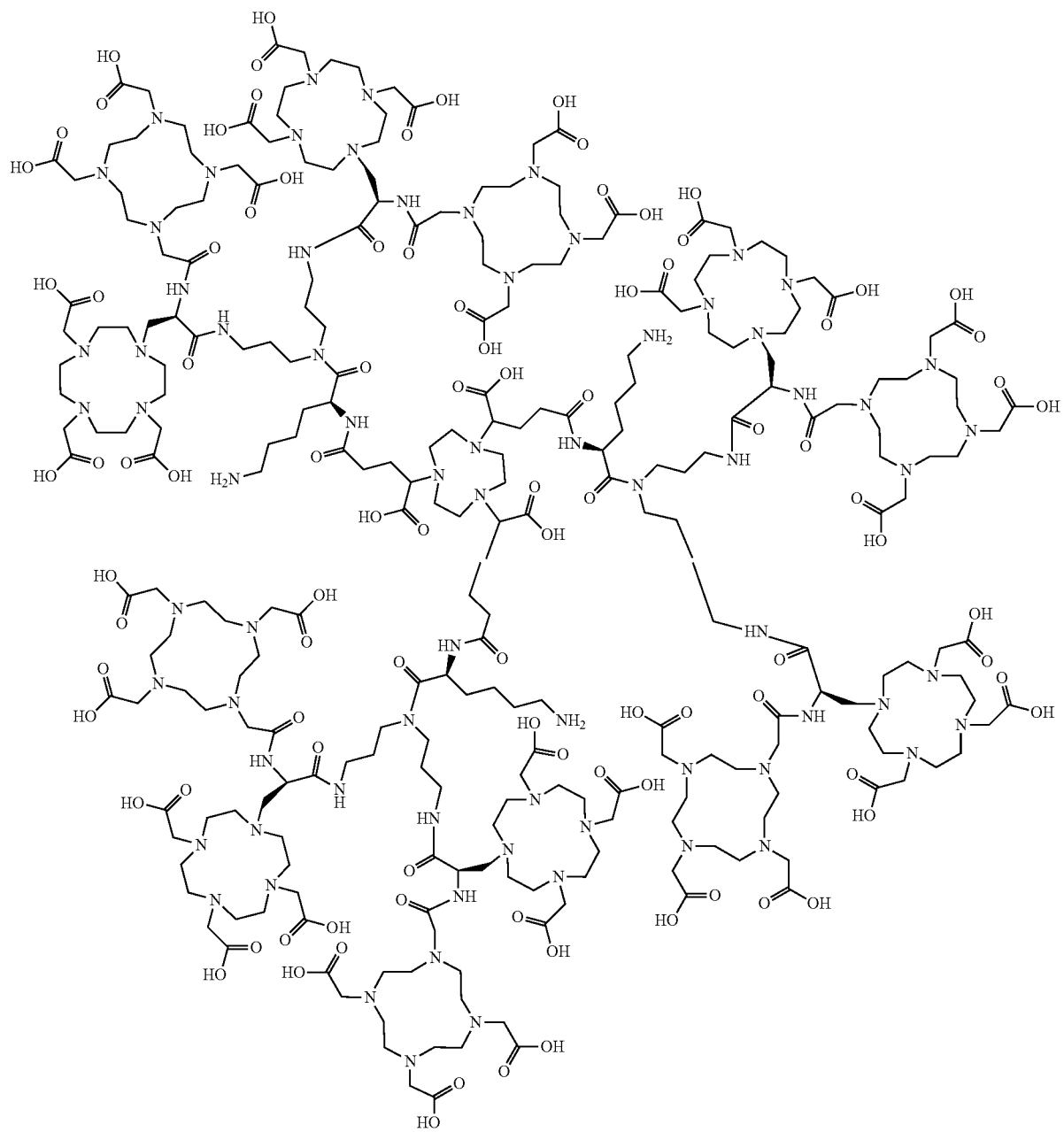

or a metal complex or salt thereof.

The novel, compounds, complexes, and ligands provided herein, may be prepared according to the methods described below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The ligands described in this disclosure may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. The ligands of this disclosure may occur as racemates and racemic mixtures, single enantiomers, diastereomeric mixtures and individual diastereomers. In some embodiments, a single diastereomer is obtained. The chiral centers of the present invention can have the S or the R configuration.

In addition, atoms making up the ligands of the present invention are intended to include all isotopic forms of such atoms. Isotopes, as used herein, include those atoms having the same atomic number but different mass numbers. The mass number of the isotope is abbreviated either as $^{13}$C or C-13. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of the ligands may be replaced by a sulfur or selenium atom(s).

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

C. Preparation of Ligand and Physical Properties

1. Synthesis

In some embodiments, compound L may be synthesized as outlined in schemes 1 and 2 which are shown below. In some embodiments, a primary amine, for example, bis(3-aminopropyl)amine (1) is first protected with pthalic anhydride to give 3, which has secondary amine available for further conjugation. Then, in some embodiments, a commercially available lysine linker carrying a carbobenzyloxy (Cbz) protecting group on a amine and a tert-butyloxycarbonyl (BOC) protecting group on c amine 4 is attached to 3 via carbodiimide chemistry to give 5. Next, in some embodiments, the BOC protecting group of the resulting compound is removed to give 6 having free amine on 8 position. In some embodiments, the resulting primary amine is attached to the side arm of NOTA (7) to form 8 providing points of attachment for DOTA units and for targeting peptides. In some embodiments, the terminal amino groups are freed after the deprotection of the N-phthaloyl groups of 8 via hydrazine treatment to give 9. Next, in some embodiments, the DOTA units are conjugated to 9 through carbodiimide chemistry. In some embodiments, attempts to deprotect the BOC groups of compound 9 may lead to partial deprotection of the CBZ groups. In other embodiments, the molecule is fully deprotected. To this end, in some embodiments, the compound is treated with a 30% solution of HBr in acetic acid solution or other similar acidic solutions. In some embodiments, this reaction may lead to full deprotection. Finally, in some embodiments, the final compound is achieved by remove all BOC protecting groups using a TFA solution or other similar acidic solutions.

Scheme 1. Synthesis of lysine derivative for attachment for NOTA side arm on which DOTA pendants can be attached

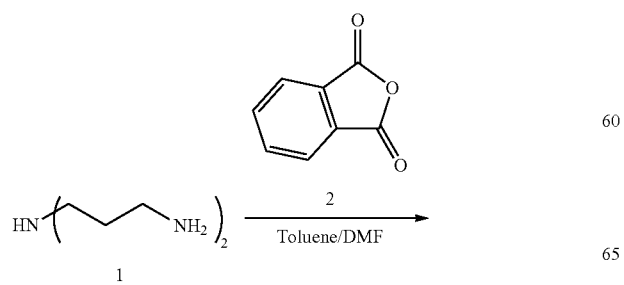

Scheme 2. Synthesis of NOTA containing six DOTA units

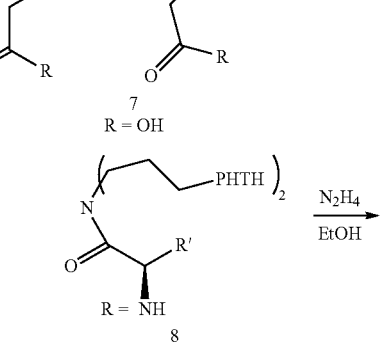

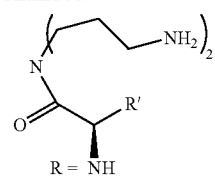

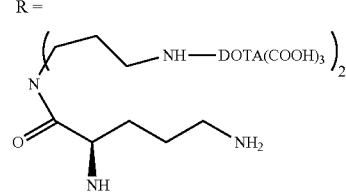

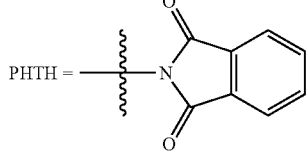

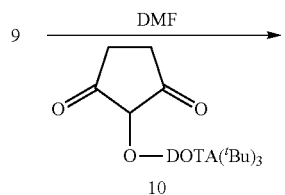

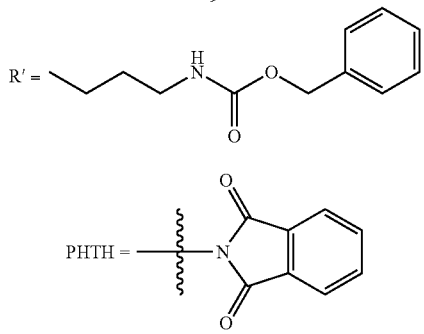

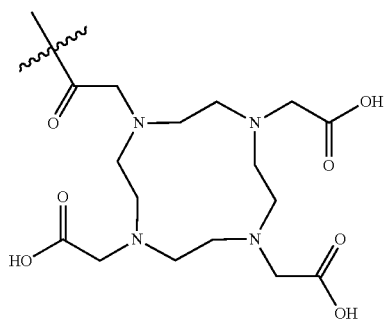

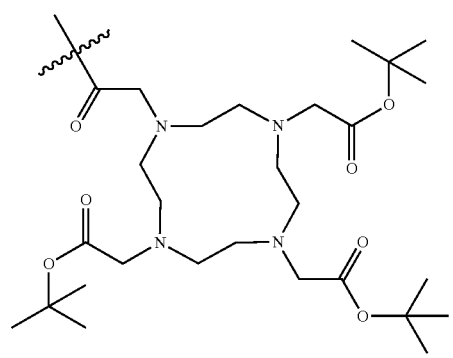

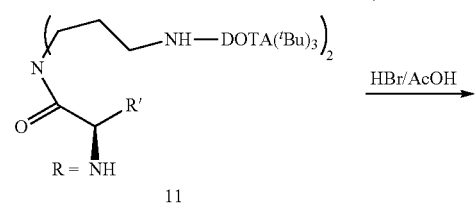

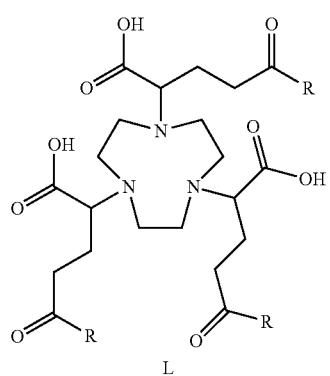

2. Complexation with $Gd^{3+}/Ga^{3+}$

As indicated by the thermodynamic stabilities ($logK_{Gd-DOTA}=24.7$; $logK_{Gd-NOTA}=14.3$; $logK_{Ga-NOTA}=31.0$) (Caravan, et al., 1999) and without being bound by theory, in some embodiments, the complex of L with $Ga^{3+}$ and $Gd^{3+}$ is formed in the NOTA and DOTA units, respectively. For example, the $Gd^{3+}$ complex may be formed in the DOTA units by adding six equivalence of $Gd^{3+}$ followed by incorporating $Ga^{3+}$ into the NOTA core. Therefore, in some embodiments, the reaction is performed using an excess of $Gd^{3+}$, which will result in chelation of $Gd^{3+}$ with both NOTA and DOTA units. In some embodiments, this complex is challenged with excess of DTPA or other similar ligands with log $K_{Gd}$. Because Log K of Gd-DTPA complex (Reichert, et al., 1996) is about eight orders of magnitude higher than that of Gd-NOTA complex, in some embodiments, the $Gd^{3+}$ ion is removed from the NOTA core through the exchange process with any ligand of higher affinity. In some embodiments, the Gd-DTPA is removed from the solution by HPLC or other separatory techniques. In some embodiments, the $Ga^{3+}$ labeling of the $Gd^{3+}$ complex is carried out at pH 3-5 in HEPES buffer.

3. Relaxometric Studies

In some embodiments, MRI contrast agents is typically characterized by a $T_1$ proton relaxivity value. The relaxivity of low molecular weight Gd-ligand complex that has rapid water exchange kinetics may be dominated by the inner-sphere contribution. Without being bound by theory, the Solomon-Bloembergen-Morgan (SBM) theory of relaxivity predicts that inner-sphere contribution to relaxivity may be dependent on several parameters including the number of inner-sphere water molecules (q), the longitudinal relaxation time of the protons of the water molecule(s) in the inner coordination sphere, the residence time of the inner-sphere water molecule(s) and the tumbling rate of the paramagnetic complex in solution (rotational correlation time) (Caravan, et al., 1999). In some embodiments, the relaxivity of $Gd^{3+}$-L is between 90 and 110±15 mM$^{-1}$ s$^{-1}$. In some embodiments, each Gd in the complex accounts for relaxivity of 15 to 25 mM$^{-1}$ s$^{-1}$, while under the same conditions the relaxivity of Gd(DOTA) complex is about 2-5 mM$^{-1}$ s$^{-1}$. In some embodiments, the relaxivity value of Gd$^{3+}$-L is about several times greater than that of Gd(DOTA). In some cases, the relaxivity value may be 400% higher. In some embodiments but without being bound by theory, this is attributed to its higher molecular weight (larger size) and consequently longer rotational correlation time (tR). In some embodiments, at ambient conditions (37° C.), the relaxivity value of Gd$^{3+}$-L may remain unchanged, decrease or increase. In some embodiments, the relaxivity value remains unchanged. In some embodiments, the measurement of the relaxivity value of Gd$^{3+}$-L in serum, including but not limited to rat serum, at 25° C. may gave an enhanced relaxivity value of 120 to 160 mM$^{-1}$ s$^{-1}$.

4. MRI Imaging and Relaxivity Measurements

For gadolinium-based MRI contrast agents, the imaging may be performed on 0.5 mL microfuge tubes containing standards at various concentrations of probe Gd$^{3+}$-L in 7.0 T at 25° C. In some embodiments, the efficacy of the probe is measured by the longitudinal relaxation rate of the water protons in a various concentration of Gd$^{3+}$-L solution, which is known as relaxivity ($r_1$) (Shiraishi, et al., 2010; Huang, et al., 2011) or the measurement of other physical parameters. Without being bound by theory, according to the Bloembergen-Solomon-Morgan theory, in some embodiments, the residence lifetime of the coordinated water molecules and the rotational correlation times are factors for enhancing the relaxivities of gadolinium complexes, which are related to the intrinsic structural parameters. In some embodiments, the relaxation theory also predicts that higher relaxation rates can be obtained upon increase of the rotational correlation time of complexes. In some embodiments, small, fast tumbling molecules like Gd-DTPA show a modest decrease in $r_1$ with increasing field strength (Rohrer, et al., 2005), while big molecular weight contrast agent have high relaxivities that peak between 0.5 and 1.0 T and then sharply drop with increasing field (Rohrer, et al., 2005; Caravan, 2006).

D. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

1. Example 1: Synthetic Scheme Experimental Procedures a. Compound 3

Bis(phthalimidylpropyl)amine (3) was synthesized following a previously published report (Kang, et al., 2009; which is incorporated herein by reference) Quickly, phthalic anhydride (5.0 g, 33.8 mmol) was added to a solution of bis(3-aminopropyl)amine (1) (2.03 g, 15.5 mmol) in toluene/DMF (50 mL/5 mL). The reaction mixture was stirred under reflux for 24 hours. The solvent was then evaporated and EtOH (100 mL) added to the residue. The resultant mixture was stirred for 5 hours, and the precipitate filtered, and dried to give the compound 7 (yield: 75%). $^1$H NMR (400 MHz, CDCl$_3$): δ=7.83 (m, 4H), 7.70 (m, 4H), 3.75 (t, J=6.8 Hz, 4H), 2.62 (t, J=6.8 Hz, 4H), 1.84 (quintet, J=6.8 Hz, 4H).

b. Compound 5

To a solution of protected lysine 4 (2.0 g, 5.3 mmol) in THF (10 mL) was added the pthalimide protected secondary amine 3 (2.1 g, 5.3 mmol), dicyclohexylcarbodiimide (1.1 g, 5.5 mmol) and triethylamine (0.6 g, 5.5 mmol). The resultant solution was stirred for 24 hours, filtered and the solvent evaporated. The crude product was purified by flash chromatography (ethyl acetate/hexane 1:1) to give lysine derivative 5 (2.3 g, 3.0 mmol, 57%) as a white solid. $^1$H NMR (400 MHz, CDCl$_3$): δ=7.65 (m, 3H), 7.54 (m, 3H), 7.18 (m, 4H), 5.47 (m, 1H), 5.27 (m, 1H), 4.94 (m, 1H), 4.36 (m, 1H), 3.72-3.34 (m, 6H), 3.23-2.89 (m, 4H), 2.03-1.63 (m, 5H), 1.62-1.35 (m, 4H), 1.33-1.11 (m, 10H). $^{13}$C NMR (100 MHz, CDCl$_3$): δ 172.5, 168.3, 168.1, 156.4, 155.4, 136.7, 133.8, 131.9, 128.3, 127.9, 127.8, 123.2, 123.1, 79.3, 66.2, 49.6, 45.6, 43.9, 40.6, 35.6, 35.3, 33.1, 30.1, 30.5, 29.5, 29.1, 28.6, 28.2, 26.9, 22.4. MS (MALDI) m/z calcd for C$_{41}$H$_{47}$N$_5$O$_9$: 753.3; found. 754.8 ([M+H]$^+$).

c. Compound 6

To a solution of lysine derivative 5 (2.3 g, 3.0 mmol) was added trifluoroacetic acid (10 mL) and the solution was allowed to stir for 12 hours. The solvent evaporated and the crude product was purified by flash chromatography (ethyl acetate) to give amine 6 (1.8 g, 2.8 mmol, 93%) as a white solid. $^1$H NMR (400 MHz, CDCl$_3$): δ=7.73 (m, 3H), 7.61 (m, 3H), 7.23 (m, 4H), 5.87 (m, 1H), 5.58 (m, 1H), 4.97 (m, 1H), 4.40 (m, 1H), 3.72-3.37 (m, 6H), 3.35-2.82 (m, 4H), 2.10-1.68 (m, 5H), 1.59-1.29 (m, 4H). $^{13}$C NMR (100 MHz, CDCl$_3$): δ 169.1, 168.3, 156.8, 136.7, 134.1, 133.9, 131.8, 131.7, 128.4, 127.9, 123.3, 123.2, 66.4, 50.7, 45.5, 43.8, 40.1, 35.5, 35.1, 30.8, 29.7, 29.1, 27.7, 26.5, 21.4. MS (MALDI) m/z calcd for C$_{36}$H$_{39}$N$_5$O$_7$: 653.3; found. 654.8 ([M+H]$^+$).

d. Compound 8

To a solution of protected acid 7 (0.1 g, 0.15 mmol) in acetonitrile (1.0 mL) was added the deprotected amine 3 (0.4 g, 0.6 mmol), dicyclohexylcarbodiimide (0.15 g, 0.83 mmol) and triethylamine (0.3 g, 0.27 mmol). The resultant solution was stirred for 12 hours, filtered and the solvent evaporated. The crude product was purified by flash chromatography (ethyl acetate) to give NOTA derivative 8 (0.26 g, 0.1 mmol, 67%) as a white solid. $^1$H NMR (400 MHz, CDCl$_3$): δ 8.73 (bs, 6H), 7.71 (m, 12H), 7.61 (m, 12H), 7.23 (m, 15H), 5.56 (bs, 2H), 4.99 (m, 5H), 4.74 (m, 3H), 3.79-3.27 (m, 24H), 3.25-2.77 (m, 13H), 2.60-2.17 (m, 4H), 2.15-1.71 (m, 12H), 160 (m, 4H), 1.38 (m, 43H). $^{13}$C NMR (100 MHz, CDCl$_3$): δ 172.5, 168.3, 156.8, 136.5, 134.1, 133.9, 131.8, 128.4, 127.9, 123.3, 123.2, 79.0, 69.8, 66.5, 64.8, 49.3, 45.9, 44.3, 40.5, 35.5, 35.3, 325, 32.2, 29.3, 28.3, 27.9, 26.8, 22.6. MS (MALDI) m/z calcd for C$_{141}$H$_{168}$N$_{18}$O$_{30}$:2594.2; found. 2595.9 ([M+H]$^+$).

e. Compound 9

To a solution of nota lysine derivative 8 (0.26 g, 0.1 mmol) in ethanol (1 mL) was added hydrazine monohydrate (0.1 mL, 2.0 mM) and the mixture was stirred for 12 h at room temperature. After the reaction, the precipitate was removed by filtration. The filtrate was evaporated and extracted with $CH_2Cl_2$ (3×10 mL). The combined organic layers were evaporated to give light yellow oil 9 (0.15 g, 0.08 mmol, 80%). This compound was used for the next step without further purification. $^1$H NMR (400 MHz, $CD_3OD$): δ 7.31 (s, 15H), 4.99 (m, 6H), 4.66 (m, 3H), 3.68-3.39 (m, 10H), 3.38-3.31 (m, 6H), 3.20-2.94 (m, 17H), 2.93-2.72 (m, 9H), 2.65-2.30 (m, 7H), 1.95-1.81 (m, 6H), 1.78-1.57 (m, 6H), 1.55-1.20 (m, 44H). $^{13}$C NMR (100 MHz, $CD_3OD$): δ 173.7, 173.1, 157.6, 136.9, 128.9, 127.3, 126.8, 126.5, 82.6, 77.3, 65.9, 64.5, 50.2, 48.8, 45.9, 44.5, 42.3, 38.5, 38.1, 36.7, 30.3, 29.1, 27.8, 26.6, 25.2 MS (MALDI) m/z calcd for $C_{93}H_{156}N_{18}O_{18}$: 1814.1; found. 1815.8 ($[M+H]^+$).

f. Compound 11

To a solution of the amine 9 (0.15 g, 0.08 mmol) in DMF (1 mL) was added N-hydroxysuccinimide ester of DOTA 10 (0.53 g, 0.8 mM) and the mixture was stirred for 24 h at room temperature. The solvent was evaporated and the product purified by reverse phase HPLC using water and acetonitrile solvent mixture to give 11 as a white solid (0.29 g, 0.06 mmol, 70%). $^1$H NMR (400 MHz, $CDCl_3$): δ 7.40-7.18 (s, 15H), 5.15-4.99 (m, 6H), 4.71 (m, 6H), 4.38-4.83 (m, 26H), 3.82-3.36 (m, 61H), 3.30-2.62 (m, 17H), 2.60-2.30 (m, 12H), 2.23-1.98 (m, 10H), 1.99-1.80 (m, 10H), 1.79-0.96 (m, 174H). $^{13}$C NMR (100 MHz, $CD_3OD$): δ 172.8, 172.6, 170.8, 170.6, 157.3, 137.2, 128.2, 127.6, 127.2, 84.5, 81.5, 65.8, 64.7, 53.6, 51.6, 49.2, 48.5, 45.3, 43.6, 42.0, 40.1, 36.5, 31.9, 27.2, 28.5, 27.2, 27.1, 22.7. MS (MALDI) m/z calcd for $C_{261}H_{456}N_{42}O_{60}$: 5139.4; found. 5140.7 ($[M+H]^+$).

g. Compound L

To a solution of DOTA derivative 11 (0.10 g, 0.02 mmol) was added 30% HBr in AcOH (2 mL) and the solution was allowed to stir for 4 hours. The solvent was evaporated, the product neutralized and purified by reverse phase HPLC using water and acetonitrile solvent mixture to give L as a white solid (0.06 g, 0.02 mmol, 75%). $^1$H NMR (400 MHz, $CD_3OD$): δ 4.42-3.62 (m, 89H), 3.59-3.32 (m, 67H), 3.24-2.85 (m, 48H), 2.80-2.30 (m, 22H), 2.34-2.03 (m, 17H), 2.06-1.85 (m, 14H), 1.88-1.65 (m, 20H), 1.65-1.39 (m, 11H), 1.31 (m, 6H) δ MS (MALDI) m/z calcd for $C_{153}H_{270}N_{42}O_{54}$: 3561.9; found. 3562.4 ($[M+H]^+$).

h. $Gd^{3+}$-L Complex

The free ligand L (0.06 g, 0.016 mmol) was dissolved in water (1 mL) and the pH was adjusted to 7 with NaOH (0.1 M). To this solution was added excess of $GdCl_3.6H_2O$ and the pH was again adjusted to 6.5 and allowed to stir at room temperature overnight. The pH was raised above 8 using 1 M aqueous NaOH, which caused the excess $Gd^{3+}$ to precipitate as $Gd(OH)_3$. The solution was filtered and the pH was readjusted to 7 using 1 M HCl. To the resulting solution, diethylene triamine pentaacetic acid (DTPA) (0.1 mM, 1 mL), was added and the solution was purified using HPLC to give the desired complex. The desired fractions were pooled together and lyophilized to give a white solid. (0.04 g, 0.009 mmol, 54%). MS (MALDI) m/z calcd for $C_{153}H_{264}Gd_6N_{42}O_{60}$: 4489.3; found. 4634.9 ($[M+K+6H_2O]^+$).

i. Cold $Ga^{3+}(Gd^{3+}$-L) Complex

The gadolinium complex, $Gd^{3+}$-L (0.001 g, 0.225 µmol) was dissolved in a solution of 4-(2-hydroxyethyl)-1-piperazineethanesulfonic acid (HEPES, pH=6.5, 1 M, 1 mL). To the resulting solution was added a solution of $GaCl_3$ (0.1 mg, 0.567 µmol) in 0.6 N HCl (0.3 mL) and the resulting solution was stirred for 1 h. To the mixture was added 500 µL of 5 mM ethylendiaminetetraacetic acid (EDTA) and the mixture, was allowed to incubate for another 5 min (EDTA was used to remove nonspecifically bound or free $GaCl_3$ from the Ga-labeled complex). The purification of Ga-labeled complex was carried out by passing the mixture through a preconditioned Sep-Pak C-18 heavy cartridge. After thorough rinsing (3×5 mL, water) of the cartridge, the Ga-labeled complex was eluted by an ethanol/water mixture (70:30). The product was purified with HPLC and characterized by mass spec. MS (MALDI) m/z calcd for $C_{153}H_{264}GaGd_6N_{42}O_{60}$: 4555.28; found. 4556.9 ($[M+H]^+$).

j. $Ga^{3+}$-68($Gd^{3+}$-L) Complex

In a 1.5 mL eppendorf tube, a solution containing 10 µg $Gd^{3+}$-L complex in 1 mL of HEPES (pH=6.5), was added a solution of 97 MBq of Ga-68$Cl_3$ in 0.6 N HCl. The reaction mixture was shaken and incubated at 75° C. for 0.5 h. To this solution, was added DTPA (5 mM, 5 µL) and the reaction mixture was incubated for 5 min (EDTA was used to remove nonspecifically bound or free Ga-68 from the Ga-68-labeled conjugate). The Ga-68-labeled conjugate was purified by passing the mixture through a preconditioned Sep-Pak C-18 light cartridge. After thorough rinsing (3×3 mL, water) of the cartridge, the Ga-68-labeled conjugate was eluted by an ethanol/water mixture (70:30). The product was first analyzed by a Rita Star Radioisotope TLC Analyzer (Straubenhardt, Germany) on instant thin-layer chromatography (ITLC-SG) plates (Pall Life Sciences, East Hills, N.Y.) and then by radio-HPLC to determine the radiochemical purity of the product.

2. Example 2: Physical Property and Biological Distribution Studies a. Relaxivity Measurements The T1 values were recorded at 23 MHz (0.5 T), 25° C. by using a Maran Ultra relaxometer (Oxford Instruments, UK). Longitudinal relaxation times were measured by using the inversion-recovery pulse sequence (180°-t-90°). The T1 relaxivities were determined by the linear regression analysis of the water proton relaxation rates in solutions ranging in concentration from 0.005 to 12 mM, in Millipore water in triplicate. At 20 MHz, 25° C., the relaxivity of $Gd^{3+}$-L was calculated to be 103.5±15 $mM^{-1}$ $s^{-1}$. Thus, each Gd in the complex accounts for relaxivity of 17.25 $mM^{-1}$ $s^{-1}$, while under the same conditions, the relaxivity of Gd(DOTA) complex is 3.5 $mM^{-1}$ $s^{-1}$. The relaxivity value of $Gd^{3+}$-L is approximately 400% higher than that of Gd(DOTA). This may be attributed to its higher molecular weight (larger size) and consequently longer rotational correlation time (tR). At ambient conditions (37° C.), the relaxivity value of $Gd^{3+}$-L remains unchanged. The measurement of the relaxivity value of $Gd^{3+}$-L in rat serum at 25° C. gives an enhanced relaxivity value of 145.5±9.2 $mM^{-1}$ $s^{-1}$.

b. MRI Imaging and Relaxivity Measurements at 7.0 T

The $T_1$-weighted MR images of samples in 0.5 mL microfuge tubes were collected using Agilent®/Varian™ 7.0 T (400 MHz, 5 cm diameter volume coil) VNMRj's spin-echo sequence (SEMS) sequence. For imaging, the following parameters were used: TR=200 ms; effective echo time (TE)=11.5 ms; FOV 45×45 mm$^2$, data matrix=256×256, averaging=2, slice=1 mm, steady-state scans=5, single slice. The T1-maps of the samples at 9.4 T was determined from a series of multi-TR (0.005 s to 10 s) saturation-recovery spin-echo sequence (SEMS with minimum TE (11.5 ms); FOV 45×45 mm$^2$; matrix=128×128; averaging=5, steady state scans=5), fitted and calculated using the ImageJ software. All the fits for T1 values used to calculate the longitudinal relaxivity, r1, had fitting coefficients, R$^2 \geq 0.99$. Three trials were performed. A representative data of the image acquired is shown in FIG. 1. FIG. 1 shows the images of five formulations. The images of the probe Gd$^{3+}$-L were significantly brighter than that of magnevist (4.1 mM$^{-1}$ S$^1$). Since the molecular rotation correlation time is proportional to the molecular size (Carvan, et al., 1999), the attachment of low molecular weight paramagnetic gadolinium-chelates to a molecular backbone may considerably enhance the relaxivity of the chelate unit (Kobayashi, et al, 2006), increasing r$_1$ values of the Gd(III)-labeled complex to 54.5 mM$^{-1}$ S$^{-1}$. There is a drastic decrease in the relaxivity of the probe with the increase in the field strength. Such changes are well known that T$_1$ relaxivity typically decreases with increasing field strength (Caravan, et al., 1999).

c. Biodistribution and Pharmacokinetics Studies of Ga$^{3+}$-68(Gd$^{3+}$-L) Complex Male BALB/C mice were injected with 300 µCi of Ga$^{3+}$-68(Gd$^{3+}$-L) complex to evaluate the tissue distribution of the tracer in mice. Mice were sacrificed 1 h, 4 h, 24 h, and 48 h post injection (p.i.). The organs of interest (blood, heart, lung, liver, spleen, kidney, stomach, muscle, fat, small intestine, large intestine, and brain) were harvested, weighed, and radioactivity was quantified using a γ-counter. Standards were prepared and counted along with the tissue samples to calculate the percentage-injected dose per gram (% ID/g). To determine the pharmacokinetic parameters, mice injected with the tracer were blood sampled from the retro-orbital sinus at 2 min, 5 min, 10 min, 30 min, 1 h, 2 h, 24 h, and 48 h p.i. and quantified using a γ-counter. The pharmacokinetic parameters were calculated based on a two-compartment open model.

The results showed that the Ga$^{3+}$-68(Gd$^{3+}$-L) complex exhibited a two-compartment profile of in vivo kinetics with at t$_{\alpha 1/2}$ of 11.3 min, and a t$_{\beta 1/2}$ of 7.3 h. The short t$_{\alpha 1/2}$ of Ga$^{3+}$-68(Gd$^{3+}$-L) indicates that the probe can rapidly distribute into tissues during the circulation, similar to those of reported molecular imaging agents (Caravan, et al., 1999) but different from nanoparticle-based probes (Ma, et al., 2008; Lux, et al., 2011) The relatively long t$_{\beta 1/2}$ of Gd$^{3+}$-L is further indication that Ga$^{3+}$-68(Gd$^{3+}$-L) indeed behaves like small molecular probes in pharmacokinetics.

Figure 2:
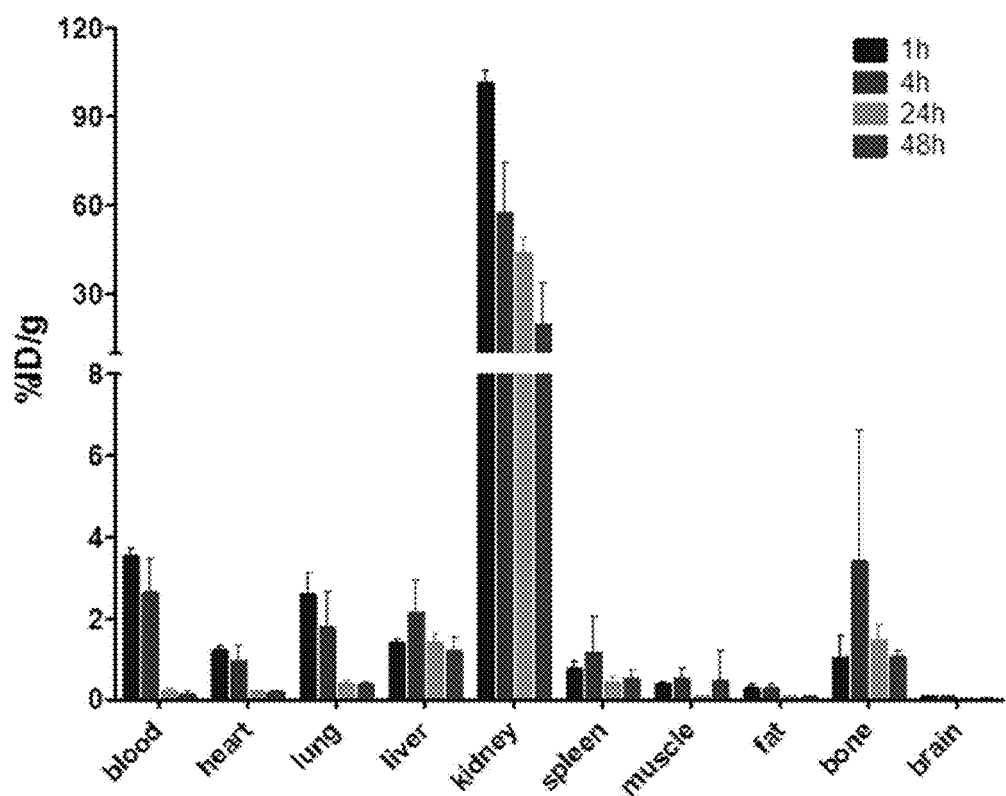

Biodistributions of Ga$^{3+}$-68(Gd3+-L) in kidney, liver, spleen and intestines at 5 min, 1, 4, 24, and 48 h after IV injection also provide additional insights on the clearance pathways and kinetics (FIG. 2).

The highest accumulation of the Ga$^{3+}$-68(Gd3+-L) occurred within 1 hour p.i. followed by efficient clearance. This observation is consistent with the measured short t$_{\alpha 1/2}$, indicating that the tissue distribution of the probe was indeed rapid. The highest uptake Ga$^{3+}$-68(Gd$^{3+}$-L) in the kidney was followed by a gradual decrease from about 100% of the injected dose per gram (ID/g) to about 20% of ID/g (FIG. 2), which was in agreement with the clearance of the probe from blood, indicating that the probe was mainly excreted through the kidney. Without being bound by theory, the high renal uptake can be attributed to the net positive charge on the probe due the presence of amine groups. The high kidney uptake due to the presence of an amine on the molecule has been shown with other positively charged compounds (Behr, et al., 1998). In some embodiments of the present invention, the free amines may be utilized for attaching targeting groups or additional DOTA moieties to further enhance the relaxivity of the probe, thereby negating the positive charge on the free amine.

The serum stability test and the urine sample analysis showed that Ga$^{3+}$-68(Gd$^{3+}$-L) remained intact within 48 h without demetallization.

d. In Vitro and In Vivo Stability

The in vitro stability test was performed in the rat serum. Briefly, Ga$^{3+}$-68(Gd$^{3+}$-L) complex (300 µCi, 5 µL) was added into 100 µL of rat serum (n=3). The solution was incubated for 1 h, 4 h, 24 h, and 48 h incubation at 37° C., respectively. The solution was vortexed and centrifuged for 5 min at 21,000 g. The supernatant was then analyzed by HPLC. For the in vivo stability evaluation, male mice were injected with 600 µCi of Ga$^{3+}$-68(Gd$^{3+}$-L) complex in 100 µL of saline via the tail vein. The urine samples were collected within 1 h, 4 h, 24 h, and 48 h p.i., and then analyzed by HPLC.

4. Example 3: Synthetic Scheme Experimental Procedures

Figure 3:
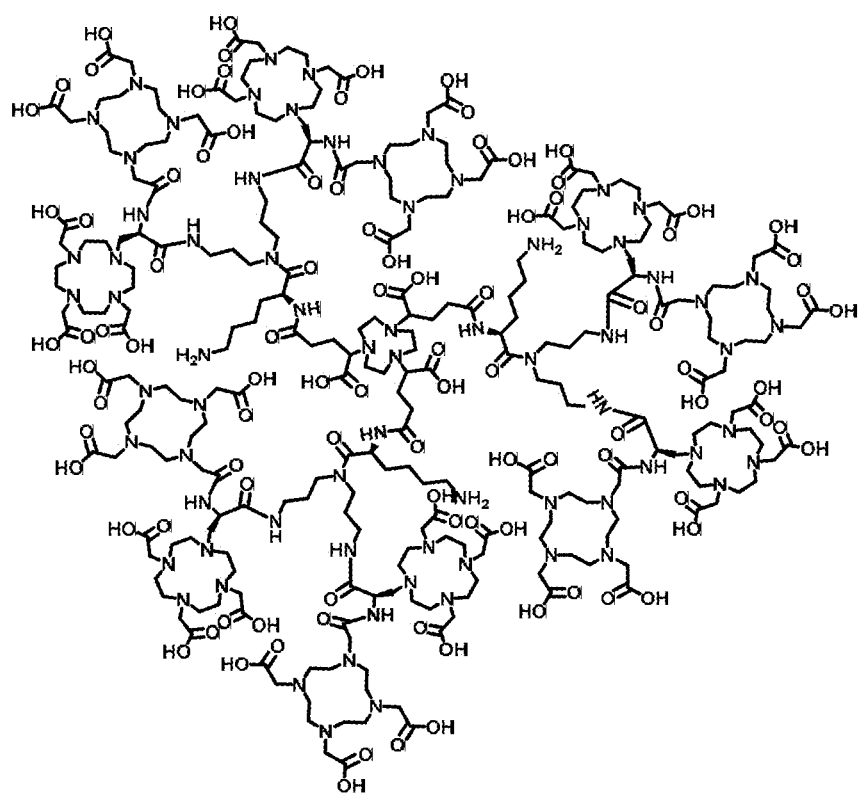
FIG. 3. The structure of variant of ligand L.
Figure 4A:
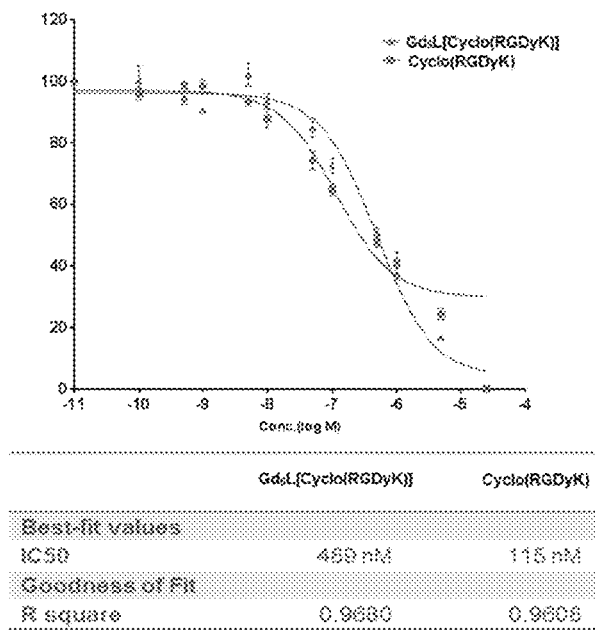
FIGS. 4A-B. The calculated $IC_{50}$ values of synthesized probes (FIG. 4A) $Gd_6L[Cyclo(RGDyK)]_3$ and (FIG. 4B) $Gd_6L[PEG_{12}Cyclo(RGDyK)]_3$.
Figure 4B:
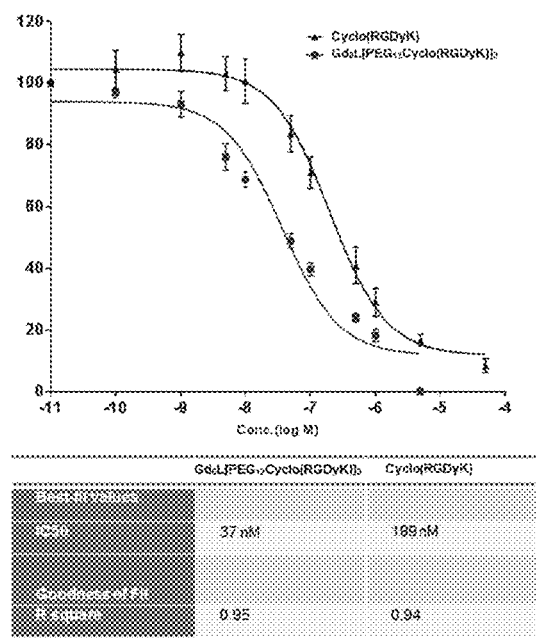
Figure 5:
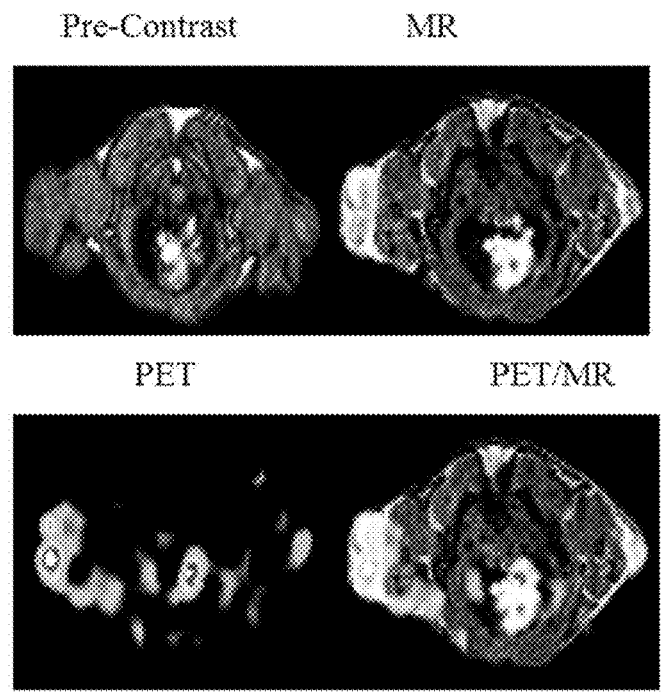
FIG. 5. Representative in vivo MR and PET/MR images of U87MG tumor bearing mice 1 h post injection obtained with $Gd_6L[PEG_{12}Cyclo(RGDyK)]_3Ga$-68.

The inventors, in an attempt to functionalize ligand L for target based imaging, introduced maleimido group to ligand L via carbodiimide coupling. The resultant compound L-(Mal)$_3$ is a versatile platform on which any targeting moiety carrying a thiol group can be conjugated by thiol-maleimide reaction. For proof of concept, they derivatized their platform with integrin alpha(v) beta3 targeting peptide c (RGDyK). For this c(RGDyK) was first modified with thiol (Cyclo(RGDyK)SH) and subsequently attached to L-(Mal)$_3$ to give L[Cyclo(RGDyK)]$_3$. Unfortunately, the binding affinity of the synthesized compound turned out to be suboptimal (FIG. 4A). To increase the binding affinity and to offset the steric hindrance faced by the targeting groups, linkers were introduced between ligand L and the targeting moiety. Maleimide carrying PEG-6 linker was introduced to ligand L. Unfortunately, L(PEG$_6$-Mal)$_3$ failed to yield clean product when conjugated to Cyclo(RGDyK) SH. Alternative strategy of adding linker to targeting agent was also followed. PEG-12 carrying c(RGDyK), decorated with thiol unit was synthesized (Cyclo(RGDyK)PEG$_{12}$SH) and attached to L-(Mal)$_3$. The binding affinity of the synthesized compound, L[PEG$_{12}$Cyclo(RGDyK)]$_3$, was found to be excellent (FIG. 4B). PET/MRI imaging performed using labeled compound, Gd$_6$L[PEG$_{12}$Cyclo(RGDyK)]$_3$Ga-68, shown in FIG. 5 shows that the present compound is excellent in generating PET as well as MRI contrast. Synthesis of another variant of ligand L was also attempted. The synthesis is underway and the proposed structure is shown in FIG. 3.

5. Example 4: Derivatization of Ligand L
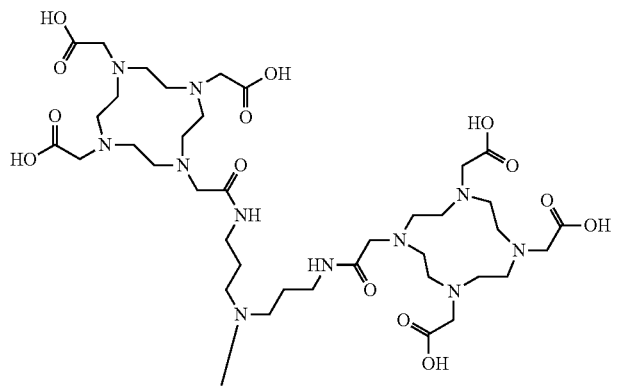
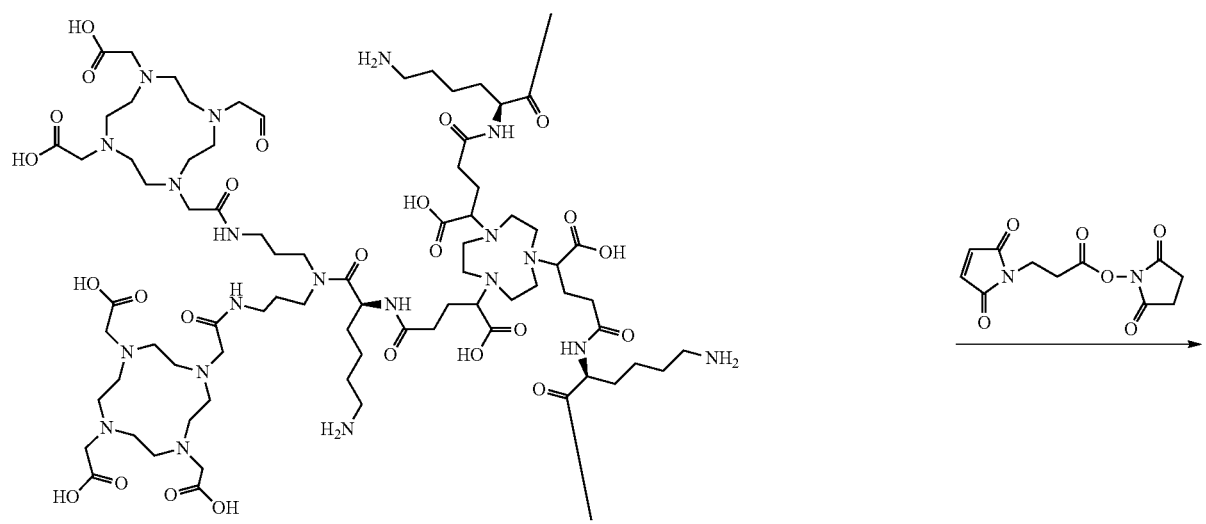
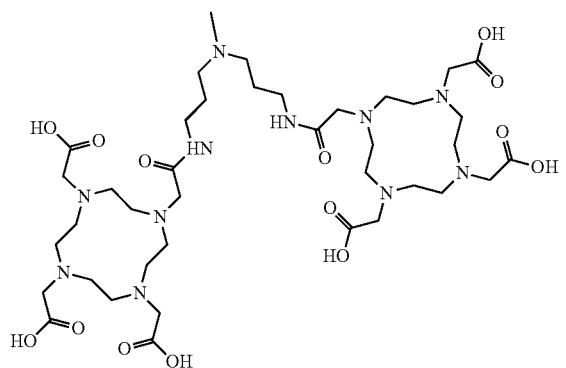
L

-continued
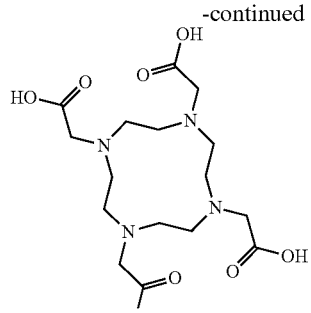
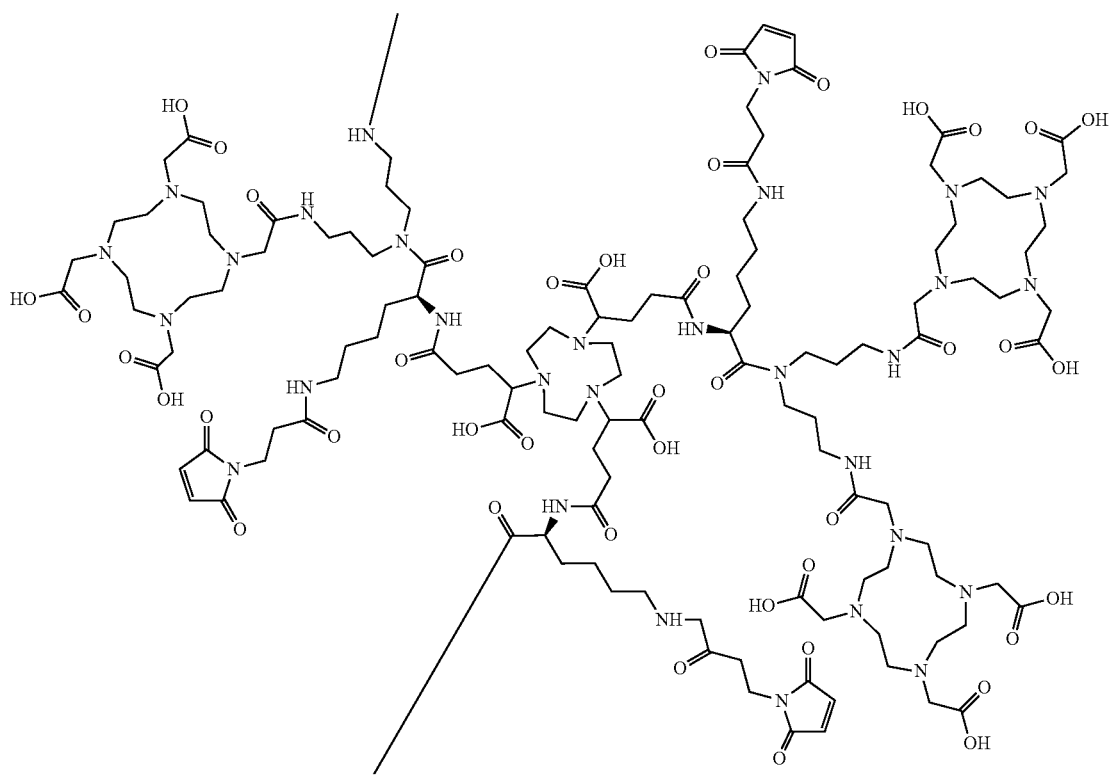
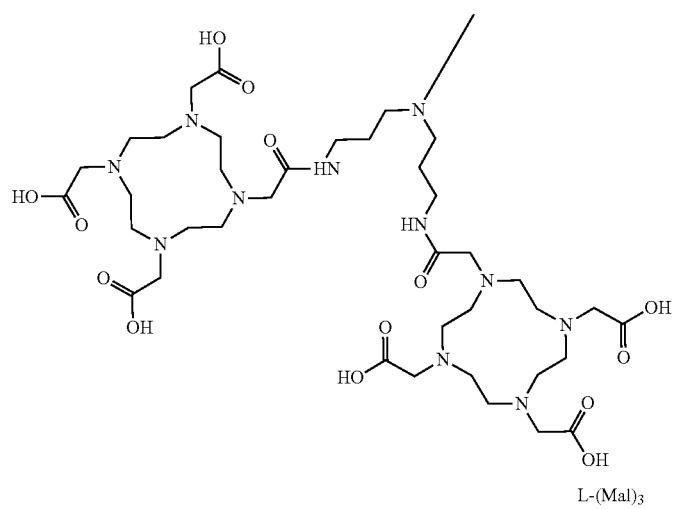
L-(Mal)₃

L(Mal)₃. To the free ligand L (0.20 g, 0.056 mmol) dissolved in DMF (1 mL) was added triethyl amine (0.022 g, 0.224 mmol) and N-(γ-Maleimidobutyryloxy)succinimide and the solution was allowed to stir for 24 h. The solvent was evaporated; the product neutralized and purified by reverse phase HPLC using water and acetonitrile solvent mixture to give L(Mal)₃ as a white solid. (0.10 g, 0.052 mmol, 45.1%). MS (MALDI) ink calc'd for $C_{174}H_{285}N_{45}O_{63}$: 4015.0; found. 4016.3 ([M+H]⁺).

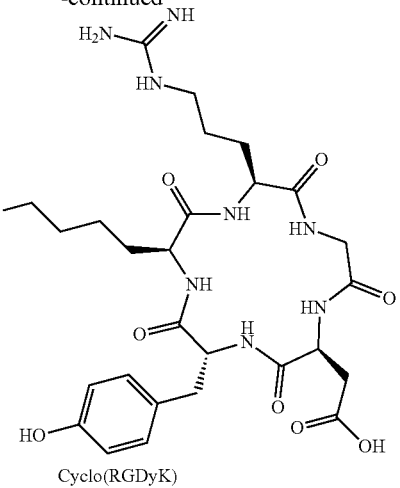

Cyclo(RGDyK)

Cyclo(RGDyK)SH. To the commercially available Cyclo (RGDyK) (0.03 g, 0.048 mmol) (Peptides International Inc, Kentucky) dissolved in DMF (1 mL) was added N-Succinimidyl 3-(2-pyridyldithio)-propionate (0.02 g, 0.064 mmol) (Thermo Scientific, IL) and the solution was allowed to stir for 6 h. The solvent was evaporated; the product neutralized and purified by reverse phase HPLC using water and acetonitrile solvent mixture and lyophilized. The resultant white solid was dissolved in DMF (1 mL) and Dithiothreitol (0.01 g, 0.065 mmol) was added and the solution was allowed to stir for 3 h. The solvent was evaporated; the product neutralized and purified by reverse phase HPLC using water and acetonitrile solvent mixture to give Cyclo (RGDyK)SH as a white solid. (0.10 g, 0.014 mmol, 29.5%). MS (MALDI) m/z calc'd for $C_{30}H_{45}N_9O_9S$: 707.3; found. 708.3 ([M+H]⁺).

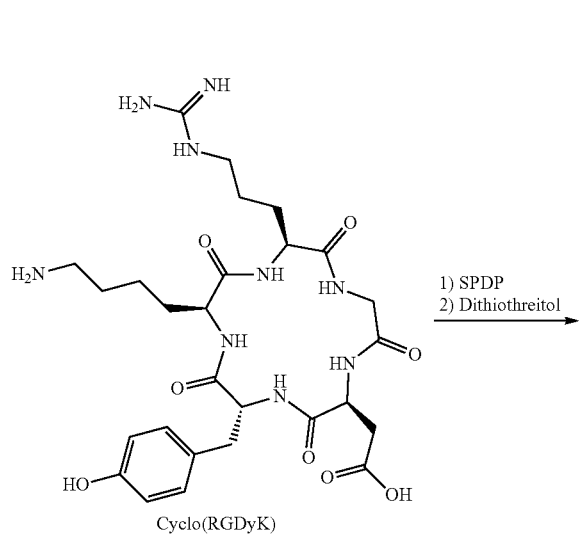

Cyclo(RGDyK)

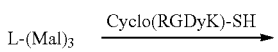

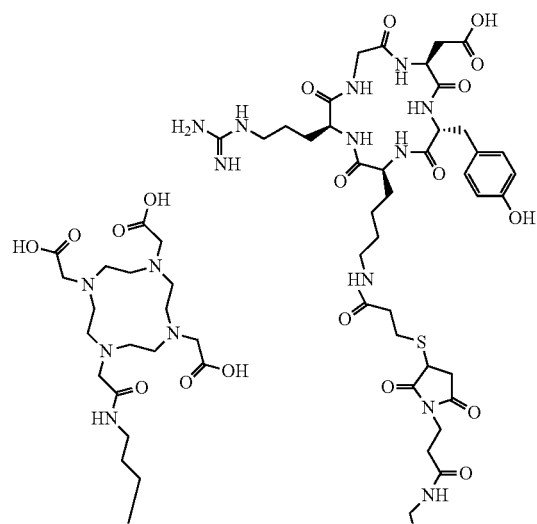

-continued

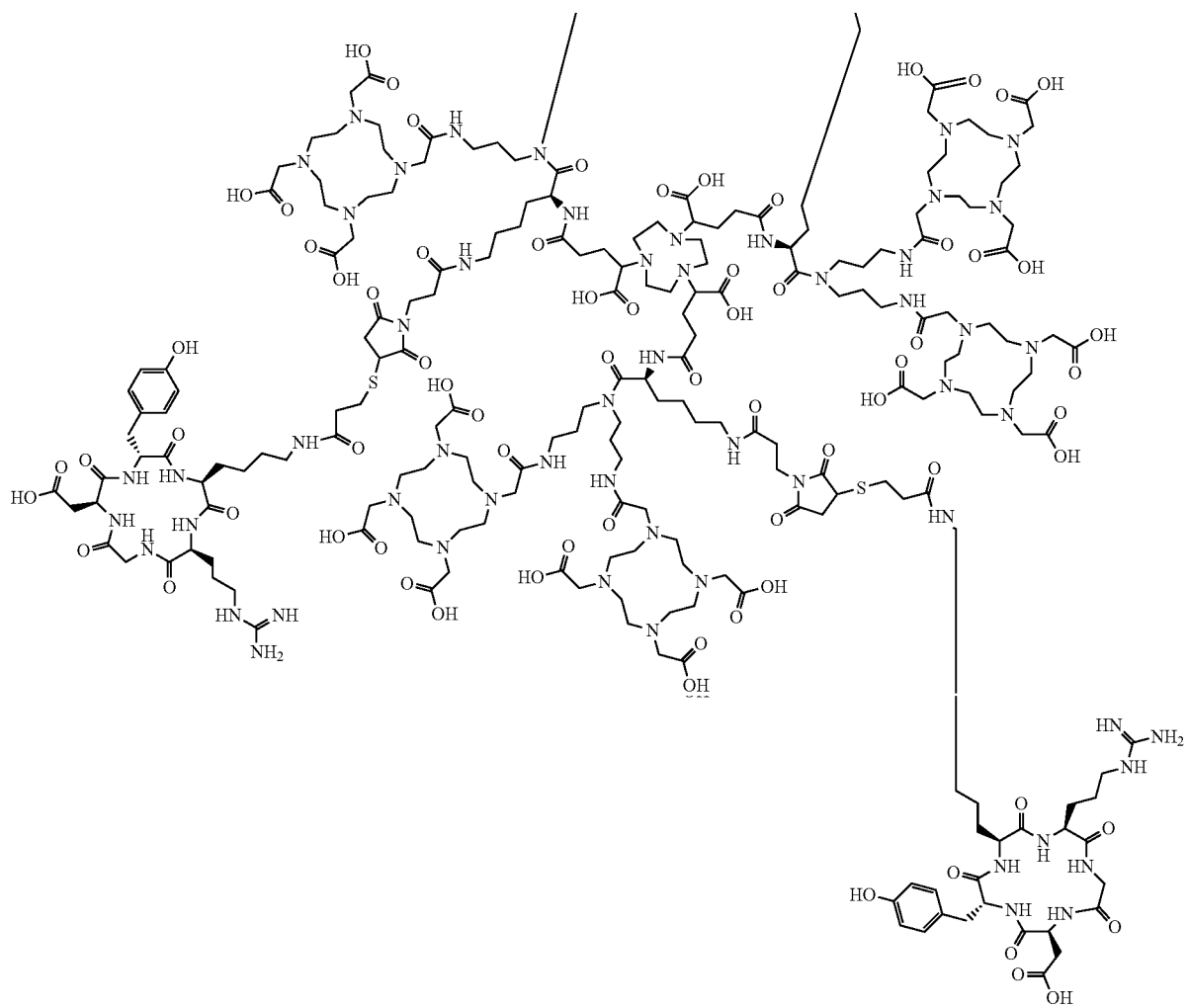

L[Cyclo(RGDyK)]$_3$. To the malemide carrying ligand, L(Mal)$_3$, (0.02 g, 0.005 mmol) dissolved in PBS (1×) was added the thiol carrying Cyclo(RGDyK)SH (0.014 g, 0.029 mmol) and the solution was allowed to stir for 18 h. The solution was purified by reverse phase HPLC using water and acetonitrile solvent mixture to give L[Cyclo(RGDyK)]$_3$ as a white solid. (0.010 g, 0.002 mmol, 33.3%). MS (MALDI) m/z calc'd for C$_{264}$H$_{420}$N$_{72}$O$_{90}$S$_3$: 6136.9; found. 6139.1 ([M+H]$^+$).

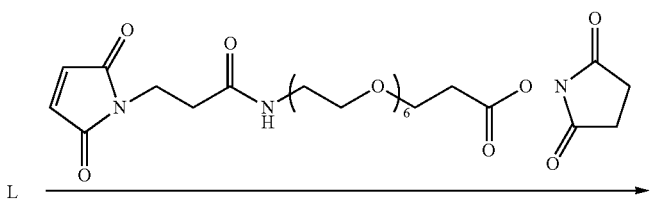

-continued

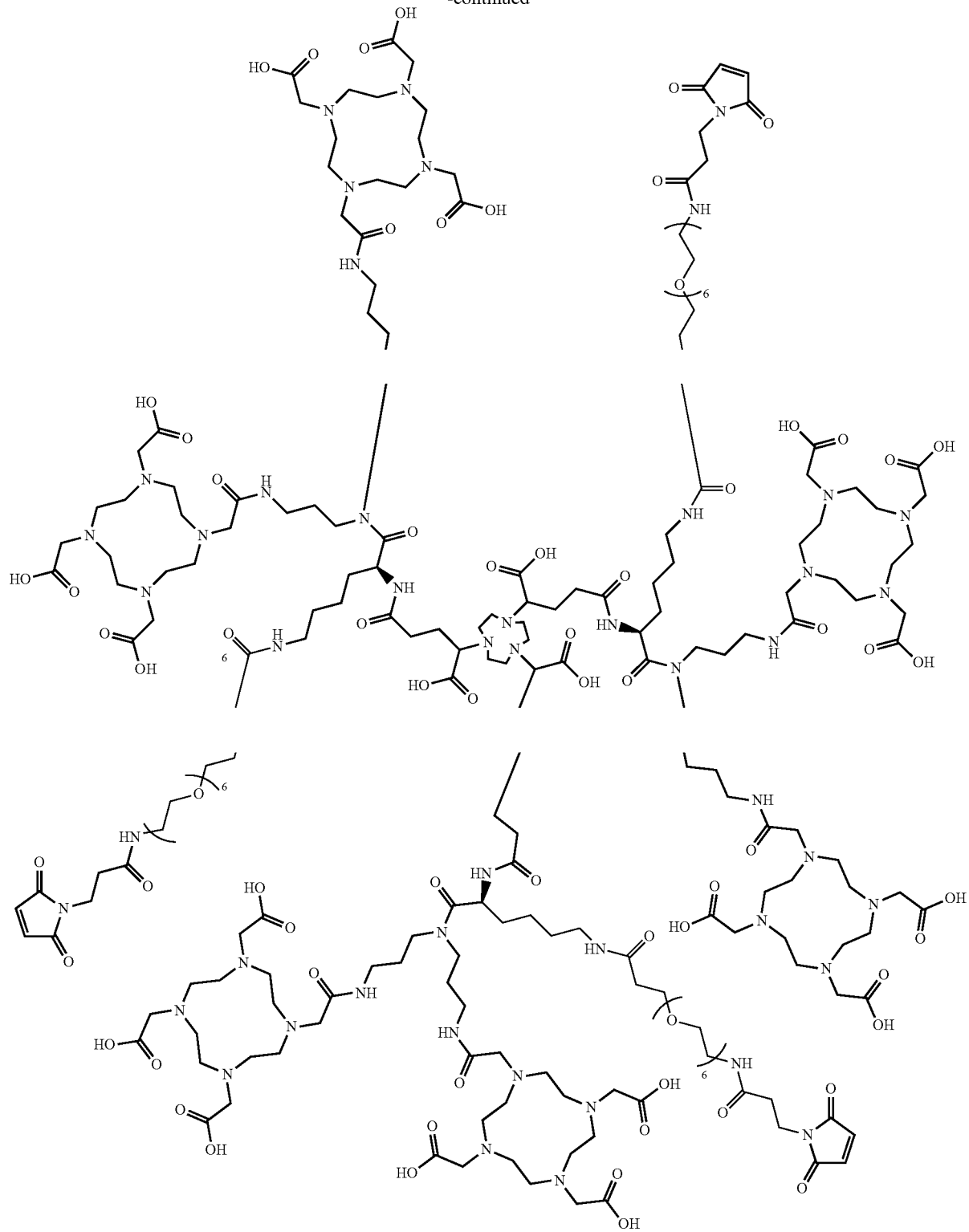

L(PEG$_6$-Mal)$_3$. To the free ligand L (0.150 g, 0.042 mmol) dissolved in DMF (1 mL) was added triethyl amine (0.022 g, 0.224 mmol) and MAL-PEG$_6$-NHS and the solution was allowed to stir for 24 h. The solvent was evaporated; the product neutralized and purified by reverse phase HPLC using water and acetonitrile solvent mixture to give L(PEG$_6$-Mal)$_3$ as a white solid. (0.084 g, 0.017 mmol, 40.1%). MS (MALDI) ink calc'd for $C_{219}H_{372}N_{48}O_{84}$: 5021.6; found. 5022.6 ([M+H]$^+$).

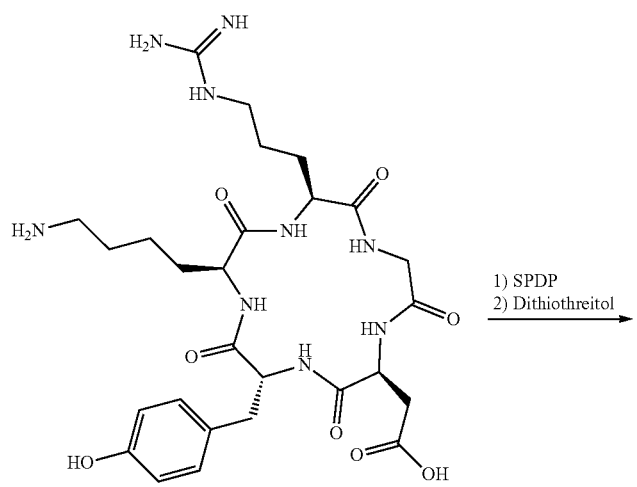

Cyclo(RGDyK)

1) SPDP
2) Dithiothreitol

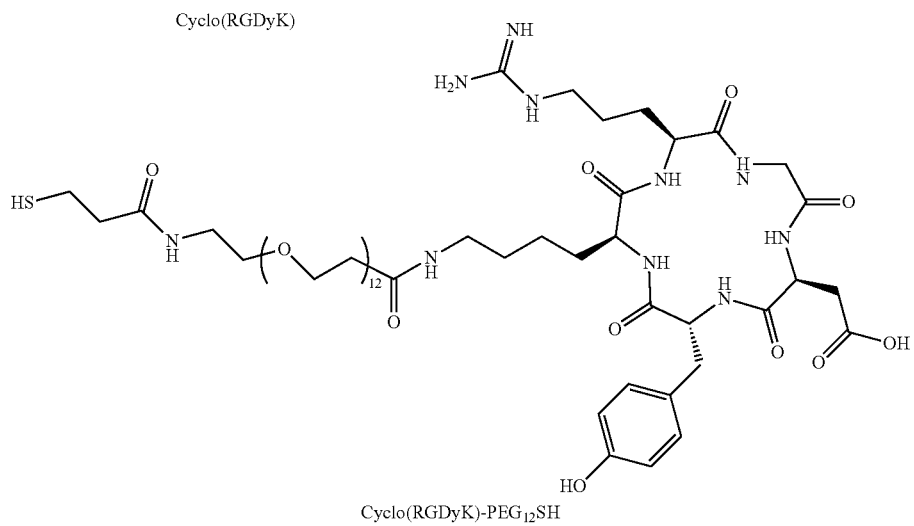

Cyclo(RGDyK)-PEG$_{12}$SH

Cyclo(RGDyK)PEG$_{12}$SH. To the commercially available Cyclo(RGDyK) (0.04 g, 0.064 mmol) (Peptides International Inc, Kentucky) dissolved in DMF (1 mL) was added N-2-pyridyldithiol-tetraoxaoctatriacontane-N-hydroxysuccinimide (0.06 g, 0.065 mmol) (Thermo Scientific, IL) and the solution was allowed to stir for 6 h. The solvent was evaporated; the product neutralized and purified by reverse phase HPLC using water and acetonitrile solvent mixture and lyophilized. The resultant white solid was dissolved in DMF (1 mL) and Dithiothreitol (0.01 g, 0.065 mmol) was added and the solution was allowed to stir for 3 h. The solvent was evaporated; the product neutralized and purified by reverse phase HPLC using water and acetonitrile solvent mixture to give Cyclo(RGDyK)PEG$_{12}$SH as a colorless viscous liquid. (0.025 g, 0.019 mmol, 30.2%). MS (MALDI) ink calcd for $C_{57}H_{98}N_{10}O_{22}S$: 1306.6; found. 1307.5 ([M+H]$^+$).

Cyclo(RGDyK)-PEG$_{12}$SH →

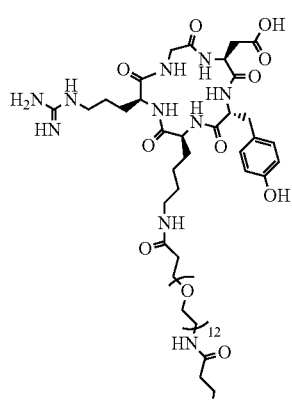

-continued

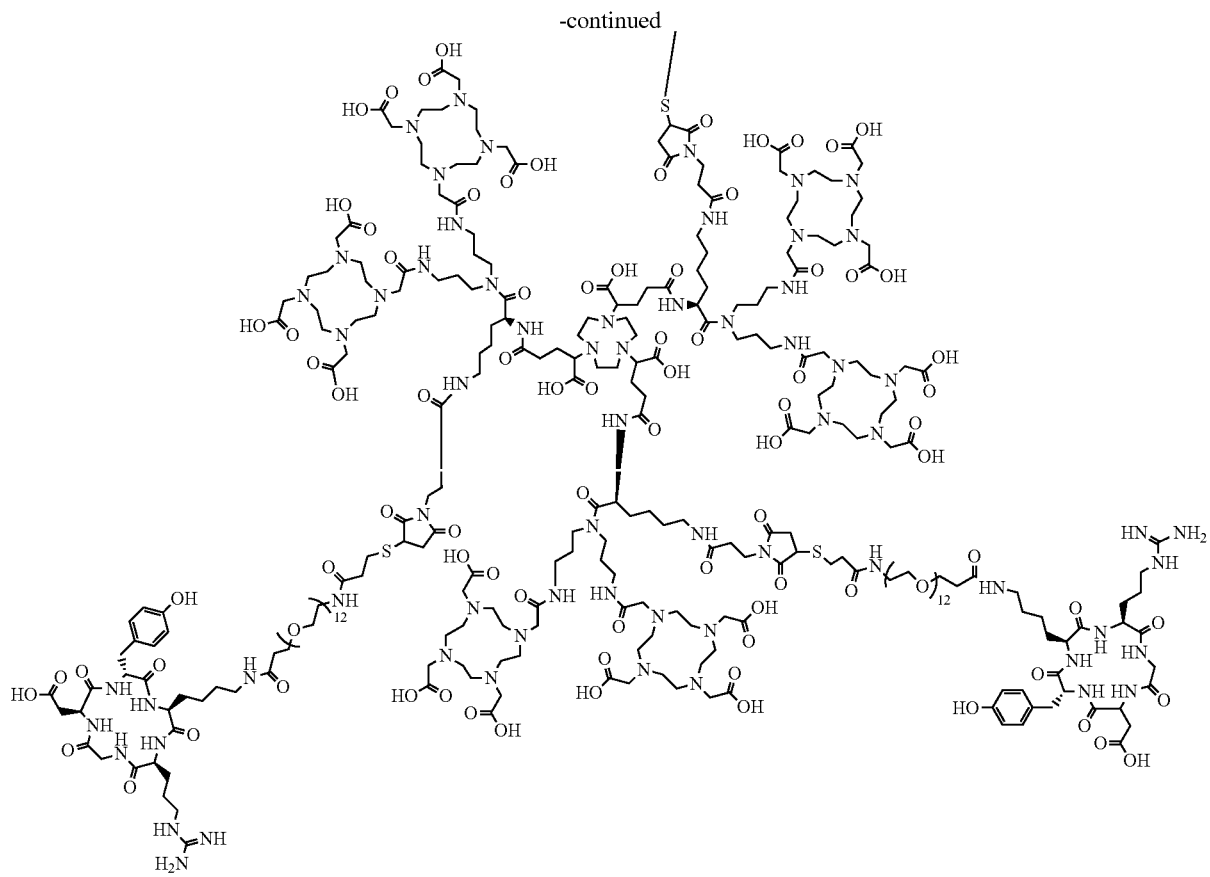

L[PEG$_{12}$Cyclo(RGDyK)]$_3$. To the malemide carrying ligand, L(Mal)$_3$, (0.03 g, 0.007 mmol) dissolved in PBS (1×) was added the thiol carrying Cyclo(RGDyK)SH (0.038 g, 0.028 mmol) and the solution was allowed to stir for 18 h. The solution was purified by reverse phase HPLC using water and acetonitrile solvent mixture to give L[PEG$_{12}$Cyclo(RGDyK)]$_3$ as a white solid. (0.019 g, 0.002 mmol, 35.3%). MS (MALDI) m/z calc'd for C$_{345}$H$_{579}$N$_{75}$O$_{129}$S$_3$: 7936.0; found. 7936.7 ([M+H]$^+$).

6. Labeling of Synthesized Derivatives

Gd$_6$L[PEG$_{12}$Cyclo(RGDyK)]$_3$ The Cyclo(RGDyK) modified ligand L[PEG$_{12}$Cyclo(RGDyK)]$_3$ (0.019 g, 0.002 mmol) was dissolved in water (1 mL) and the pH was adjusted to 7 with NaOH (0.1 M). To this solution was added an excess of GdCl$_3$.6H$_2$O and the pH was again adjusted to 6.5 and allowed to stir at room temperature overnight. The pH was raised above 8 using 1 N aqueous NaOH, which caused the excess Gd$^{3+}$ to precipitate as Gd(OH)$_3$. The solution was filtered and the pH was readjusted to 7 using 1 N HCl. To the resulting solution, DTPA (0.1 mM, 1 mL), was added and the solution was purified using HPLC to give the desired complex. The desired fractions were pooled together and lyophilized to give a white solid. (0.006 g, 0.001 mmol, 51%). MS (MALDI) m/z calcd for C$_{345}$H$_{561}$Gd$_6$N$_{75}$O$_{129}$S$_3$: 8864.3; found. 8864.7 ([M+H]$^+$).

Cold Gd$_6$L[PEG$_{12}$Cyclo(RGDyK)]$_3$. The Gadolinium complex, Gd$_6$L[PEG$_{12}$Cyclo(RGDyK)]$_3$ (0.001 g, 0.112 μmol) was dissolved in a solution of 4-(2-hydroxyethyl)-1-piperazineethanesulfonic acid (HEPES, pH=6.5, 1 M, 1 mL). To the resulting solution was added a solution of GaCl$_3$ (0.1 mg, 0.567 μmol) in 0.6 N HCl (0.3 mL) and the resulting solution was stirred for 1 h. To the mixture was added 500 μL of 5 mM ethylendiaminetetraacetic acid (EDTA) and the mixture, was allowed to incubate for another 5 min at room temperature (EDTA was used to remove nonspecifically bound or free GaCl$_3$ from the Ga-labeled complex). The purification of Ga-labeled complex was carried out by passing the mixture through a preconditioned Sep-Pak C-18 heavy cartridge. After thorough rinsing (3×5 mL, water) of the cartridge, the Ga-labeled complex was eluted by an ethanol water mixture (70:30). The product was characterized by mass spec. MS (MALDI) m/z calcd for C$_{345}$H$_{558}$GaGd$_6$N$_{75}$O$_{129}$S$_3$: 8930.9; found. 8954.8 ([M+Na]$^+$).

Gd$_6$L[Cyclo(RGDyK)]$_3$Ga-68 In a 1.5 mL eppendorf tube containing 80 μg Gd$_6$L[Cyclo(RGDyK)]$_3$ complex in 1 mL of HEPES (pH=6.5) solution, was added a solution of 15 mCi of Ga-68Cl$_3$ in 0.6 N HCl. The reaction mixture was incubated at 75° C. for 0.5 h on a shaker. To this solution, was added DTPA (5 mM, 5 μL) and the reaction mixture was incubated for 5 min at room temperature. The Ga-68-labeled conjugate was purified by passing the mixture through a preconditioned Sep-Pak C-18 light cartridge. After thorough rinsing (3×5 mL, water) of the cartridge, the Ga-68-labeled conjugate was eluted by an ethanol-water mixture (70:30) to give 9 mCi of labeled compound. The product was analyzed by radio-HPLC to determine the radiochemical purity of the product. The compound was determined to have more than 95% purity.

$Gd_6L[PEG_{12}Cyclo(RGDyK)]_3$Ga-68. In a 1.5 mL eppendorf tube containing 100 μg $Gd_6L[PEG_{12}Cyclo(RGDyK)]_3$ complex in 1 mL of HEPES (pH=6.5) solution, was added a solution of 12 mCi of Ga-68Cl$_3$ in 0.6 N HCl. The reaction mixture was incubated at 75° C. for 0.5 h on a shaker. To this solution, was added DTPA (5 mM, 5 μL) and the reaction mixture was incubated for 5 min at room temperature. The Ga-68-labeled conjugate was purified by passing the mixture through a preconditioned Sep-Pak C-18 light cartridge. After thorough rinsing (3×5 mL, water) of the cartridge, the Ga-68-labeled conjugate was eluted by an ethanol-water mixture (70:30) to give 8 mCi of labeled compound. The product was analyzed by radio-HPLC to determine the radiochemical purity of the product. The compound was determined to have more than 95% purity.

For PET/MR imaging, a slightly different procedure was followed. In a 1.5 mL eppendorf tube containing 6 mg of $Gd_6L[PEG_{12}Cyclo(RGDyK)]_3$ complex in 1 mL of HEPES (pH=6.5) solution, was added a solution of 300 μCi of Ga-68Cl$_3$ in 0.6 N HCl. The reaction mixture was incubated at 75° C. for 5 min on a shaker. To this solution, was added DTPA (5 mM, 5 μL) and the reaction mixture was incubated for 1 min at room temperature. The Ga-68-labeled conjugate was purified by passing the mixture through a preconditioned Sep-Pak C-18 heavy cartridge. After thorough rinsing (3×5 mL, water) of the cartridge, the Ga-68-labeled conjugate was eluted by an ethanol-water mixture (70:30) to give up to 200 μCi of labeled compound. The product was analyzed by radio-HPLC to determine the radiochemical purity of the product. The compound was determined to have more than 95% purity.

Integrin $\alpha_v\beta_3$ Receptor-Binding Assay for $Gd_6L[Cyclo(RGDyK)]_3$ and $Gd_6L[PEG_{12}Cyclo(RGDyK)]_3$. The $\alpha_v\beta_3$ integrin-binding affinities of Cyclo(RGDyK), $Gd_6L[Cyclo(RGDyK)]_3$ and $Gd_6L[PEG_{12}Cyclo(RGDyK)]_3$ were determined by a competitive cell-binding assay using $^{125}$I-echistatin (PerkinElmer) as the $\alpha_v\beta_3$-specific radioligand. The experiments were performed on U87MG human glioblastoma cells following a previously reported method.[2] Briefly, U87MG cells were grown in RPMI 1640 medium supplemented with penicillin, streptomycin, and 10% (v/v) fetal bovine serum (FBS) at 37° C. under 5% $CO_2$. Suspended U87MG cells in binding buffer (20 mM Tris, pH 7.4, 150 mM NaCl, 2 mM $CaCl_2$, 1 mM $MgCl_2$, 1 mM $MnCl_2$, 0.1% bovine serum albumin) were seeded on multiwell DV plates (Millipore) with $5\times10^4$ cells per well and then incubated with $^{125}$I-echistatin (10 000 cpm/well) in the presence of increasing concentrations (0-5000 nM) of c(RGDyK) peptide conjugates for 2 h. The final volume in each well was maintained at 200 μL. At the end of incubation, unbound $^{125}$I-echistatin was removed by filtration followed by three rinses with cold binding buffer. The retentate was collected and the radioactivity was measured using a γ-counter. The best-fit $IC_{50}$ values (inhibitory concentration where 50% of the $^{125}$I-echistatin bound on U87MG cells are displaced) of c(RGDyK), $Gd_6L[Cyclo(RGDyK)]_3$ and $Gd_6L[PEG_{12}Cyclo(RGDyK)]_3$ were calculated by fitting the data with nonlinear regression using GraphPad Prism (GraphPadSoftware, Inc.). Experiments were repeated with quintuplicate samples.

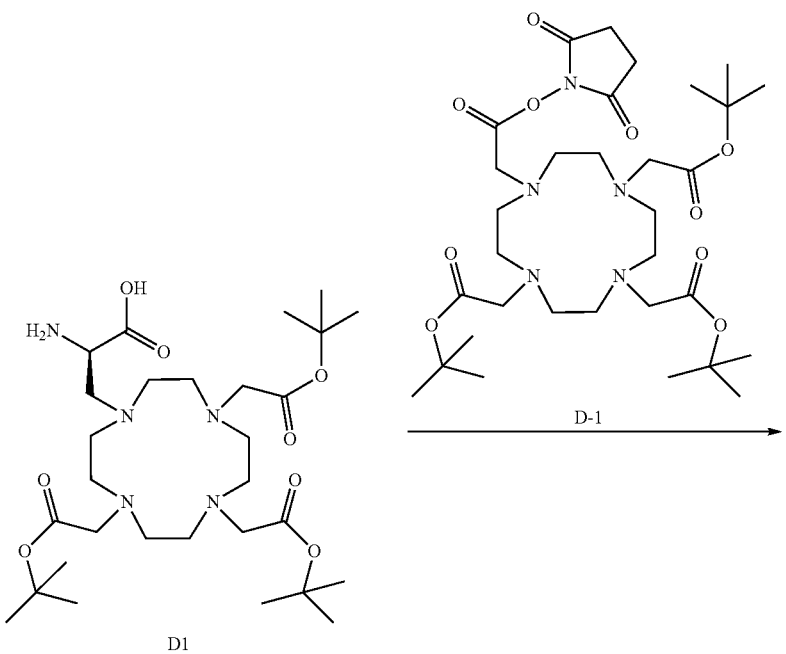

D1

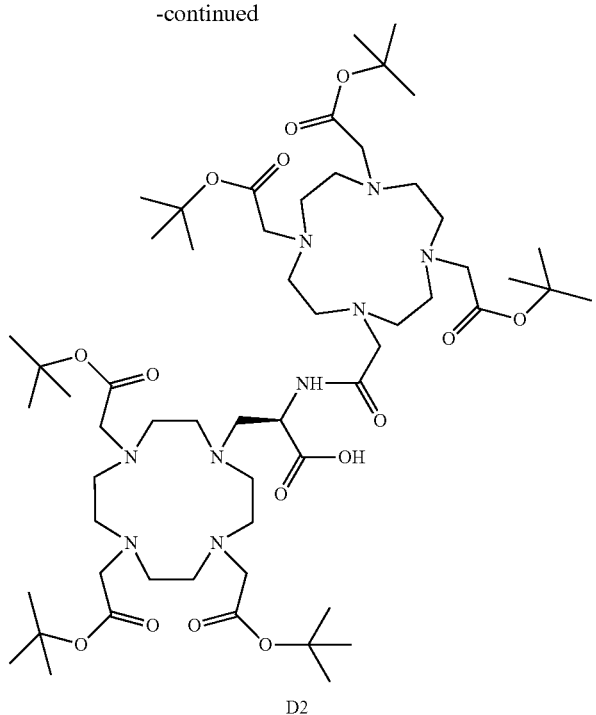

D2

D2 To the previously synthesized D1 (0.25 g, 0.416 mmol) dissolved in DMF (1 mL) was added triethyl amine (0.022 g, 0.224 mmol) and D-1 (0.35 g, 0.523 mmol) and the solution was allowed to stir for 24 h. The solvent was evaporated; the product neutralized and purified by reverse phase HPLC using water and acetonitrile solvent mixture to give D2 as a white solid. (0.17 g, 0.145 mmol, 35.1%). MS (MALDI) m/z calcd for $C_{57}H_{105}N_9O_{15}$: 1155.7.0; found. 1156.8 ([M+H]$^+$).

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alivisatos, *Science*, 271:933-937, 1996.
Behr, et al., *European Journal of Nuclear Medicine*, 25(2): 2293-2352, 1999.
Beyer, et al., *Journal of Nuclear Medicine*, 41:1369-1379, 2000.
Bolskar, *Nanomedicine*, 3:201-213, 2008.
Boswell, et al., *Molecular Pharmaceutics*, 5: 527-539, 2008.
Caravan, et al., *Chemical Reviews*, 99:2293-2352, 1999.
Caravan, *Chemical Society Reviews*, 35:512-523, 2006.
Catana, et al., *Journal of Nuclear Medicine*, 47:1968-1976, 2006.
Chen, et al., *Advanced Materials*, 17:2255-2261, 2005.
Cheng and Tsourkas, *Langmuir*, 24:8169-8173, 2008.
Cheng, et al., *Angewandte Chemie International Edition*, 123:7523-7528, 2011.
Cheon and Lee, *Accounts of Chemical Research*, 41:1630-1640, 2008.
Cherry, *Journal of Nuclear Medicine*, 47:1735-1745, 2006.
Cherry, *The Journal of Clinical Pharmacology*, 41:482-491, 2001.
Dong, et al., *Investigative Radiology*, 33:699-708, 1998.
Duarte, et al., *Bioconjugate Chemistry*, 12:170-177, 2001.

Gao, et al., *Nat. Biotech.*, 22: 969-976, 2004.

Hak, et al., *European Journal of Pharmaceutics and Biopharmaceutics*, 72:397-404, 2009.

*Handbook of Pharmaceutical Salts: Properties, and Use*, Stahl and Wermuth Eds.), Verlag Helvetica Chimica Acta, 2002.

Huang, et al., *Biomaterials*, 32:5177-5186, 2011.

Jennings and Long, *Chemical Communications*, 3511-3524, 2009.

Kang, et al., *Organic Letters*, 11:3654-3657, 2009.

Kobayashi and Brechbiel, *Molecular Imaging*, 2:1-10, 2003.

Kobayashi and Brechbiel, *Advanced Drug Delivery Reviews*, 57:2271-2286, 2005.

Kobayashi, et al., *Journal of Controlled Release*, 111:343-351, 2006.

Kumar, et al., *Inorganic Chemistry*, 33:3567-3575, 1994.

Langereis, et al., *NMR in Biomedicine*, 19:133-141, 2006.

Langereis, et al., *New Journal of Chemistry*, 31:1152-1160, 2007.

Lin, et al., *The Journal of Physical Chemistry B*, 108:15608-15611, 2004.

Link and El-Sayed, *The Journal of Physical Chemistry B*, 103:8410-8426, 1999.

Lux, et al., *Angewandte Chemie International Edition*, 123: 12507-12511, 2011.

Ma, et al., *International Journal of Pharmaceutics*, 354:217-226, 2008.

*March's Advanced Organic Chemistry: Reactions, Mechanisms, and Structure*, 2007.

Morawski, et al., *Magnetic Resonance in Medicine*, 51:480-486, 2004.

Murray, et al., *Journal of the American Chemical Society*, 115:8706-8715, 1993.

Nicolle, et al., *Chemistry—A European Journal*, 8:1040-1048, 2002.

Ntziachristos, et al., *Proceedings of the National Academy of Sciences*, 97:2767-2772, 2000.

Raymond and Pierre, *Bioconjugate Chemistry*, 16:3-8, 2004.

Reichert, et al., *Inorganic Chemistry*, 35:7013-7020, 1996.

Rieter, et al., *Angewandte Chemie International Edition*, 119:3754-3756, 2007a.

Rieter, et al., *Angewandte Chemie International Edition*, 46:3680-3682, 2007b.

Rohrer, et al., *Investigative Radiology*, 40:715-724, 2005.

Rudovský, et al., *Bioconjugate Chemistry*, 17:975-987, 2006.

Santra, et al., *Advanced Materials*, 17:2165-2169, 2005.

Seo, et al., *Nat. Mater.*, 5:971-976, 2006.

Shiraishi, et al., *Journal of Controlled Release*, 148:160-167, 2010.

Terreno, et al., *Chemistry & Biodiversity*, 5:1901-1912, 2008.

Unger, et al., *Magnetic Resonance Imaging*, 7:417-423, 1989.

Venditto, et al., *Molecular Pharmaceutics*, 2:302-311, 2005.

Weissleder, *Science*, 312:1168-1171, 2006.

Zhu, et al., *Magnetic Resonance in Medicine*, 59:679-685, 2008.

What is claimed:

1. A compound of the formula:

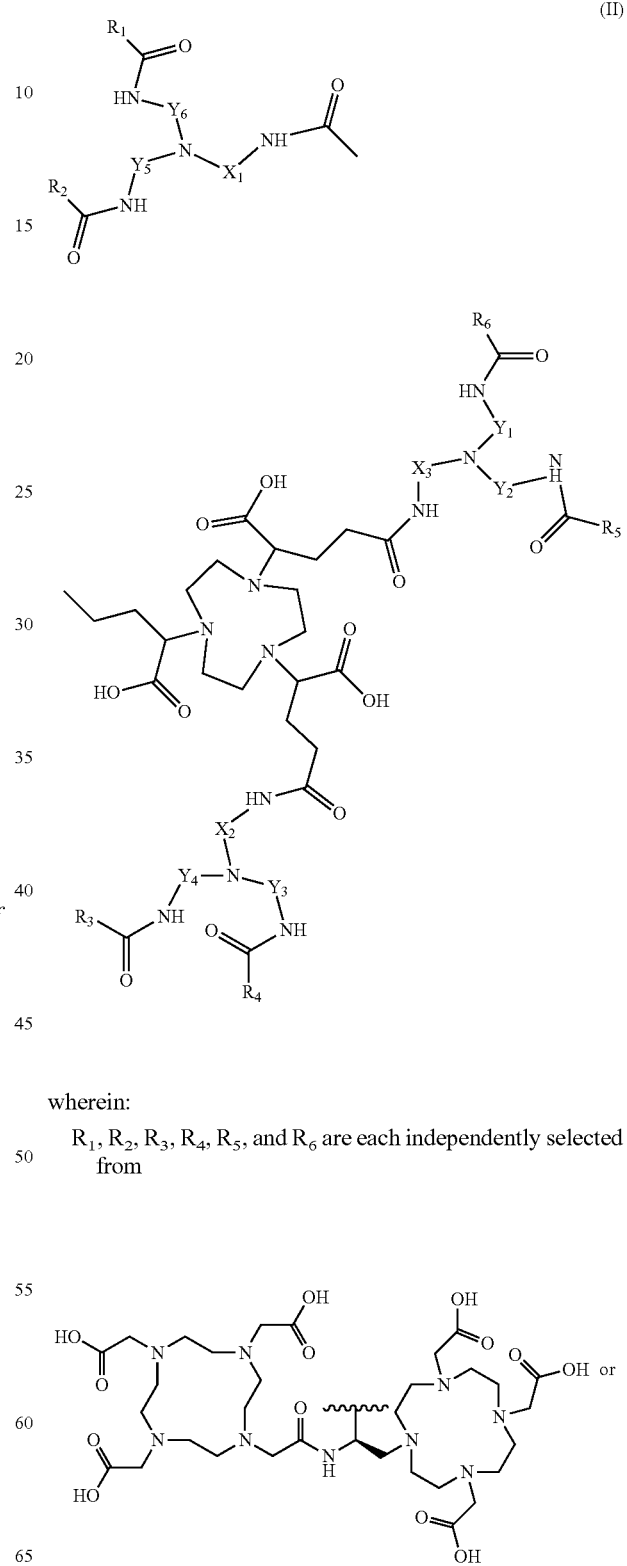

(II)

wherein:

$R_1$, $R_2$, $R_3$, $R_4$, $R_5$, and $R_6$ are each independently selected from

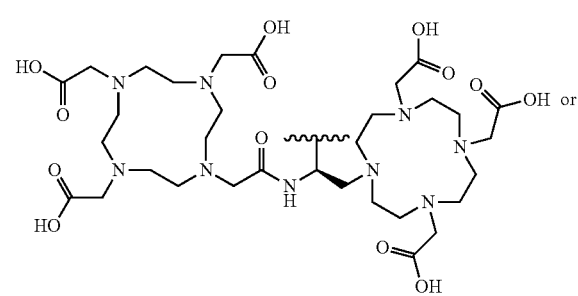

or

-continued

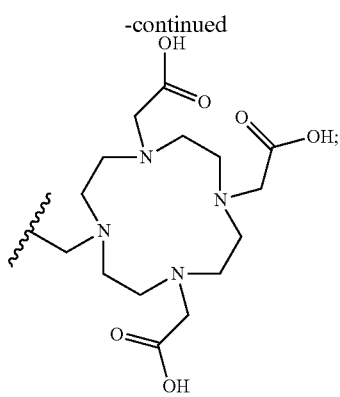

$X_1$, $X_2$, and $X_3$ are each independently alkanediyl$_{(C\leq12)}$, alkenediyl$_{(C\leq12)}$, alkynediyl$_{(C\leq12)}$, arenediyl$_{(C\leq12)}$, heteroarenediyl$_{(C\leq12)}$, alkoxydiyl$_{(C\leq12)}$, alkylaminodiyl$_{(C\leq12)}$, or a substituted version of any of these groups; or an amino acid residue, an amino acid residue linked to a targeting moiety, a PEG linker comprising between 2 and 200 repeating units;

$Y_1$, $Y_2$, $Y_3$, $Y_4$, $Y_5$, and $Y_6$ are each independently alkanediyl$_{(C\leq12)}$, alkenediyl$_{(C\leq12)}$, alkynediyl$_{(C\leq12)}$, arenediyl$_{(C\leq12)}$, heteroarenediyl$_{(C\leq12)}$, alkoxydiyl$_{(C\leq12)}$, alkylaminodiyl$_{(C\leq12)}$, or a substituted version of any of these groups; or an amino acid residue, an amino acid residue linked to a targeting moiety, a PEG linker comprising between 2 and 200 repeating units; and

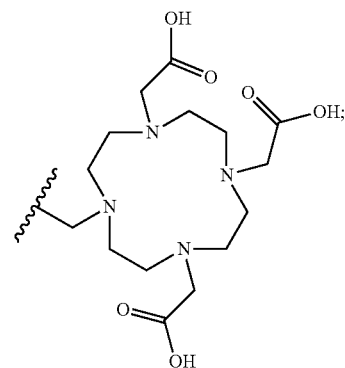

provided that all of $R_1$, $R_2$, $R_3$, $R_4$, $R_5$, and $R_6$ are not or a metal complex or salt thereof.

2. The compound of claim 1, wherein the compound is further defined as:

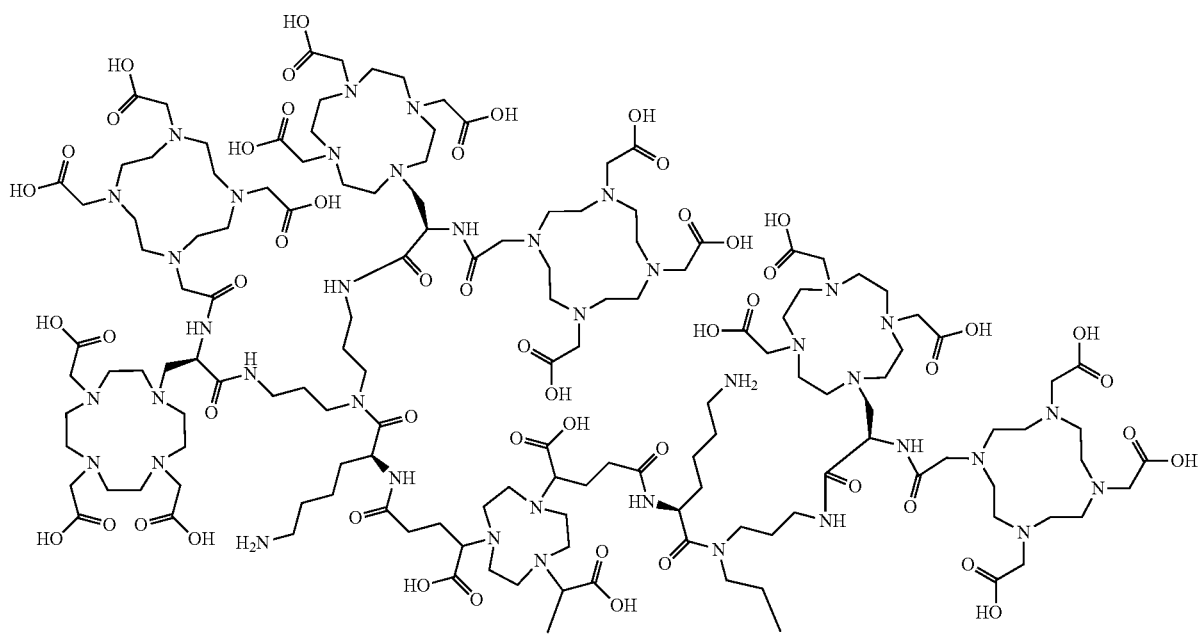

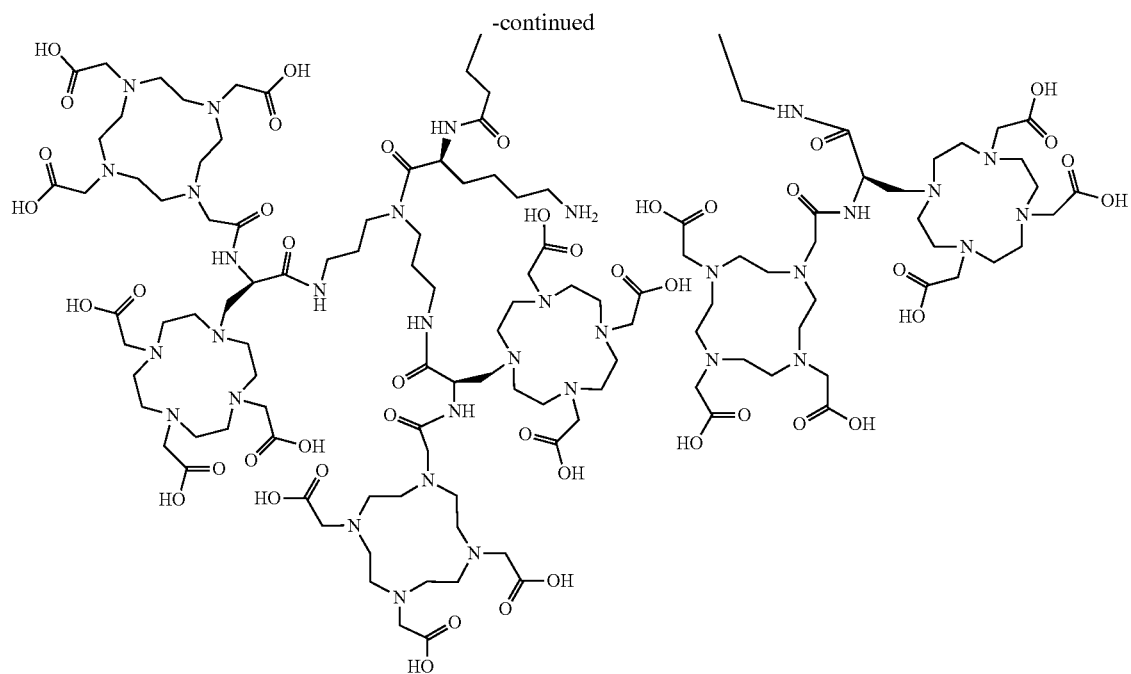
or a metal complex or salt thereof.
* * * * *

UNITED STATES PATENT AND TRADEMARK OFFICE
CERTIFICATE OF CORRECTION

Page 1 of 2

PATENT NO. : 9,463,254 B2
APPLICATION NO. : 14/298688
DATED : October 11, 2016
INVENTOR(S) : Xiankai Sun et al.

It is certified that error appears in the above-identified patent and that said Letters Patent is hereby corrected as shown below:

In Claim 1, Column 132, Lines 5-45, delete two chemical drawings and insert

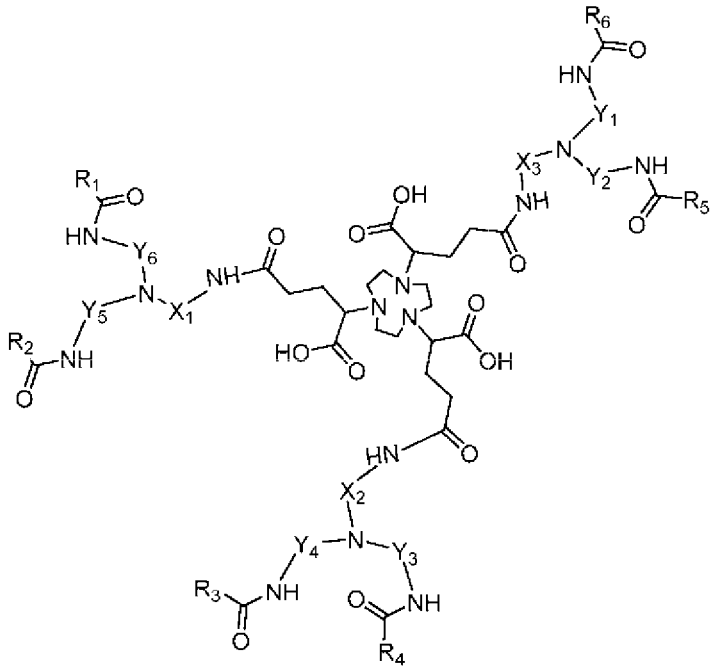

-- therefor.

Signed and Sealed this
Twenty-third Day of May, 2017

Michelle K. Lee
*Director of the United States Patent and Trademark Office*

CERTIFICATE OF CORRECTION (continued)
U.S. Pat. No. 9,463,254 B2

In Claim 2, Columns 133-134, Lines 40-65 through Columns 135-136, Lines 1-30, delete two chemical drawings and insert

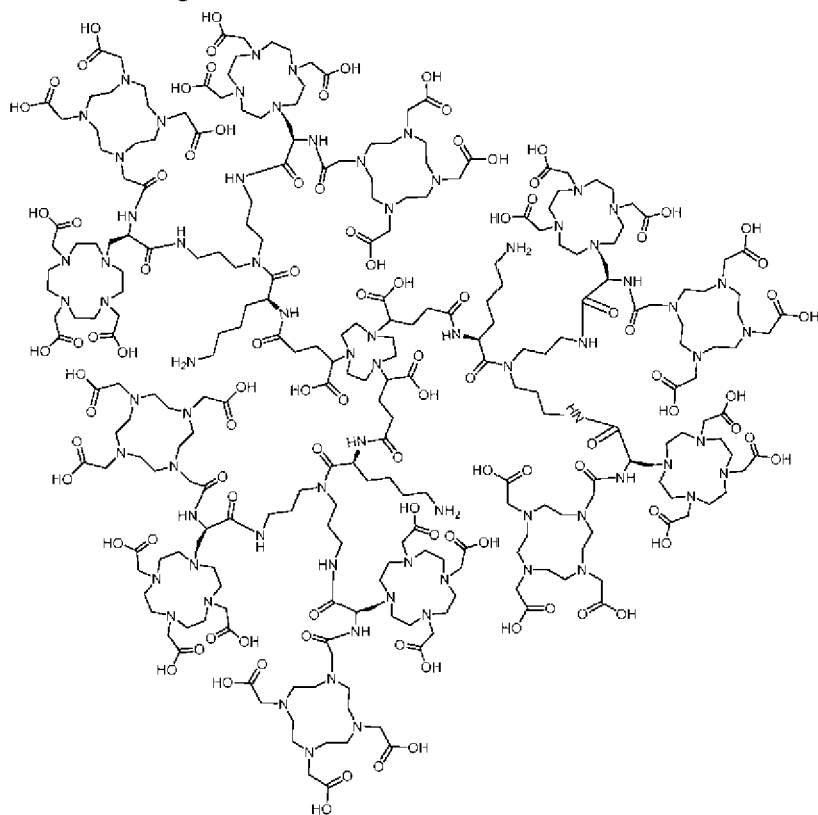

-- therefor.